United States Patent [19]

Breault et al.

[11] Patent Number: 5,843,942

[45] Date of Patent: Dec. 1, 1998

[54] AROMATIC AMINO ETHERS AS PAIN RELIEVING AGENTS

[75] Inventors: Gloria Anne Breault, Congleton; Howard Tucker, Macclesfield; John Oldfield, Wilmslow; Peter Warner, Macclesfield, all of United Kingdom

[73] Assignee: Zeneca Limited, United Kingdom

[21] Appl. No.: 776,275

[22] PCT Filed: Jul. 21, 1995

[86] PCT No.: PCT/GB95/01728

§ 371 Date: Jan. 24, 1997

§ 102(e) Date: Jan. 24, 1997

[87] PCT Pub. No.: WO96/03380

PCT Pub. Date: Feb. 8, 1996

[30] Foreign Application Priority Data

Jul. 25, 1994 [GB] United Kingdom .................... 9414924
Jan. 24, 1995 [GB] United Kingdom .................... 9501288

[51] Int. Cl.⁶ ......................... C07D 237/24; A61K 31/50
[52] U.S. Cl. ............................. 514/247; 544/224; 544/238
[58] Field of Search ................................. 544/224, 238; 514/247, 252

[56] References Cited

U.S. PATENT DOCUMENTS

| | | | |
|---|---|---|---|
| 3,632,760 | 1/1972 | Shen et al. | 424/230 |
| 3,657,430 | 4/1972 | Shen et al. | 424/230 |
| 4,152,452 | 5/1979 | Douglas et al. | 424/304 |
| 4,277,496 | 7/1981 | Los | 424/309 |
| 4,350,822 | 9/1982 | Albright et al. | 560/45 |
| 4,578,390 | 3/1986 | Jensen et al. | 514/255 |
| 4,892,947 | 1/1990 | Mutsukado et al. | 514/247 |
| 5,087,743 | 2/1992 | Janssen et al. | 562/466 |
| 5,189,033 | 2/1993 | Tucker | 514/211 |
| 5,317,101 | 5/1994 | Oldfield et al. | 540/488 |
| 5,318,968 | 6/1994 | Tanikawa et al. | 514/236.5 |
| 5,324,743 | 6/1994 | Dillard et al. | 514/456 |
| 5,409,930 | 4/1995 | Spada et al. | 514/248 |
| 5,420,270 | 5/1995 | Chandrakumar et al. | 540/488 |
| 5,441,950 | 8/1995 | Collins et al. | 514/211 |
| 5,480,883 | 1/1996 | Spada et al. | 514/249 |
| 5,500,427 | 3/1996 | Kubo et al. | 514/256 |
| 5,576,335 | 11/1996 | Sueda et al. | 514/317 |
| 5,604,226 | 2/1997 | Kagawa et al. | 514/247 |

FOREIGN PATENT DOCUMENTS

| | | |
|---|---|---|
| 2111035 | 6/1994 | Canada . |
| 0000816 | 2/1979 | European Pat. Off. . |
| 094065 | 11/1983 | European Pat. Off. . |
| 0122321 | 10/1984 | European Pat. Off. . |
| 0135087 | 3/1985 | European Pat. Off. . |
| 0193822 | 9/1986 | European Pat. Off. . |
| 0200101 | 12/1986 | European Pat. Off. . |
| 0218077 | 4/1987 | European Pat. Off. . |
| 0534667 | 3/1991 | European Pat. Off. . |
| 0475206 | 3/1992 | European Pat. Off. . |
| 0480641 | 4/1992 | European Pat. Off. . |
| 0752421 | 1/1997 | European Pat. Off. . |
| 1543519 | 4/1971 | Germany . |
| 2701854 | 7/1977 | Germany . |
| 1560281 | 2/1980 | United Kingdom . |
| 1576007 | 10/1980 | United Kingdom . |
| WO 92/20642 | 11/1992 | WIPO . |
| WO 96/03380 | 2/1996 | WIPO . |
| WO 96/06822 | 3/1996 | WIPO . |
| WO 96/11902 | 4/1996 | WIPO . |
| WO 97/00863 | 1/1997 | WIPO . |
| WO 97/00864 | 1/1997 | WIPO . |

OTHER PUBLICATIONS

Derwent Patent Abstract of DE 1,543,519 (Abstract No. 71–26731S), 1971.
Derwent Patent Abstract of DE 2,701,854 (Abstract No. 52629Y/30) 1976.
Albright et al., J. Med. Chem. 1983, 26, 1378–1393.
Derwent Patent Abstract of WO 93/23364 (Abstract No. 93–386430/48) 1993.
Brown et al., J. Med. Chem. 1989, 32, 807–826.
Posner, Disorders of Sensation, Cecil Textbook of Medicine, vol. 2, 20th Edition, pp. 2030–2038, 1996.

*Primary Examiner*—Richard L. Raymond
*Assistant Examiner*—Deepak R. Rao
*Attorney, Agent, or Firm*—Paul R. Darkes

[57] ABSTRACT

The present invention relates to compounds of formula (I),

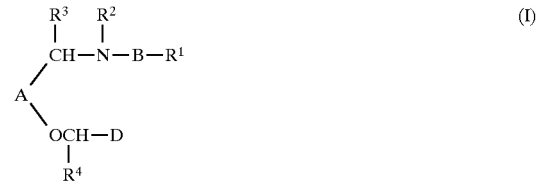

wherein A is an optionally substituted phenyl naphthyl, pyridyl, pyrazinyl, pyridazinyl, pyrimidyl, thienyl, thiazolyl, oxazolyl, thiadiazolyl having at least two adjacent ring carbon atoms or a bicyclic ring system, provided that the $-CH(R^3)N(R^2)B-R^1$ and $-OCH(R^4-)-D$ linking groups arm positioned in a 1,2 relationship to one another on ring carbon atoms and the ring atom positioned ortho to the $-OCHR^4-$ linking group (and therefore in the 3-position relative to the $-CHR^3NR^2-$ linking group) is not substituted; B is an optionally substituted ring system; D is an optionally substituted ring system; $R^1$ is a variety of group as defined in the description; $R^2$ is hydrogen, $C_{1-6}$alkyl, $C_{2-6}$alkenyl, $C_{2-6}$alkynyl, phenyl$C_{1-3}$alkyl or 5- or 6-membered heteroaryl$C_{1-3}$alkyl; $R^3$ is hydrogen or $C_{1-4}$alkyl; $R^4$ is hydrogen or $C_{1-4}$alkyl; and N-oxides of $NR^2$ where chemically possible; and S-oxides of sulphur containing rings were chemically possible; and pharmaceutically acceptable salts and in vivo hydrolysable esters and amides thereof. Process for their preparation, intermediates in theirpreparation, their use as therapeutic agents and pharmaceutical compositions containing them.

13 Claims, No Drawings

AROMATIC AMINO ETHERS AS PAIN RELIEVING AGENTS

This application is a 371 of PCT/GB95/01728 filed Jul. 21, 1995.

This invention relates to novel, aromatic compounds and pharmaceutically-acceptable salts thereof which possess useful pharmacological properties. More particularly the compounds of the invention are antagonists of the pain enhancing effects of E-type prostaglandins. The invention also relates to processes for the manufacture of the aromatic compounds and pharmaceutically-acceptable salts thereof; to novel pharmaceutical compositions containing them; and to use of the compounds in pain relief.

The compounds of the invention are useful in the treatment of pain such as the pain associated with joint conditions (such as rheumatoid arthritis and osteoarthritis), post-operative pain, post-partum pain, the pain associated with dental conditions (such as dental caries and gingivitis), the pain associated with burns (including sunburn), the treatment of bone disorders (such as osteoporosis, hypercalcaemia of malignancy and Paget's disease), the pain associated with sports injuries and sprains and all other painful conditions in which E-type prostaglandins wholly or in part play a pathophysiological role.

Non-steroidal anti-inflammatory drugs (NSAIDS) and opiates are the main classes of drugs in pain relief. However both possess undesireable side effects. NSAIDS are known to cause gastrointestinal irritation and opiates are known to be addictive.

We have now found a class of compounds structurally different to NSAIDS and opiates, and useful in the relief of pain.

The compounds of the invention may also possess anti-inflammatory, anti-pyretic and anti-diarrhoeal properties and be effective in other conditions in which prostaglandin $E_2$ ($PGE_2$) wholly or in part plays a pathophysiological role.

According to the invention there is provided a compound of the formula I;

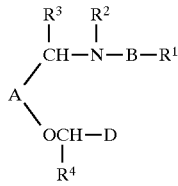

wherein:

A is an optionally substituted: phenyl, naphthyl, pyridyl, pyrazinyl, pyridazinyl, pyrimidyl, thienyl, thiazolyl, oxazolyl, thiadiazolyl having at least two adjacent ring carbon atoms or a bicyclic ring system of the formula:

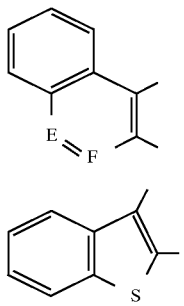

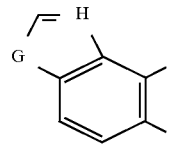

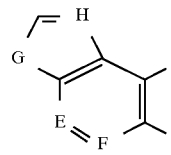

wherein E is nitrogen or CH, F is nitrogen or CH, G is sulphur or oxygen and H is nitrogen or CH; provided that the —CH($R^3$)N($R^2$)B—$R^1$ and —OCH($R^4$)—D linking groups are positioned in a 1,2 relationship to one another on ring carbon atoms and the ring atom positioned ortho to the —OCH$R^4$— linking group (and therefore in the 3-position relative to the —CH$R^3$N$R^2$-linking group) is not substituted;

B is an optionally substituted: phenyl, pyridyl, thiazolyl, oxazolyl, thienyl, thiadiazolyl, isoxazole, pyrazole, furyl, pyrrolyl, imidazolyl, pyrazinyl, pyridazinyl, pyrimidyl, pyridone, pyrimidone, pyrazinone or pyridazinone;

D is optionally substituted: pyridyl, pyrazinyl, pyrimidinyl, pyridazinyl, pyrrolyl, thienyl, furyl, imidazolyl, pyrazolyl, thiazolyl, isothiazolyl, oxazolyl, isoxazolyl or phenyl;

R is positioned on ring B in a 1,3 or 1,4 relationship with the —CH($R^3$)N($R^2$)— linking group in 6-membered rings and in a 1,3-relationship with the —CH($R^3$)N($R^2$)— linking group in 5-membered rings and is carboxy, carboxy$C_{1-3}$alkyl, tetrazolyl, tetrazolyl$C_{1-3}$alkyl, tetronic acid, hydroxamic acid, sulphonic acid, or $R^1$ is of the formula (IIA), (IIB) or (IIC):

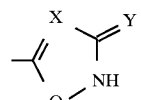  (IIA)

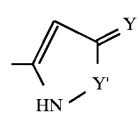  (IIB)

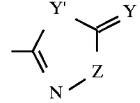  (IIC)

wherein X is CH or nitrogen, Y is oxygen or sulphur $Y^1$ is oxygen or NH, and Z is $CH_2$, NH or oxygen provided that there is no more than one ring oxygen and there are at least two ring heteroatoms; or $R^1$ is of the formula —CONR$^a$R$_{a1}$ or —$C_{1-3}$alkylCONR$^a$R$^{a1}$ wherein R$^a$ is hydrogen, $C_{1-6}$alkyl, $C_{3-7}$cycloalkyl, $C_{3-7}$cycloalkyl$C_{1-3}$alkyl, $C_{5-7}$cycloalkenyl or $C_{5-7}$cycloalkenyl$C_{1-3}$alkyl and R$_{a1}$ is hydrogen, hydroxy or optionally substituted: $C_{1-10}$alkyl, $C_{1-10}$alkenyl, $C_{1-10}$alkynyl, $C_{3-7}$cycloalkyl, $C_{3-7}$cycloalkyl$C_{1-6}$alkyl, $C_{3-7}$cycloalkyl$C_{2-6}$alkenyl, $C_{3-7}$cycloalkyl$C_{2-6}$alkynyl, $C_{5-7}$cycloalkenyl, $C_{3-7}$cycloalkenyl$C_{1-6}$alkyl, $C_{5-7}$cycloalkenyl$C_{2-6}$alkenyl, $C_{5-7}$cycloalkenyl$C_{2-6}$alkynyl, 5- or 6-membered heteroaryl, 5- or 6-membered heteroaryl$C_{1-6}$alkyl, 5- or 6-membered saturated or partially saturated heterocyclyl or 5- or 6-membered saturated or partially saturated heterocyclyl$C_{1-6}$alkyl; or wherein $R^a$ and $R^{a1}$ together with the amide nitrogen to which they are attached ($NR^aR^{a1}$) form an amino acid residue or ester thereof; or $R^1$ is of the formula —CONHSO$_2$R$^b$ or —C$_{1-3}$alkylCONHSO$_2$R$^b$ wherein R$^b$ is optionally substituted: $C_{1-10}$alkyl, $C_{2-10}$alkenyl, $C_{2-10}$alkynyl, $C_{3-7}$cycloalkyl, $C_{3-7}$cycloalkyl$C_{1-6}$alkyl, $C_{3-7}$cycloalkyl$C_{2-6}$alkenyl, $C_{3-7}$cycloalkyl$C_{2-6}$alkynyl, $C_{5-7}$cycloalkenyl, $C_{3-7}$cycloalkenyl$C_{1-6}$alkyl, $C_{5-7}$cycloalkenyl$C_{2-6}$alkenyl, $C_{5-7}$cycloalkenyl$C_{2-6}$alkynyl, 5- or 6-membered heteroaryl, 5- or 6-membered heteroylar$C_{1-6}$alkyl, phenyl, phenyl$C_{1-6}$alkyl, 5- or 6-membered saturated or partially saturated heterocyclyl or 5- or 6-membered saturated or partially saturated heterocyclyl$C_{1-6}$alkyl or $R^1$ is of the formula —CONR$^a$N(R$^c$)R$^d$ or —C$_{1-3}$alkylCONR$^a$N(R$^c$)R$^d$ wherein R$^a$ is as hereinabove defined, R$^c$ is hydrogen or C$_{1-6}$alkyl and R$^d$ is hydrogen, hydroxy or optionally substituted: $C_{1-10}$alkyl, $C_{2-10}$alkenyl, $C_{2-10}$alkynyl, $C_{3-7}$cycloalkyl, $C_{3-7}$cycloalkyl$C_{1-6}$alkyl, $C_{3-7}$ cycloalkyl$C_{2-6}$alkenyl, $C_{3-7}$cycloalkyl$C_{2-6}$alkynyl, $C_{5-7}$cycloalkenyl, $C_{5-7}$cycloalkenyl$C_{1-6}$alkyl, $C_{5-7}$cycloalkenyl$C_{2-6}$alkenyl, $C_{5-7}$cycloalkenyl$C_{2-6}$alkynyl, 5- or 6-membered heteroaryl, 5- or 6-membered heteroaryl$C_{1-6}$alkyl, 5- or 6-membered saturated or partially saturated heterocyclyl, 5- or 6-membered saturated or partially saturated heterocyclyl$C_{1-6}$alkyl, or R$^c$ and R$^d$, together with the nitrogen atom to which they are attached, form a 4 to 8-membered saturated or partially saturated heterocyclic ring or form an amino acid residue or ester thereof;

$R^2$ is hydrogen, $C_{1-6}$alkyl (optionally substituted by hydroxy, cyano, nitro, amino, halo, $C_{1-4}$alkanoyl, $C_{1-4}$alkoxy or trifluoromethyl) $C_{2-6}$alkenyl, $C_{2-6}$alkynyl, $C_{3-6}$cycloalkyl, $C_{3-6}$cycloalkyl$C_{1-3}$alkyl, $C_{3-6}$cycloalkyl$C_{2-3}$alkenyl, $C_{5-6}$cycloalkenyl, $C_{5-6}$cycloalkenyl$C_{1-3}$alkyl, $C_{5-6}$cycloalkenyl$C_{2-3}$alkenyl, phenyl$C_{1-3}$alkyl or 5- or 6-membered heteroaryl$C_{1-3}$alkyl;

$R^3$ is hydrogen or $C_{1-4}$alkyl;

$R^4$ is hydrogen or $C_{1-4}$alkyl;

and N-oxides of —NR$^2$ where chemically possible;

and S-oxides of sulphur containing rings where chemically possible;

and pharmaceutically acceptable salts and in vivo hydrolysable esters and amides thereof.

A 5- or 6-membered heteroaryl ring system is a monocyclic aryl ring system having 5 or 6 ring atoms wherein 1, 2 or 3 ring atoms are selected from nitrogen, oxygen and sulphur.

A 5- or 6-membered saturated or partially saturated heterocyclic (heterocyclyl) ring is a ring system having 5 or 6 ring atoms wherein 1, 2 or 3 of the ring atoms are selected from nitrogen, oxygen and sulphur.

Particular 5- or 6-membered monocyclic heteroaryl rings include pyrrolyl, imidazolyl, pyrazolyl, isothiazolyl, isoxazolyl, pyridyl, pyrazinyl, pyrimidinyl, pyridazinyl, thiazolyl, thiadiazolyl, thienyl, furyl and oxazolyl.

Particular 5- or 6-membered saturated or partially saturated heterocyclic ring ring systems include pyrrolidinyl, pyrrolinyl, imidazolidinyl, pyrazolidinyl, piperidyl, piperazinyl and morpholinyl.

Particular substituents for ring carbon atoms in A include halo, trifluoromethyl, nitro, hydroxy, amino, $C_{1-4}$alkylamino, di$C_{1-4}$alkylamino, cyano, $C_{1-6}$alkoxy, $S(O)_pC_{1-6}$alkyl (p is 0, 1 or 2), $C_{1-6}$alkyl (optionally substituted by hydroxy, amino, halo, nitro or cyano), $S(O)_pCF_3$ (p=0,1 or 2), carbamoyl, $C_{1-4}$alkylcarbamoyl, di($C_{1-4}$alkyl) carbamoyl, $C_{2-6}$alkenyl, $C_{2-6}$alkynyl, $C_{2-4}$alkenylamino, N-$C_{2-4}$alkenyl-N-$C_{1-4}$alkylamino, di-$C_{2-4}$alkenylamino, $S(O)pC_{2-6}$alkenyl, $C_{2-4}$alkenylcarbamoyl, N-$C_{2-4}$alkenyl-N-alkylamino, di-$C_{2-4}$alkenylcarbamoyl, $C_{3-7}$cycloalkyl, $C_{3-7}$cycloalkyl$C_{1-3}$alkyl, $C_{3-7}$cycloalkyl$C_{2-3}$alkenyl, $C_{5-7}$cycloalkenyl, $C_{5-7}$cycloalkenyl$C_{1-3}$alkyl, $C_{5-7}$cycloalkenyl$C_{2-3}$alkenyl, $C_{5-7}$cycloalkenyl$C_{2-3}$alkynyl, $C_{1-4}$alkoxycarbonylamino, $C_{1-4}$alkanoylamino, $C_{1-4}$alkanoyl(N-$C_{1-4}$alkyl)amino, $C_{1-4}$alkanesulphonamido, benzenesulphonamido, aminosulphonyl, $C_{1-4}$alkylaminosulphonyl, di($C_{1-4}$alkyl)aminosulphonyl, $C_{1-4}$alkoxycarbonyl, $C_{1-4}$alkanoyloxy, $C_{1-6}$alkanoyl, formyl$C_{1-4}$alkyl, trifluoro$C_{1-3}$alkylsulphonyl, hydroxyimino$C_{1-6}$alkyl, $C_{1-4}$alkoxyimino$C_{1-6}$alkyl $C_{1-6}$alkylcarbamoylamino, oxazolyl, pyridyl, thiazolyl, pyrimidyl, pyrazinyl and pyridazinyl.

Where a ring nitrogen atom in A can be substituted without becoming quaternised, it is unsubstituted or substituted by $C_{1-4}$alkyl.

Particular substituents for ring carbon atoms in B include halo, amino, $C_{1-4}$alkylamino, di($C_{1-4}$alkyl)amino, trifluoromethyl, nitro, hydroxy, $C_{1-6}$alkoxy, $C_{1-6}$alkyl, amino, $C_{1-4}$alkylamino, di($C_{1-4}$alkyl)amino, cyano, —S(O)$_p$ $C_{1-6}$alkyl (p is 0, 1 or 2), carbamoyl, $C_{1-4}$alkylcarbamoyl and di($C_{1-4}$alkyl)carbamoyl.

Where a ring nitrogen atom in B can be substituted without becoming quaternised, it is unsubstituted or substituted by $C_{1-4}$alkyl.

Particular substituents for optionally substituted groups in $R^{a1}$, $R^b$ and $R^d$ include those mentioned above for ring A.

Particular substituents for carbon atoms in optionally substituted groups in $R^{a1}$ include halo, hydroxy, $C_{1-4}$alkyl, nitro, cyano, amino, carboxy, trifluoromethyl, $C_{1-4}$alkoxy, $C_{3-7}$cycloalkyl, $C_{5-7}$cycloalkenyl, $C_{3-7}$cycloalkyl$C_{1-3}$alkyl, $C_{5-7}$cycloalkenyl$C_{1-3}$alkyl, $C_{3-7}$cycloalkyl$C_{2-3}$alkenyl, $C_{5-7}$cycloalkenyl$C_{2-3}$alkenyl and $C_{1-4}$alkoxycarbonyl. Particular substituents for optionally substituted groups in R$^b$ include halo, trifluoromethyl, nitro, $C_{1-4}$alkyl, hydroxy, amino, cyano, amino, $C_{1-6}$alkoxy, S(O)p$C_{1-6}$alkyl (p is 0, 1 or 2), carbamoyl, $C_{1-4}$alkylcarbamoyl, di($C_{1-4}$alkyl) carbamoyl, $C_{2-6}$alkenyl, $C_{2-6}$alkynyl, $C_{3-7}$cycloalkyl, $C_{5-7}$cycloalkenyl, $C_{3-7}$cycloalkyl$C_{1-3}$alkyl, $C_{5-7}$cycloalkenyl$C_{1-3}$alkyl, $C_{3-7}$cycloalkyl$C_{2-3}$alkenyl, $C_{5-7}$cycloalkenyl$C_{2-3}$alkenyl, $C_{1-4}$alkoxycarbonylamino, $C_{1-4}$alkanoylamino, $C_{1-4}$alkanoyl(N-$C_{1-4}$alkyl)amino, $C_{1-4}$alkanesulphonamido, benzenesulphonamido, aminosulphonyl, $C_{1-4}$alkylaminosulphonyl, di($C_{1-4}$alkyl) aminosulphonyl, $C_{1-4}$alkoxycarbonyl, $C_{1-4}$alkanoyloxy, $C_{1-6}$alkanoyl, formyl$C_{1-4}$alkyl, hydroxyimino$C_{1-6}$alkyl, $C_{1-4}$alkoxyimino$C_{1-6}$alkyl and $C_{1-6}$alkylcarbamoylamino.

The term alkyl when used herein includes straight chain and branched chain substituents for example methyl, ethyl, n-propyl, isopropyl, n-butyl and isobutyl and functional groups on alkyl chains may be anywhere on the chain, for example hydroxyimino$C_{1-6}$alkyl includes 1-(hydroxyimino) propyl and 2-(hydroxyimino)propyl.

Examples of $C_{1-6}$alkoxycarbonyl are methoxycarbonyl, ethoxycarbonyl and t-butoxycarbonyl; examples of carboxy$C_{1-3}$alkyl are carboxymethyl, 2-carboxyethyl, 1-carboxyethyl and 3-carboxypropyl; examples of $C_{1-6}$alkoxycarbonyl$C_{1-3}$alkyl are methoxycarbonylmethyl, ethoxycarbonylmethyl and methoxycarbonylethyl; examples of tetrazolyl$C_{1-3}$alkyl are tetrazolylmethyl and 2-tetrazolylethyl; examples of $C_{1-4}$alkoxy are methoxy, ethoxy, propoxy and isopropoxy; examples of $C_{2-6}$alkenyl are vinyl and allyl; examples of $C_{2-6}$alkynyl are ethynyl and propynyl; examples of $C_{1-4}$alkanoyl are formyl, acetyl, propionyl and butyryl; examples of halo are fluoro, chloro, bromo and iodo; examples of $C_{1-4}$alkylamino are methylamino, ethylamino, propylamino and isopropylamino; examples of di($C_{1-4}$alkyl)amino are dimethylamino, diethylamino and ethylmethylamino; examples of —S(O)$_p$ $C_{1-4}$alkyl are methylthio, methylsulphinyl and methylsulphonyl; examples of $C_{1-4}$alkylcarbamoyl are methylcarbamoyl and ethylcarbamoyl; examples of di($C_{1-4}$alkyl) carbamoyl are dimethylcarbamoyl, diethylcarbamoyl and ethylmethylcarbamoyl; examples of $C_{1-6}$alkyl are methyl, ethyl, propyl and isopropyl; examples of $C_{3-7}$cycloalkyl are cyclopropyl, cyclobutyl and cyclohexyl; examples of $C_{3-7}$cycloalkyl$C_{1-3}$alkyl are cyclopropylmethyl and cyclohexylmethyl; examples of $C_{3-7}$cycloalkyl$C_{2-3}$alkenyl are cyclopropylethenyl and cyclopentylpropenyl; examples of $C_{3-7}$cycloalkyl$C_{2-3}$alkynyl are cyclopropylethynyl and cyclopentylethynyl; examples of $C_{5-7}$alkenyl are cyclopentenyl and cyclohexenyl; examples of $C_{5-7}$cycloalkenyl$C_{1-3}$alkyl are cyclopentenylmethyl and cyclohexenylmethyl; examples of $C_{5-7}$cycloalkenyl$C_{2-3}$alkenyl are cyclohexenylethenyl and cycloheptenylethenyl; examples of $C_{5-7}$cycloalkenyl$C_{2-3}$alkynyl are cyclopentenylethynyl and cyclohexenylethynyl; examples of $C_{1-4}$alkoxycarbonylamino are methoxycarbonylamino and ethoxycarbonylamino; examples of $C_{1-4}$alkanoylamino are acetamido and propionamido; examples of $C_{1-4}$alkanoyl(N-$C_{1-4}$alkyl)amino are N-methylacetamido and N-methylpropionamido; examples of $C_{1-4}$alkanesulphonamido are methanesulphonamido and ethanesulphonamido; examples of $C_{1-4}$alkylaminosulphonyl are methylaminosulphonyl and ethylaminosulphonyl; examples of di($C_{1-4}$alkyl)aminosulphonyl are dimethylaminosulphonyl, diethylaminosulphonyl and ethylmethylaminosulphonyl; examples of $C_{1-4}$alkanoyloxy are acetyloxy and propionyloxy; examples of formyl$C_{1-4}$alkyl are formylmethyl and 2-formylethyl; examples of hydroxyimino$C_{1-6}$alkyl are hydroxyiminomethyl and 2-(hydroxyimino)ethyl; and examples of $C_{1-4}$alkoxyimino$C_{1-6}$alkyl are methoxyiminomethyl, ethoxyiminomethyl and 2-(methoxyimino)ethyl.

Suitable ring systems of the formula (IIA), (IIB) or (IIC) include 5-oxo-4,5-dihydro-1,2,4-oxadiazole-3-yl, 3-oxo-2,3-dihydro-1,2,4-oxadiazole-5-yl, 3-thioxo-2,3-dihydro-1,2, 4-oxadiazole-5-yl, 5-oxo-4,5-dihydro-1,3,4-oxadiazole-2-yl, 5-oxo-4,5-dihydro-1,2,4-triazole-3-yl, 3-oxo-2,3-dihydroisoxazole-5-yl, 5-oxo-1,5-dihydroisoxazole-3-yl and 5-oxo-2,3-dihydropyrazol-3-yl.

Amino acid residues formed from $R^a$ and $R^{a1}$ together with the amide nitrogen to which they are attached and esters thereof include for example radicals of the formula —NH—CH($R^c$)—COO$R^d$ wherein $R^c$ is hydrogen, $C_{1-6}$alkyl, $C_{2-6}$alkenyl, $C_{2-6}$alkynyl, phenyl, phenyl$C_{1-3}$alkyl, 5- or 6-membered heteroaryl or 5- or 6-membered heteroaryl$C_{1-3}$alkyl and $R^d$ is hydrogen or $C_{1-6}$alkyl, wherein alkyl, alkenyl, alkynyl, phenyl and heteroaryl groups are optionally substituted. Examples of substituents include those mentioned above for ring A. In particular hydroxy.

When an alkenyl or alkynyl group is directly linked to the nitrogen of a primary or secondary amine it will be appreciated that the double or triple bond may not be in the 1-position. Similarly alkyl groups which are substituted by halo, hydroxy or an amine may not be substituted by these substituents in the 1-position when the alkyl group is directly linked to the nitrogen of a primary or secondary amine.

Preferably A is an optionally substituted: phenyl, naphthyl, pyridyl, pyrazinyl, pyridazinyl, pyrimidyl, thienyl, thiazolyl, oxazolyl or thiadiazolyl having at least two adjacent ring carbon atoms;

More preferably A is optionally substituted: phenyl, naphthyl, thiadiazolyl, thienyl, pyridyl or pyrimidyl.

Most preferably A is optionally substituted: phenyl or thienyl.

In particular A is optionally substituted phenyl.

Preferably B is optionally substituted: pyridyl, phenyl, thiazolyl, thienyl, pyridazinyl, thiadiazolyl, imidazolyl, pyrazinyl, pyrimidyl, or oxazolyl.

More preferably B is optionally substituted: pyridyl, phenyl, thiazolyl, thienyl, pyridazinyl or oxazolyl.

Most preferably B is optionally substituted: pyridyl, phenyl, thienyl, pyridazinyl or thiazolyl.

In particular B is optionally substituted: pyrid-2,5-diyl, pyridazin-3,6-diyl, phen-1,4-diyl or thien-2,5-diyl.

Preferably D is optionally substituted: pyridyl, thienyl, thiazolyl, furyl or phenyl.

More preferably D is optionally substituted: thienyl, furyl or phenyl.

Most preferably D is optionally substituted phenyl.

Preferred optional substituents for ring carbon atoms in A, are halo, nitro, trifluoromethyl, cyano, amino, $C_{1-6}$alkoxy, carbamoyl, $C_{1-6}$alkyl, $C_{3-7}$cycloalkyl, $C_{3-7}$cycloalkyl$C_{1-3}$alkyl, $C_{3-7}$cycloalkyl$C_{2-3}$alkenyl, $C_{5-7}$cycloalkenyl, $C_{5-7}$cycloalkenyl$C_{1-3}$alkyl, $C_{5-7}$cycloalkenyl$C_{2-3}$alkenyl, $C_{1-4}$alkylcarbamoyl, di($C_{1-4}$alkyl)carbamoyl, $C_{1-4}$alkanoylamino, S(O)$_p$$C_{1-6}$alkyl, $C_{1-4}$alkanesulphonamido, benzenesulphonamido, $C_{1-6}$alkanoyl, $C_{1-4}$alkoxyimino$C_{1-4}$alkyl and hydroxyimino$C_{1-4}$alkyl.

Most preferred optional substituents for ring carbon atoms in A are chloro, bromo and methanesulphonyl.

In particular A is substituted on a ring carbon atom by bromo.

Preferably, when A is a 6-membered ring, A is unsubstituted or substituted in the 4-position relative to the —O—CH($R^4$)— linking group.

Preferred optional substituents for ring carbon atoms of B are halo, amino, di$C_{1-4}$alkylamino, $C_{1-4}$alkylamino, trifluoromethyl, nitro, hydroxy, methyl, $C_{1-4}$alkyl, $C_{1-4}$alkoxy and cyano.

More preferred optional substituents for ring carbon atoms of B are fluoro, chloro, bromo, trifluoromethyl, hydroxy, methyl, methoxy and cyano.

Preferably D is optionally substituted by 1 or 2 substituents selected from halo, trifluoromethyl, nitro, hydroxy, amino, $C_{1-4}$alkylamino, di($C_{1-4}$alkyl)amino, cyano, $C_{1-6}$alkoxy, —S(O)$_p$$C_{1-4}$alkyl (p is 0, 1 or 2), $C_{1-4}$alkanoyl, $C_{1-6}$alkyl, $C_{3-7}$cycloalkyl, $C_{3-7}$cycloalkyl$C_{1-3}$alkyl, $C_{3-7}$cycloalkyl$C_{2-3}$alkenyl, $C_{5-7}$cycloalkenyl, $C_{5-7}$cycloalkenyl$C_{1-3}$alkyl, $C_{5-7}$cycloalkenyl$C_{2-3}$alkenyl, wherein $C_{3-7}$cycloalkyl, $C_{5-7}$cycloalkenyl, $C_{1-6}$alkyl and $C_{1-6}$alkyloxy are optionally substituted by trifluoromethyl, hydroxy, halo, nitro, cyano or amino.

Most preferred optional substituents for D include halo, nitro, hydroxy, cyano, $C_{1-6}$alkyl, amino, $C_{1-6}$alkoxy or carbamoyl.

Most preferably D is unsubstituted.

Preferably A is unsubstituted or substituted by one substituent.

Preferably B is unsubstituted or substituted by one substituent.

Preferably $R^1$ is carboxy, carbamoyl, tetrazolyl or of the formula —CONR$^a$R$^{a1}$ or —CONHSO$_2$R$^b$.

Preferably, R is hydrogen, hydroxy or optionally substituted: $C_{1-6}$alkyl, $C_{2-6}$alkenyl, $C_{2-6}$alkynyl, cyclopropyl$C_{1-4}$alkyl, cyclobutyl$C_{1-4}$alkyl, cyclopentyl$C_{1-4}$alkyl, cyclohexyl$C_{1-4}$alkyl, pyridyl$C_{1-4}$alkyl, pyrimidyl$C_{1-4}$alkyl, pyrazinyl$C_{1-4}$alkyl, furyl$C_{1-4}$alkyl, pyridazinyl$C_{1-4}$alkyl, tetrazolyl$C_{1-4}$alkyl, pyrrolidinyl$C_{1-4}$alkyl, morpholinyl$C_{1-4}$alkyl, imidazolium$C_{1-4}$alkyl, N-methylimidazolium$C_{1-4}$alkyl, pyridinium$C_{1-4}$alkyl, pyridyl, pyrimidyl, pyrazinyl, pyridazinyl, N-methylpyrimidinium, N-methylimidazolyl, pyridinium, pyrimidinium, tetrazolyl, phenyl, cyclopropyl, cyclobutyl, cyclopentyl, cyclohexyl, cyclopentenyl, cyclohexenyl, cycloheptenyl, cyclopentenyl$C_{1-4}$alkyl, cyclohexenyl$C_{1-4}$alkyl or cycloheptenyl$C_{1-4}$alkyl.

More preferably aspect $R^{a1}$ is hydrogen, $C_{1-6}$alkyl (optionally substituted by halo, hydroxy, nitro, cyano, amino, carboxy, $C_{1-4}$-alkoxycarbonyl), pyridyl$C_{1-4}$alkyl, pyrimidyl$C_{1-4}$alkyl, pyrazinyl$C_{1-4}$alkyl, furyl$C_{1-4}$alkyl, pyridazinyl$C_{1-4}$alkyl, tetrazolyl$C_{1-4}$alkyl, or $C_{2-6}$alkenyl.

Most preferably $R^{a1}$ is $C_{1-4}$alkyl (optionally substituted by one or two substituents selected from hydroxy, carboxy and $C_{1-4}$alkoxycarbonyl), pyridyl$C_{1-4}$alkyl and furyl$C_{1-4}$alkyl.

Preferably —$C_{1-3}$alkylCONR$^a$R$^{a1}$ is —CH$_2$CONR$^a$R$^{a1}$.

Preferably —$C_{1-3}$alkylCONHSO$_2$R$^b$ is —CH$_2$CONHSO$_2$R$^b$.

Preferably —$C_{1-3}$alkylCONR$^a$NR$^c$R$^d$ is —CH$_2$CONR$^a$NR$^c$R$^d$.

Preferably $R^b$ is optionally substituted: $C^{1-6}$alkyl, $C_{3-7}$cycloalkyl, $C_{3-7}$cycloalkyl$C_{1-3}$alkyl, $C_{3-7}$cycloalkyl$C_{2-3}$alkenyl, $C_{5-7}$cycloalkenyl, $C_{5-7}$cycloalkenyl$C_{1-3}$alkyl, $C_{5-7}$cycloalkenyl$C_{2-3}$alkenyl, 5- or 6-membered heteroaryl$C_{1-3}$alkyl, 5- or 6-membered saturated or partially saturated heterocyclyl$C_{1-3}$alkyl, phenyl$C_{1-3}$alkyl, phenyl, 5- or 6-membered heteroaryl or 5- or 6-membered saturated or partially saturated heterocyclyl.

More preferably $R^b$ is $C_{1-4}$alkyl (optionally substituted by hydroxy, nitro, cyano, amino, $C_{1-4}$alkylamino, di-$C_{1-4}$alkylamino, $C_{1-4}$alkanoylamino, $C_{1-4}$alkyl-N-$C_{1-4}$alkanoylamino, carbamoyl, $C_{1-4}$alkylcarbamoyl, di-$C_{1-4}$alkanoylcarbamoyl, halo, $C_{1-4}$alkoxy) or optionally substituted phenyl$C_{1-3}$alkyl, pyridyl$C_{1-3}$alkyl, phenyl, thienyl, thiadiazolyl, oxazolyl, isoxazolyl, pyrazolyl or 1,1-dioxidotetrahydrothienyl.

Most preferably $R^b$ is $C_{1-4}$alkyl, hydroxy$C_{1-4}$alkyl, $C_{1-4}$alkoxy$C_{1-4}$alkyl, phenyl (optionally substituted by halo, cyano, nitro, carbamoyl, $C_{1-4}$alkylcarbamoyl, di-$C_{1-4}$alkylcarbamoyl, hydroxy, amino, $C_{1-4}$alkanoylamino, N-$C_{1-4}$alkanoyl-N-$C_{1-4}$alkylamino, $C_{1-4}$alkylamino or di-($C_{1-4}$alkyl)amino), benzyl (optionally substituted by halo, cyano, nitro, carbamoyl, $C_{1-4}$alkylcarbamoyl, di-$C_{1-4}$ alkylcarbamoyl, hydroxy, amino, $C_{1-4}$alkanoylamino, N-$C_{1-4}$alkanoyl-N-$C_{1-4}$alkylamino, $C_{1-4}$alkylamino or di-($C_{1-4}$alkyl)amino), thiadiazolyl (optionally substituted by $C_{1-4}$alkanoylamino, amino, $C_{1-4}$alkylamino or di-$C_{1-4}$alkylamino), thienyl (optionally substituted by halo or pyridyl), isoxazolyl (optionally substituted by $C_{1-4}$alkyl or halo), pyrazolyl (optionally substituted by $C_{1-4}$alkyl or halo) or 1,1-dioxidotetrahydro-2-thienyl.

Preferably $R^c$ is hydrogen and $R^d$ is 5- or 6-membered heteroaryl or $R^c$ and $R^d$, together with the nitrogen atom to which they are attached, form a 5- or 6-membered saturated or partially saturated heterocyclic ring.

More preferably $R^c$ is hydrogen and $R^d$ is pyridyl or $R^c$ and $R^d$, together with the nitrogen atom to which they are attached, form morpholino.

In one aspect $R^1$ is carboxy, carbamoyl or tetrazolyl or $R^1$ is of the formula —CONR$^a$R$^{a1}$ wherein $R^a$ is hydrogen or $C_{1-6}$alkyl and $R^{a1}$ is $C_{1-6}$alkyl (optionally substituted by hydroxy), $C_{2-6}$alkenyl, 1-morpholinyl, 1-piperidinyl, 1-pyrrolidinyl, pyridyl$C_{1-3}$alkyl or $R^1$ is of the formula —CONHSO$_2$R$^b$ wherein $R^b$ is $C_{1-6}$alkyl or phenyl.

In another aspect, $R^1$ is carboxy, tetrazolyl or of the formula —CONR$^a$R$^{a1}$ wherein $R^a$ is hydrogen and $R^{a1}$ is $C_{1-6}$alkyl (optionally substituted by hydroxy) or pyridylmethyl, or $R^1$ is of the formula —CONHSO$_2$R$^b$ wherein $R^b$ is $C_{1-6}$alkyl or phenyl.

Most preferably $R^1$ is carboxy.

More preferably $R^2$ is hydrogen, methyl, ethyl, cyclopropylmethyl, 2-fluoroethyl, 2,2-difluoroethyl, 2,2,2-trifluoroethyl, cyanomethyl, allyl or 2-propynyl.

Most preferably $R^2$ is ethyl, allyl or 2-propynyl.

In particular $R^2$ is ethyl.

In one aspect $R^2$ is hydrogen, $C_{1-6}$alkyl (optionally substituted by hydroxy, cyano or trifluoromethyl), $C_{2-6}$alkenyl, $C_{2-6}$alkynyl, phenyl$C_{1-3}$alkyl or pyridyl$C_{1-3}$alkyl;

Preferably $R^3$ is hydrogen, methyl or ethyl.

Preferably $R^4$ is hydrogen, methyl or ethyl.

Most preferably $R^3$ is hydrogen or methyl.

Most preferably $R^4$ is hydrogen.

In one aspect A is optionally substituted: naphthyl, pyridyl, pyrazinyl, pyridazinyl, pyrimidyl, thienyl, thiazolyl, oxazolyl, thiadiazolyl having at least two adjacent ring carbon atoms or a bicyclic ring system of the formula:

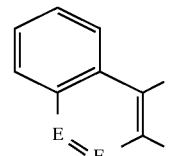

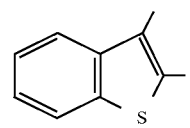

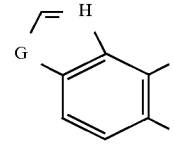

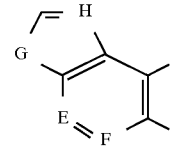

wherein E is nitrogen or CH, F is nitrogen or CH, G is sulphur or oxygen and H is nitrogen or CH.

In another aspect A is optionally substituted phenyl.

In one aspect B is optionally substituted phenyl, pyridyl, thiazolyl, oxazolyl, thienyl, thiadiazolyl, furyl, pyrrolyl, imidazolyl, pyrazinyl or pyrimidyl.

In another aspect B is optionally substituted pyridazinyl.

A preferred class of compounds is that of the formula:

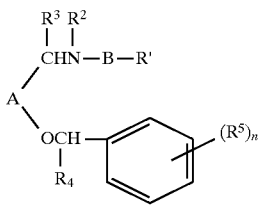

wherein:
A is an optionally substituted:
phenyl, naphthyl, pyridyl, pyrazinyl, pyridazinyl, pyrimidyl, thienyl, thiazolyl, oxazolyl or thiadiazolyl having at least two adjacent ring carbon atoms; provided that the —CH($R^3$)N($R^2$)B—$R^1$ and —OCH($R^4$)Ph—($R^5$)$_n$ linking groups are positioned in a 1,2 relationship to one another on ring carbon atoms and the ring atom positioned ortho to the —OCH$R^4$— linking group (and therefore in the 3-position relative to the —CH$R^3$N$R^2$— linking group) is not substituted.

B is an optionally substituted: phenyl, pyridyl, thiazolyl, oxazolyl, thienyl, thiadiazolyl, imidazolyl, pyrazinyl, pyridazinyl or pyrimidyl.

$R^1$ is positioned on ring B in a 1,3 or 1,4 relationship with the —CH($R^3$)N($R^2$)— linking group and is carboxy, carboxy$C_{1-3}$alkyl, tetrazolyl, tetrazolyl$C_{1-3}$alkyl, tetronic acid, hydroxamic acid, sulphonic acid, or $R^1$ is of the formula —CONR$^a$R$^{a1}$ wherein $R^a$ is hydrogen or $C_{1-6}$alkyl and $R^{a1}$ is hydrogen, $C_{1-6}$alkyl (optionally substituted by halo, hydroxy, nitro, cyano, trifluoromethyl, $C_{1-4}$alkoxy or $C_{1-4}$alkoxycarbonyl), $C_{2-6}$alkenyl (provided the double bond in not in the 1-position), $C_{2-6}$alkynyl (provided the triple bond is not in the 1-position), 5- or 6-membered saturated or partially saturated heterocyclyl$C_{1-3}$alkyl, 5- or 6-membered heteroaryl $C_{1-3}$alkyl, 5- or 6-membered saturated or partially saturated heterocyclyl, or 5- or 6-membered heteroaryl or $R^1$ is of the formula —CONHSO$_2$R$^b$ wherein $R^b$ is $C_{1-6}$alkyl (optionally substituted by halo, hydroxy, nitro, cyano, trifluoromethyl, $C_{1-4}$alkoxy or $C_{1-4}$alkoxycarbonyl), $C_{2-6}$alkenyl (provided the double bond is not in the 1-position), $C_{2-6}$alkynyl (provided the triple bond is not in the 1-position), 5- or 6-membered saturated or partially saturated heterocyclyl$C_{1-3}$alkyl, 5- or 6-membered heteroaryl$C_{1-3}$alkyl phenyl$C_{1-3}$alkyl, 5- or 6-membered saturated or partially saturated heterocyclyl, 5- or 6-membered heteroaryl or phenyl; wherein any heterocyclyl or heteroaryl group in $R^{a1}$ is optionally substituted by halo, hydroxy, nitro, cyano, trifluoromethyl, $C_{1-4}$alkoxy or $C_{1-4}$alkoxycarbonyl and any phenyl, heterocyclyl or heteroaryl group in $R^b$ is optionally substituted by halo, trifluoromethyl, nitro, hydroxy, amino, cyano, $C_{1-6}$alkoxy, S(O)p$C_{1-6}$alkyl (p is 0, 1 or 2), $C_{1-6}$alkyl carbamoyl, $C_{1-4}$alkylcarbamoyl, di($C_{1-4}$alkyl)carbamoyl, $C_{2-6}$alkenyl, $C_{2-6}$alkynyl, $C_{1-4}$alkoxycarbonylamino, $C_{1-4}$alkanoylamino, $C_{1-4}$alkanoyl(N-$C_{1-4}$alkyl)amino, $C_{1-4}$alkanesulphonamido, benzenesulphonamido, aminosulphonyl, $C_{1-4}$alkylaminosulphonyl, di($C_{1-4}$alkyl)aminosulphonyl, $C_{1-4}$alkoxycarbonyl, $C_{1-4}$alkanoyloxy, $C_{1-6}$alkanoyl, formyl$C_{1-4}$alkyl, hydroxyimino$C_{1-6}$alkyl, $C_{1-4}$alkoxyimino$C_{1-4}$alkyl or $C_{1-6}$alkylcarbamoylamino.

$R^2$ is hydrogen, $C_{1-6}$alkyl, optionally substituted by hydroxy, cyano or trifluoromethyl, $C_{2-6}$alkenyl (provided the double bond is not in the 1-position), $C_{2-6}$alkynyl (provided the triple bond is not in the 1-position), phenyl$C_{1-3}$alkyl or pyridyl$C_{1-3}$alkyl;

$R^3$ is hydrogen, methyl or ethyl;
$R^4$ is hydrogen, methyl or ethyl;
$R^5$ is halo, trifluoromethyl, nitro, hydroxy, amino, $C_{1-4}$alkylamino, di($C_{1-4}$alkyl)amino, cyano, $C_{1-4}$alkoxy, —S(O)$_p$$C_{1-4}$alkyl (p is 0, 1 or 2), $C_{1-4}$alkanoyl or $C_{1-4}$alkyl optionally substituted by hydroxy, halo, nitro, cyano or amino; and n is 0, 1 or 2; and N-oxides of —NR$^2$ where chemically possible; and S-oxides of sulphur containing rings where chemically possible; and pharmaceutically acceptable salts and in vivo hydrolysable esters and amides thereof.

Another preferred class of compounds is that of the formula (IV):

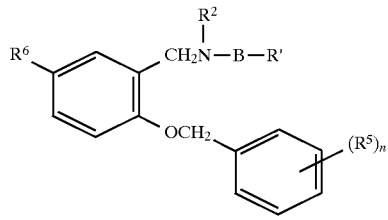

wherein
$R^1$ and $R^2$ are as hereinabove defined, $R^5$ is as hereinabove defined for optional substituents on D, n is 0 or 1, R is hydrogen or as hereinabove defined for substituents on ring carbon atoms in A, and B is phenyl, thienyl, pyridazinyl, pyridyl, or thiazolyl.

Yet another preferred class of compounds is that of the formula (IV) wherein $R^1$ is carboxy and $R^1$, $R^5$, $R^6$, n and B are as hereinabove defined.

Yet another preferred class of compounds is that of the formula (IV) wherein R is ethyl and $R^1$, $R^5$, $R^6$, n and B are as hereinabove defined.

Yet another preferred class of compounds is that of the formula (IV) wherein n is 0 and $R^1$, $R^2$, $R^6$ and B are as hereinabove defined.

Yet another preferred class of compounds is that of the formula (IV) wherein R is chloro, bromo or cyano and $R^1$, $R^2$, $R^6$, n and B are as hereinabove defined.

Yet another preferred class of compounds is that of the formula (IV) wherein $R^6$ is bromo and $R^1$, $R^2$, $R^5$, n and B are as hereinabove defined.

Yet another preferred class of compounds is that of the formula (IV) wherein B is phenyl, thienyl, pyridyl or pyridazinyl and $R^1$, $R^2$, $R^5$, $R^6$ and n are as hereinabove defined.

Yet another preferred class of compounds is that of the formula (IV) wherein B is pyridazinyl and $R^1$, $R^2$, $R^5$, $R^6$ and n are as hereinabove defined.

Particular compounds of the present invention are:
2-[N-(2-benzyloxy-5-bromobenzyl)-N-methylamino] pyridine-5-carboxylic acid;
2-[N-(2-benzyloxy-5-bromobenzyl)-N-ethylamino] pyridine-5-carboxylic acid;
N-(3-pyridylmethyl)-2-[N-(2-benzyloxy-5-bromobenzyl)-NN-ethylamino]-pyridine-5-carboxamide;
2-[N-(2-benzyloxy-5-bromobenzyl)-N-prop-2-yn-1-yl) amino]pyridine-5-carboxylic acid;
2-[N-(2-benzyloxy-5-bromobenzyl)-N-allylamino]pyridine-5-carboxylic acid;
2-[N-(2-benzyloxy-5-chlorobenyl)-N-ethylamino]pyridine-5-carboxylic acid;
2-[N-(2-benzyloxy-5-methylthiobenzyl)-N-ethylamino] pyridine-5-carboxylic acid;
2-[N-(2-(4-methylphenylmethoxy)-5-bromobenzyl)-N-ethylamino]pyridine-5-carboxylic acid;

2-[N-(2-(3-chlorophenylmethoxy)-5-bromobenzyl)-N-ethylamino]pyridine-5-carboxylic acid;
2-[N-(2-(4-chlorophenylmethoxy)-5-bromobenzyl)-N-ethylamino]pyridine-5-carboxylic acid;
2-[N-(2-thienylmethoxy-5-bromobenzyl)-N-ethylamino]pyridine-5-carboxylic acid;
6-[N-(2-benzyloxy-5-bromobenzyl)-N-ethylamino]-2-ethoxypyridine-5-carboxylic acid;
2-[N-(2-(4-bromobenzyloxy)-5-bromobenzyl)-N-ethylamino]pyridine-5-carboxylic acid;
6-[N-(2-benzyloxy-5-bromobenzyl)-N-ethylamino]pyridazine-3-carboxylic acid;
4-[N-(2-benzyloxy-5-nitrobenzyl)-N-ethylamino]benzoic acid;
N-benzenesulphonyl-5-[N-(2-benzyloxy-5-bromobenzyl)-N-ethylamino]thiophene-2-carboxamide;
N-propyl-2-[N-(2-benzyloxy-5-bromobenzyl)-N-ethylamino]thiadiazole-5-carboxamide;
5-[4-(N-(2-benzyloxy-5-bromobenzyl)-N-ethylamino)phenyl]tetrazole;
N-benzenesulphonyl-2-[N-(2-benzyloxy-5-bromobenzyl)-N-ethylamino]thiadiazole-5-carboxamide;
N-(3-pyridylmethyl)-2-[N-(2-benzyloxy-5-bromobenzyl)-N-ethylamino]-thiadiazole-5-carboxamide;
N-propyl-6-[N-(2-benzyloxy-5-bromobenzyl)-N-ethylamino]pyridazine-3-carboxamide;
4-[N-(2-benzyloxy-4-bromobenzyl)-N-ethylamino]benzoic acid;
4-[N-(2-benzyloxy-5-bromobenzyl]-N-ethylamino]benzoic acid;
N-(benzenesulphonyl)-2-[N-(2-benzyloxy-5-bromobenzyl)-N-ethylamino]pyridine-5-carboxamide;
N-(propanesulphonyl)-2-[N-(2-benzyloxy-5-bromobenzyl)-N-ethylamino]pyridine-5-carboxamide;
N-(2-hydroxyethanesulphonyl)-2-[N-(2-benzyloxy-5-bromobenzyl)-N-ethylamino]pyridine-5-carboxamide;
N-(benzenesulphonyl)-6-[N-(2-benzyloxy-5-bromobenzyl)-N-ethylamino]-pyridazine-3-carboxamide;
N-(benzylsulphonyl)-2-[N-(2-benzyloxy-5-methanesulphonylbenzyl)-N-ethylamino]-pyridine-5-carboxamide;
N-(5-methylcarbamoyl-1,3,4-thiadiazole-2-sulphonyl)-2-[N-(2-benzyloxy-5-bromobenzyl)-N-ethylamino]pyridine-5-carboxamide;
N-(3,5-dimethylisoxazole-4-sulphonyl)-6-[N-(2-benzyloxy-5-bromobenzyl)-N-ethylamino]pyridazine-3-carboxamide;
N-(benzenesulphonyl)-4-[N-(2-benzyloxy-5-methanesulphonylbenzyl)-N-ethylamino]benzenecarboxamide;
N-(3-hydroxy-1-carboxyprop-2-yl)-2-[N-(2-benzyloxy-5-bromobenzyl)-N-ethylamino]pyridine-5-carboxamide;
N-(1-carboxypent-2-yl)-2-[N-(2-benzyloxy-5-bromobenzyl)-N-ethylamino]-pyridine-5-carboxamide;
N-benzyl-2-[N-(2-benzyloxy-5-bromobenzyl)-N-ethylamino]pyridine-5-carboxamide;
N-(tetrazol-5-ylmethyl)-2-[N-(2-benzyloxy-5-bromobenzyl)-N-ethylamino]pyridine-5-carboxamide;
2-[N-(2-benzyloxy-5-bromobenzyl)-N-ethylamino]oxazole-4-carboxylic acid;
4-[N-(2-benzyloxy-4-methylbenzyl)-N-ethylamino]benzoic acid;
N-(2-hydroxyethyl)-2-[N-(2-benzyloxy-5-bromobenzyl)-N-ethylamino]thiazole-4-carboxamide;
N-(2(S)-hydroxyprop-1-yl)-2-[N-(2-benzyloxy-5-bromobenzyl)-N-ethylamino]thiazole-5-carboxamide;
N-(2-hydroxyethyl)-2-[N-(2-benzyloxy-5-bromobenzyl)-N-ethylamino]thiazole-5-carboxamide;
5-[3-(N-(2-benzyloxy-5-bromobenzyl)-N-ethylamino)phenyl]tetrazole;
2-[N-(2-benzyloxybenzyl)-N-ethylamino]pyridine-5-carboxylic acid;
N-(benzenesulphonyl)-4-[N-(3-benzyloxy-2-thienylmethyl)-N-ethylamino]benzenecarboxamide;
N-propyl-4-[N-(3-benzyloxy-2-thienylmethyl)-N-ethylamino]benzenecarboxamide;
4-[N-(2-benzyloxy-5-bromobenzyl)-N-ethylamino]-3-ethoxybenzoic acid;
4-[N-(2-benzyloxy-2-thienylmethyl)-N-ethylamino]benzoic acid;
4-[N-(2-benzyloxy-5-bromobenzyl)-N-methylamino]benzoic acid;
N-(3-pyridylmethyl)-4-[N-(2-benzyloxybenzyl)-N-ethylamino]benzenecarboxamide;
5-[6-(N-(2-benzyloxy-5-bromobenzyl)-N-ethylamino)-3-pyridazine]tetrazole;
5-[N-(2-benzyloxy-5-bromobenzyl)-N-ethylamino]pyrazine-2-carboxylic acid; or
N-(3,5-dimethylisoxazol-4-ylsulphonyl)-2-[N-(2-benzyloxy-5-bromobenzyl)-N-ethylamino]pyridine-5-carboxamide;
or pharmaceutically acceptable salts or in vivo hydrolysable esters or amides thereof.

It is to be understood that, insofar as certain of the compounds of formula (I) defined above may exist in optically active or racemic forms, by virtue of the compounds of the formula (I) containing an asymmetric carbon atom, the invention includes in its definition of active ingredient any such optically active or racemic form which possesses pain relieving properties. The synthesis of optically active forms may be carried out by standard techniques of organic chemistry well known in the art, for example by synthesis from optically active starting materials or by resolution of a racemic form. Similarly, pain relieving properties may be evaluated using the standard laboratory techniques referred to hereinafter.

An in vivo hydrolysable ester of a compound of the formula (I) containing carboxy group is, for example, a pharmaceutically acceptable ester which is hydrolysed in the human or animal body to produce the parent acid, for example, a pharmaceutically acceptable ester formed with a (1–6C)alcohol such as methanol, ethanol, ethylene glycol, propranol or butanol, or with a phenol or benzyl alcohol such as phenol or benzyl alcohol or a substituted phenol or benzyl alcohol wherein the substituent is, for example, a halo (such as fluoro or chloro), (1–4C)alkyl (such as methyl) or (1–4C)alkoxy (such as methoxy) group.

A suitable value for an in vivo hydrolysable amide of a compound of the formula I containing a carboxy group is, for example, a N-(1–6C)alkyl or N,N-di-(1–6C)alkyl amide such as N-methyl, N-ethyl, N-propyl, N,N-dimethyl, N-ethyl-N-methyl or N,N-diethyl amide.

A suitable pharmaceutically-acceptable salt of a compound of the formula (I) is, for example, an acid-addition salt of a compound of the formula (I) which is sufficiently basic, for example an acid-addition salt with an inorganic or organic acid such as hydrochloric, hydrobromic, sulphuric, trifluoroacetic, citric or maleic acid; or, for example a salt of a compound of the formula (I) which is sufficiently acidic, for example an alkali or alkaline earth metal salt such as a sodium, calcium or magnesium salt, or an ammonium salt, or a salt with an organic base such as methylamine, dimethylamine, trimethylamine, 2-hydroxyethylamine, piperidine, morpholine or tris-(2-hydroxyethyl)amine or with an amino acid such as lysine or arginine.

In a further aspect the invention provides a process for preparing compounds of the formula (I) or pharmaceutically acceptable salts or in vivo hydrolysable amides or ester thereof, which comprises deprotecting a compound of the formula (VI):

(VI)

wherein $R^7$ is $R^1$ or protected $R^1$, $R^8$ is $R^2$ or protected $R^2$, and, $R^3$, $R^4$, A, B, and D are as hereinabove defined, and any optional substituents are optionally protected and at least one protecting group is present; and thereafter if necessary:

i) forming a pharmaceutically acceptable salt;
ii) forming an in vivo hydrolysable ester or amide;
iii) converting one optional substituent into another optional substituent.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

A suitable protecting group for a hydroxy group is, for example, an arylmethyl group (especially benzyl), a tri-(1–4C)alkylsilyl group (especially trimethylsilyl or tert-butyldimethylsilyl), an aryldi-(1–4C)alkylsilyl group (especially dimethylphenylsilyl), a diaryl-(1–4C)alkylsilyl group (especially tert-butyldiphenylsilyl), a (1–4C)alkyl group (especially methyl), a (2–4C)alkenyl group (especially allyl), a (1–4C)alkoxymethyl group (especially methoxymethyl) or a tetrahydropyranyl group (especially tetrahydroyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryldialkylsilyl group such as a tert-butyldimethylsilyl or a dimethylphenylsilyl group may be removed, for example, by treatment with a suitable acid such as hydrochloric, sulphuric, phosphoric or trifluoroacetic acid, or with an alkali metal or ammonium fluoride such as sodium fluoride or, preferably, tetrabutylammonium fluoride. Alternatively an alkyl group may be removed, for example, by treatment with an alkali metal (1–4C)alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1–4C)alkoxymethyl group or tetrahydropyranyl group may be removed, for example, by treatment with a suitable acid such as hydrochloric or trifluoroacetic acid.

Alternatively a suitable protecting group for a hydroxy group is, for example, an acyl group, for example a (2–4C) alkanoyl group (especially acetyl) or an aroyl group (especially benzoyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide.

A suitable protecting group for an amino, imino or alkylamino group is, for example, an acyl group, for example a (2–4C)alkanoyl group (especially acetyl), a (1–4C) alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or aroyl group may be removed, for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid, and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1–4C)alkyl group (especially methyl or ethyl) which may be removed, for example, by hydrolysis with a suitable base such as an alkali metal hydroxide, for example lithium or sodium hydroxide; or, for example, a tert-butyl group which may be removed, for example, by treatment with a suitable acid such as hydrochloric, sulphuric or phosphoric acid or trifluoroacetic acid.

In another aspect the compounds of the formula (I) or (VI) may be prepared by:

a) reducing a compound of the formula (VII):

(VII)

wherein A, B, D, $R^3$, $R^4$ and $R^7$ are as hereinabove defined;

b) when B is an activated heterocycle and $R^8$ is hydrogen or $C_{1-6}$alkyl, reacting a compound of the formula (IX) with a compound of the formula (X):

(IX)

X—B—R⁷ (X)

wherein A, B, D, $R^3$, $R^4$ and $R^7$ are as hereinabove defined and X is a leaving group;

c) reacting a compound of the formula (VIII) with a compound of the formula (XI):

R⁸NH—B—R⁷ (VIII)

-continued

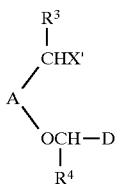
(XI)

wherein A, B, D, $R^3$ and $R^4$ are as hereinabove defined and $X^1$ is a leaving group;

d) converting a compound of the formula (XIII):

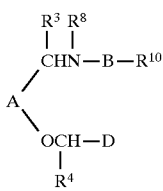
(XIII)

wherein A, B, D, $R^3$, $R^4$ and $R^8$ are as hereinabove defined and $R^{10}$ is a precursor of $R^7$, into a compound of the formula (I) or (VI);

e) when $R^8$ is other than hydrogen, reacting a compound of the formula $R^8X^2$ with a compound of the formula (XIV):

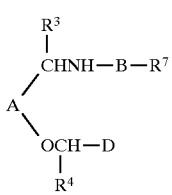
(XIV)

wherein A, B, D, $R^3$, $R^4$ and $R^7$ are as hereinabove defined and $X^2$ is a leaving group;

f) reacting a compound of the formula (XV) with a compound of the formula (XVI):

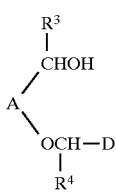
(XV)

R"NH—B—$R^7$ (XVI)

wherein $R^3$, $R^4$, $R^7$, A, B and D are as hereinabove defined and $R^{11}$ is a removable activating group;

g) reacting a compound of the formula (XVII) with a compound of the formula (XVIII):

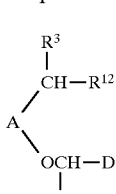
(XVII)

$R^{13}$NH—B—$R^7$ (XVIII)

wherein $R^3$, $R^4$, $R^7$, A, B, and D are as hereinabove defined and $R^{12}$ is a leaving group and $R^{13}$ is an activating group; and thereafter if necessary:

i) removing any protecting groups;

ii) forming a pharmaceutically acceptable salt;

iii) forming an in vivo hydrolysable ester or amide;

iv) converting an optional substituent into another optional substituent.

Particular values for leaving groups include halogen, for example, chloro, bromo and iodo, sulphonates, for example tosylate, p-bromobenzenesulphonate, p-nitrobenzenesulphonate, methanesulphonate and triflate or phosphoric esters such as a diarylphosphoric ester.

Compounds of the formula (VII) can be reduced using agents such as sodium borohydride or sodium cyanoborohydride. The compounds of the formula (VII) may be prepared by reacting a compound of the formula (VIII) with a compound of the formula (XIX)

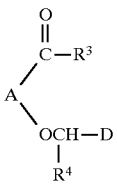
(XIX)

wherein A, D, $R^3$ and $R^4$ are as hereinabove defined.

The reaction between compounds of the formulae (VIII) and (XIX) may be carried out under standard conditions known in the art for the formation of an imine (Schiffs base), which can be reduced in situ. For example imine formation and reduction in situ may be carried out in an inert solvent such toluene or tetrahydrofuran, in the presence of a reducing agent such as sodium cyanoborohydride (NaCNBH$_3$) under acidic conditions (Synthesis 135, 1975; Org. Prep. Proceed. Int. 11, 201, 1979).

Compounds of the formulae (IX) and (X) may be reacted together under standard conditions for example, in an aprotic solvent such as DMF in the presence of a weak base, in a temperature range of ambient to 180° C. Suitable bases include sodium hydrogencarbonate and amide bases such as Hunig's base, N-ethyl-N,N-diisopropylamine, tributylamine or 1,8-diazabicyclo[5.4.0]undec-7-ene (DBU). Suitable values for X include, halo, tosylate, mesylate and triflate. In particular X is chloro or bromo. Preferably $R^7$ is an amide or acid.

The compounds of the formulae (VIII) and (XI) may be reacted together under in an aprotic solvent such as DMF, in the presence of a base such as potassium carbonate or sodium hydride and in a temperature range of 0° C. to 100° C. Suitable values for $X^1$ include halo, tosylate, mesylate and triflate. In particular $X^1$ is bromo.

Particular values for $R^{10}$ include cyano, carbamoyl, alkoxycarbonyl, carboxy and activated carboxy groups such as acid chlorides and activated esters.

The cyano group may be converted into a tetrazole ring by reacting, for example, with ammonium or tin azide in an aprotic solvent such as DMF, in a temperature range of 100° C. to 130° C. For further information on tetrazole synthesis see S. J. Wittenberger and B. J. Donner JOC, 1993, 58, 4139–4141; B. E. Huff et al, Tet. Lett, 1993, 50, 8011–8014; and J. V. Duncia et al, JOC 1991, 56, 2395–2400.

Alkoxycarbonyl may be converted into a carboxy group by acid or base hydrolysis. For example, base hydrolysis may be carried out in an organic solvent such as methanol or THF in a temperature range of ambient to 100° C., in the presence of sodium hydroxide or potassium hydroxide.

Acid hydrolysis may, for example, be carried out or in neat formic acid or neat trifluoroacetic acid optionally in an organic solvent such as dichloromethane.

An alkoxycarbonyl or an activated carboxy group, such as an acid chloride or activated ester, or an acyl group such as an alkanoyl group may be converted to an amide group by reacting with the appropriate amine in an inert solvent such as DMF or dichloromethane, in a temperature range of 0° C. to 150° C., preferably around ambient temperature, in the presence of a base such as triethylamine.

The compounds of the formulae (XIV) and $R^8X^2$ may be reacted together in an aprotic solvent such as DMF in the presence of a base such as sodium carbonate or sodium hydride. Suitable values for $X^2$ are halo, tosylate, mesylate and triflate, in particular halo such as iodo.

The reaction between compounds of the formulae (XV) and (XVI) is conveniently carried out under mild conditions known for the Mitsunobu reaction, for example in the presence of di ($C_{1-4}$alkyl)azocarboxylate and triphenylphosphine or $1^1,1^1$-(azodicarbonyl)dipiperidine and tributylphosphine (Tet. Lett. 34, 1993, 1639–1642) in an inert solvent such as toluene, benzene, tetrahydrofuran or diethylether, in particular toluene. Examples of the removable activating groups are tert-butyloxycarbonyl and trifluoroacetyl.

Compounds of the formulae (XVII) and (XVIII) are generally reacted together in the presence of a strong base such as sodium hydride, lithium diisopropylamide or LiN$(SiMe_3)_2$, in DMF or an etherial solvent such as ethyl ether or THF, in a temperature range of −78° C. to ambient temperature. Suitable values for $R^{12}$ are halogen, for example chloro or bromo, or sulphonates, for example, methanesulphonate or tosylate. Examples of activating groups for $R^{13}$ include tert-butyloxycarbonyl and trifluoroacetyl.

The compounds of the formulae (IX), (XI), (XIII), (XV), (XVII) and (XIX) are conveniently prepared by reacting a compound of the formula (XX) with a compound of the formula (XXI):

wherein A, D and $R^4$ are as hereinabove defined, Z' is —C(O)$R^3$ or a precursor group (such as an ester or nitrile) —CH($R^3$)(NHR$^8$), —CH($R^3$)($X^1$) or precursor group (such as hydroxyalkyl) or —CH($R^3$)OH, as appropriate, and $X^3$ is a leaving group and any functional groups are optionally protected and any precursor groups subsequently converted as necessary.

Suitable leaving groups include tosylate, mesylate, triflate and halo, for example chloro or bromo. The reaction between compounds of the formulae (XX) and (XXI) may be performed in an inert organic solvent such as acetone or DMF, in a temperature range of ambient temperature to 60° C., in the present of a mild base. For example, when $X^3$ is bromo, reacting (XX) and (XXI) together in DMF, at ambient temperature in the presence of a base such as potassium carbonate. Alternatively a phase transfer system could be used. When $X^3$ is hydroxy, the Mitsunobu reaction could be used (O. Synthesis, 1981, 1.).

The compounds of the formula (XIII) may be prepared using processes a), b), c), e), f) or g) from the appropriate starting material wherein $R^7$ is replaced with $R^{10}$.

The compounds of the formula (XIV) may be prepared by using any one of processes a), b) c), d), f) or g) from the appropriate starting materials wherein $R^8$ is hydrogen.

The compounds of the formulae (XVI) and (XVIII) can readily be prepared from compounds of the formula (VIII).

The compounds of the formulae (VIII), (X), (XX) and (XXI) are generally known in the art or can be made by methods analogous to or similar to those used in the Examples or those known in the art for related compounds. Certain compounds of the formula (X), wherein X is chloro or bromo, can be prepared by converting an oxo group in the ring system into chloro or bromo by reacting the oxo ring system with a chlorinating agent, such as sulphonyl chloride, phosphorous trichloride, phosphorous pentachloride or $POCl_3$, or bromonating agent such as phosphorous tribromide or $P(O)Br_3$, in an inert aprotic solvent.

It is also possible to synthesise certain intermediates and even protected compounds using primarily ring synthesis. Here, reference is made to the compendiums 'The Chemistry of Heterocyclic Compounds' E. C. Taylor and A. Weissberger (published by John Wiley and Sons) and 'Comprehensive Heterocyclic Chemistry', A. R Katritzky and C. W. Rees (published by Pergamon Press (Elsevier)).

Optional substituents may be converted into other optional substituents. For example an alkylthio group may be oxidised to an alkylsulphinyl or alkysulphonyl group, a nitro group reduced to an amino group, a hydroxy group alkylated to a methoxy group, or a bromo group converted to an alkylthio group.

Various substituents may be introduced into compounds of the formulae (I) and (III) and intermediates in the preparation of compounds of the formulae (I) and (III), when appropriate, using standard methods known in the art. For example, an acyl group or alkyl group may be introduced into an activated benzene ring using Friedel-Crafts reactions, a formyl group by formylation with titanium tetrachloride and dichloromethyl ethyl ether, a nitro group by nitration with concentrated nitric acid concentrated sulphuric acid and bromination with bromine or tetra(n-butyl) ammonium tribromide.

It will be appreciated that, in certain steps in the reaction sequence to compounds of the formula (I), it will be necessary to protect certain functional groups in intermediates in order to prevent side reactions. Deprotection may be carried out at a convenient stage in the reaction sequence once protection is no longer required.

As stated hereinbefore compounds of the formula (I) are antagonists of the pain enhancing effects of E-type prostaglandins and of value in the relief of mild to moderate pain which, for example, accompanies inflammatory conditions such as rheumatoid arthritis and osteoarthritis. Certain properties of the compounds may be demonstrated using the test procedures set out below:

(a) an in-vitro guinea pig ileum assay which assesses the inhibitory properties of a test compound against $PGE_2$-induced contractions of the ileum; ileum was immersed in oxygenated Krebs solution containing indomethacin (4 $\mu$g/ml) and atropine (1 $\mu$M) and which was maintained at 37° C.; the ileum was subject to a tension of 1 g; a control dose response curve for $PGE_2$-induced contraction of the ileum was obtained; test compound (dissolved in dimethylsulphoxide) was added to the Krebs solution and a dose response curve for the $PGE_2$-induced contraction of the ileum in the presence of the test compound was obtained; the $pA_2$ value for the test compound was calculated;

(b) an in-vivo assay in mice which assesses the inhibitory properties of a test compound against abdominal constriction response induced by the intraperitoneal administration of a noxious agent such as dilute acetic acid or phenylbenzoquinone (hereinafter PBQ) using the procedure disclosed in European Patent Application No. 0218077.

Although the pharmacological properties of the compounds of the formula I vary with structural change as expected, in general activity possessed by compounds of the formula I may be demonstrated at the following concentrations or doses in one or more of the above-mentioned Tests (a) and (b):

Test (a):—$pA_2$>5.3;

Test (b):—$ED_{30}$ in the range, for example, 0.01–100 mg/kg orally.

No overt toxicity or other untoward effects were noted in Test (b) when compounds of the formula I are administered at several multiples of their minimum inhibitory dose.

Prostaglandin receptors and in particular receptors for $PGE_2$ have been tentatively characterised by Kennedy et al. (Advances in Prostaglandin, Thromboxane and Leukotriene Research, 1983, 11, 327). The known $PGE_2$ antagonist SC-19220 blocks the effect of $PGE_2$ on some tissues such as guinea pig ileum or dog fundus but not on other tissues such as the cat trachea or chick ileum. Those tissues which did possess SC-19220 sensitive mediated effects were said to possess $EP_1$ receptors. Based on this compounds of the present invention, possessing activity in Test (a), are $EP_1$ antagonists.

According to a further feature of the invention there is provided a pharmaceutical composition which comprises a compound of the formula (I) or an in-vivo hydrolysable ester thereof or an amide thereof, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel, spray or aqueous or oily solution or suspension; for nasal use, for example a snuff, nasal spray or nasal drops; for vaginal or rectal use, for example a suppository or rectal spray; for administration by inhalation, for example as a finely divided powder or a liquid aerosol; for sub-lingual or buccal use, for example a tablet or capsule; or for parenteral use (including intravenous, subcutaneous, intramuscular intravascular or infusion), for example a sterile aqueous or oily solution or suspension. In general the above compositions may be prepared in a conventional manner using conventional excipients.

The amount of active ingredient (that is a compound of the formula (I) or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition.

According to a further feature of the invention there is provided a compound of the formula (1) or an in-vivo hydrolysable ester or amide or a pharmaceutically-acceptable salt thereof, for use in a method of treatment of the animal (including human) body by therapy.

According to a further feature of the invention there is provided the use of a compound of the formula I, or an in-vivo hydrolysable ester or amide or a pharmaceutically-acceptable salt thereof, in the manufacture of a medicament for use in the relief of pain in the animal (including human) body.

According to a further feature of the invention there is provided a method for the relief of pain in the animal (including human) body in need of such treatment which comprises administering to said body an effective amount of a compound of the formula I, or an in-vivo hydrolysable ester or amide or a pharmaceutically-acceptable salt thereof.

As mentioned above, a compound of the formula (I) is useful in treating the pain which, for example, accompanies inflammatory conditions such as rheumatoid arthritis and osteoarthritis. In using a compound of the formula I for therapeutic or prophylactic purposes it will generally be administered so that a daily dose in the range, for example, 0.1 mg to 75 mg per kg body weight is received, given if required in divided doses. In general lower doses will be administered when a parenteral route is employed. Thus, for example, for intravenous administration, a dose in the range, for example, 0.05 mg to 30 mg per kg body weight will generally be used. Similarly, for administration by inhalation, a dose in the range, for example, 0.05 mg to 25 mg per kg body weight will be used.

Although the compounds of the formula (I) are primarily of value as therapeutic agents for use in warm-blooded animals (including man), they are also useful whenever it is required to antagonise the effects of $PGE_2$ at the $EP_1$ receptor, based on test a). Thus, they are useful as pharmacological standards for use in the development of new biological tests and in the search for new pharmacological agents.

By virtue of their ability to relieve pain, the compounds of the formula I are of value in the treatment of certain inflammatory and non-inflammatory conditions which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam or other analgesics such as paracetamol, tramadol, Codein or in some circumstances morphine. Co-administration of a compound of the formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the formula (I), or an in-vivo hydrolysable ester or amide or pharmaceutically-acceptable salt thereof, in conjunction or admixture with a cyclooxygenase inhibitory non-steroidal anti-inflammatory agent, and a pharmaceutically-acceptable diluent or carrier.

The compounds of the invention may also be used with other anti-inflammatory agents such as an inhibitor of the enzyme 5-lipoxygenase (such as those disclosed in European Patent Applications Nos. 0351194, 0375368, 0375404, 0375452, 037547, 0381375, 0385662, 0385663, 0385679, 0385680).

The compounds of the formula (I) may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compositions of the invention may in addition contain one or more other therapeutic or prophylactic agents known to be of value for the treatment of pain. Thus for example, a known opiate pain-killer (such as dextropropoxyphene, dehydrocodeine or codeine) or an antagonist of other pain or inflammation mediators, such as bradykinin, neurokinin and calcitonin gene related peptides (CGRP), or an alpha$_2$-adrenoceptor agonist, a GABA$_B$ receptor agonist, a calcium channel blocker, a sodium channel blocker, a CCK$_B$ receptor antagonist, or an antagonist or modulator of the action of glutamate at the NMDA receptor may usefully also be present in a pharmaceutical composition of the invention.

The compounds of the present invention may also be administered in bone diseases such as osteoporosis alone or in combination with calcitonin and bisphosphonates and estrogens.

The invention will now be illustrated in the following non-limiting Examples in which, unless otherwise stated:

(i) evaporations were carried out by rotary evaporations in vacuo and work-up procedures were carried out after removal of residual solids by filtration;

(ii) yields are given for illustration only and are not necessarily the maximum attainable;

(iii) the end-products of the formula I have satisfactory microanalysis and their structures were generally confirmed by NMR and mass spectral techniques;

(iv) intermediates were not generally fully characterised and purity was assessed by thin layer chromatographic, infra-red (IR) or NMR analysis;

(v) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture;

(vi) the following abbreviations have been used:

DMF N,N-dimethylformamide;

THF tetrahydrofuran;

DMSO dimethylsulphoxide;

DIBAL diisobutylaluminium hydride;

DEAD diethylazodicarboxylate.

EXAMPLE 1

40% Aqueous sodium hydroxide (100 mL) was added to a solution of methyl 4-[N-(2-benzyloxybenzyl)-N-ethylamino]benzoate (44.0 g) in a mixture of methanol (200 mL) and tetrahydrofuran (100 mL) and the resulting mixture was heated under reflux for 6 hours. The reaction mixture was reduced to half its volume on a rotary evaporator and water (300 mL) was added. The mixture was acidified with acetic acid, the precipitate was filtered, washed three times with diethyl ether (50 mL each time) and dried in a vacuum oven at 60° C. to give 4-[N-(2-benzyloxybenzyl)-N-ethylamino]benzoic acid, melting point 165° C., yield 38.0 g (89%).

$^1$H-NMR (DMSO-d$_6$): δ1.14 (t, 3H, J=6.9 Hz.), 3.51 (q, 2H, J=6.9 Hz), 4.58 (s, 2H), 5.2 (s, 2H), 6.59–7.72 (m, 13H).

EXAMPLE 2

The compounds listed in the appended Tables 1 to 1 g were prepared using the appropriate starting materials using a similar method to that of example 1.

EXAMPLE 3 tert-Butyl-4-[N-(2-benzyloxybenzyl)-N-ethylamino]-2-fluorobenzoate (1.81 g) in formic acid (5 mL) was heated on a steam bath until a clear solution was obtained. The reaction mixture was evaporated to dryness and the oil obtained solidified on trituration with diethyl ether to give 4-[N-(2-benzyloxybenzyl)-N-ethylamino]-2-fluorobenzoic acid, yield 0.51 g, mp 154° C.

Analysis C$_{23}$H$_{22}$ FNO$_3$; theory; C:72.8; H: 5.8; N: 3.7; Found; C: 72.9; H: 5.9; N: 3.5.

The following compounds were prepared as described above;

4-[N-(2-benzyloxy-5-bromobenzylamino)]-2-fluorobenzoic acid, mp 153° C.

4-[N-(2-benzyloxy-5-bromobenzyl)-N-ethylamino]-2-fluorobenzoic acid, mp 204° C.

The t-butyl esters used as starting materials were prepared as outlined in Reference example 1 using t-butyl-4-amino-2-fluorobenzoate as starting material.

EXAMPLE 4

A solution of [N-(2-benzyloxy-5-bromobenzyl)-N-ethylamino]benzoyl chloride (1.04 g) in dichloromethane (20 mL) was added dropwise to a solution of 3-aminomethylpyridine (0.245 g) and triethylamine (1.14 g) in dichloromethane (30 mL) cooled to 0° C. The reaction mixture was allowed to warm to ambient temperature, was stirred at this temperature for 30 minutes and was washed with saturated, aqueous sodium bicarbonate solution and dried. The solvent was removed under vacuum and the residue was subjected to chromatography, eluted with a mixture of methanol and ethyl acetate (3:97 v/v). The material thus obtained was crystallized from ethanol to give 4-[N-(2-benzyloxy-5-bromobenzyl)-N-ethylamino]-N-(3-pyridylmethyl)-benzamide, yield 0.36 g, mp 119°–121° C.

Analysis C29H28BrN3O2 theory: C: 65.7; H: 5.3; N: 7.9. Found: C: 65.8; H: 5.3; N: 7.7.

The [N-(2-benzyloxy-5-bromobenzyl)-N-ethylamino] benzoyl chloride used as starting material was prepared as follows:

Oxalyl chloride (1.14 g) was added to a solution of [N-(2-benzyloxy-5-bromobenzyl)-N-ethylamino]benzoic acid (4.0 g) in dichloromethane (100 mL) and stirred for 20 hours. The solvent was evaporated under reduced pressure and the residue obtained was used directly without further purification or characterization.

EXAMPLE 5

The compounds listed in Tables 2 to 2 g were prepared from the appropriate acid and amine using a similar method to that described in example 4.

EXAMPLE 6

Diphenylphosphorylazide (0.61 g) was added to a cooled (0° C.) solution of 2-[N-(2-benzyloxy-5-bromobenzyl)-N-ethylamino]thiazolyl-5-carboxylic acid (1.0 g) in DMF (10 mL) and the mixture was stirred at ice-bath temperature for 30 minutes. Neat n-propylamine (0.72 g) was added and the mixture was stirred at ambient temperature for 72 hours. Water (50 mL) was added to the reaction mixture and this was extracted three times with ethyl acetate (20 mL each time). The ethyl acetate extracts were dried and evaporated to dryness. The residue obtained was subjected to chromatography, the fraction eluting with a mixture of ethyl acetate and dichloromethane (20:80 v/v) was evaporated to dryness and on trituration with methanol gave 2-[N-(2-benzyloxy-5-bromobenzyl)-N-ethylamino]-N-(n-propylamino)thiazole-5-carboxamide, yield 0.175 g, mp 163° C.

Analysis C$_{23}$H$_{26}$BrN$_3$O$_2$S theory: C: 56.6; H: 5.4; N: 8.6. Found: C: 56.4; H: 5.3; N: 8.4.

EXAMPLE 7

The compounds listed in Tables 3 and 3a were prepared from the appropriate acid and amine using a similar method to that described in example 6 using the appropriate starting materials.

EXAMPLE 8

A mixture of methyl 4-[N-(2-benzyloxy-5-bromobenzyl) amino]benzoate (1.0 g) and ethanolamine (0.425 g) was stirred and heated at 150° C. for 6 hours and allowed to cool to ambient temperature. The residue was subjected to medium pressure chromatography on silica eluted with ethyl acetate initially and then with a mixture of methanol and ethyl acetate (5/95 v/v) to give 4-[N-(2-benzyloxy-5-bromobenzyl)amino]-N-(2-hydroxyethylamino)benzamide, yield (0.32 g), mp 121°–122° C.

Analysis: C$_{23}$H$_{23}$BrN$_2$O$_3$: theory: C: 60.7; H: 5.1; N: 6.2; found: C: 61.0: H: 5.0; N: 5.9.

$^1$H-NMR (DMSO-d$_6$): δ3.28 (t, 2H, J=5.8 Hz), 3.46 (t, 2H, J=5.8 Hz) 4.32 (s, 1H), 5.2 (s, 2H), 6.64 (s, 1H), 6.51–7.62 (m, 12H), 7.94 (t, 1H J=5 Hz).

Using this same method with the appropriate staring materials there were prepared:
4-[N-(2-benzyloxy-5-bromobenzyl)amino]-N-(3-pyridylmethyl)benzamide, mp 179° C.;
2-[N-(2-benzyloxy-5-bromobenzyl)-N-ethylamino]-N-(2-hydroxyethyl)thiophene-5-carboxamide, mp 95° C.;
4-[N-(2-benzyloxybenzyl)amino]-N-(2-hydroxyethyl) benzamide, mp 134° C.;
4-[N-(2-benzyloxybenzyl)-N-ethylamino]-N-(2-hydroxyethyl)benzamide, mp 95°–97° C.

EXAMPLE 9

1-(3—Dimethylaminopropyl)ethylcarbodiimide hydrochloride (0.85 g) was added to a stirred mixture of 2-[N-(2-benzyloxy-5-bromobenzyl)-N-ethylamino]thiazole-5-carboxylic acid (1 g), benzenesulphonamide (0.35 g), 4-dimethylaminopyridine (0.27 g) and triethylamine (0.225 g) in N,N-dimethylformamide (100 mL) and the mixture was stirred at ambient temperature for 16 hours. Water (30 mL) was added to the reaction mixture which was then extracted three times with ethyl acetate (20 mL each time). The combined ethyl acetate extracts were washed consecutively with aqueous 2N HCL (3×10 mL), aqueous saturated NaHCO solution (3×10 mL) and water (10 mL) and dried. The residue obtained on evaporation of the solvent was filtered through silica using ethyl acetate as eluant. The solvent was evaporated and on trituration with diethyl ether the residue gave 2-[N-(2-benzyloxy-5-bromobenzyl)-N-ethylamino]-N-(phenylsulphonyl)thiazole-5-carboxamide, yield 0.358 g, mp 140°–145° C.

Analysis: C$_{26}$H$_{24}$ BrN$_3$O$_4$S hemihydrate: theory C: 52.4; H: 4.2; N: 7.0. Found C: 52.1; H: 4.0; N: 6.7.

$^1$H NMR (DMSO-d$_6$): δ1.08 (t, 3H J=6.2 Hz), 3.44 (q, 2H J=6.2), 4.62 (s, 2H), 5.15 (s, 2H), 7.06–7.82 (m, 14H).

EXAMPLE 10

The compounds listed in Table 4 were prepared using a similar method that described in example 9 using the appropriate acid and amine or sulphonamide as starting materials.

EXAMPLE 11

A mixture of 4-[N-(2-benzyloxy-5-bromobenzyl)-N-ethyl-amino]benzonitrile (3.79 g), sodium azide (0.9 g) and ammonium chloride (1.4 g) in N,N-dimethylformamide (30 mL) was heated and stirred at 120° C. for 18 hours. The reaction mixture was allowed to cool and was poured into water (100 mL). The precipitate was filtered and dried. On crystallization from acetic acid there was obtained 5-[4-[N-(2- benzyloxy-5-bromobenzyl)-N-ethylamino)phenyl] tetrazole, yield 1.2 g, mp 206°–208° C.

Analysis. C$_{23}$H$_{22}$BrN$_5$O Theory: C: 59.5; H: 4.8; N: 15.1. Found: C: 59.9; H: 4.8; N: 14.8.

$^1$H NMR (DMSO-d$_6$): δ1.16 (t, 3H J=6.8 Hz), 3.55 (d, 2H J=6.8), 4.57 (s, 2H), 5.21 (s, 2H), 6.73–7.81 (m, 12H).

EXAMPLE 12

The compounds listed in Table 5 and 5a were prepared using a similar method to that described in example 11 using the appropriate nitriles as starting materials.

EXAMPLE 13

A mixture of 2-benzyloxy-5-bromobenzaldehyde (4.2 g) and 2-amino-N-propyl-1,3,4-thiadiazole-5-carboxamide (2.7 g) in toluene (200 mL) was heated under reflux for 2 hours. The solvent was evaporated and residue was dissolved in ethanol (100 mL) and was heated under reflux for 3 hours then allowed to cool to ambient temperature. Sodium borohydride (0.53 g) was added and the reaction mixture was stirred for 16 hours then poured into water (500 mL). The aqueous mixture was extracted 4 times with ethyl acetate (50 mL each time), the combined extracts were washed 3 times with water (100 mL each time) and dried (MgSO$_4$). The residue obtained on removal of the solvent was subjected to chromatography on silica, eluting with a mixture of ethyl acetate and dichloromethane (1/5 v/v), to give 2-[N-(2-benzyloxy-5-bromobenzyl)amino]-N-propyl-1,3,4-thiadiazole-5-carboxamide, yield 0.81 g, mp 154° C.

Analysis C$_{20}$H$_{21}$ BrN$_4$O$_2$S: theory: C: 52.1; H: 4.6; N: 12.1. Found: C: 52.0; H: 4.5; N: 12.2.

$^1$H NMR (DMSO-d$_6$): δ0.86 (t, 3H J=7.3 Hz), 1.51 (m, 2H), 3.17 (q, 2H), 4.55 (d, 2H J=5.6 Hz, 5.18 (s, 2H), 7.04–7.47 (m, 8H), 8.55 (t, 1H J=5.7 Hz), 8.69 (t, 1H J=6 Hz).

The 2-amino-5-(N-propyl)-1,3,4-thiadiazolecarboxamide used as starting material was prepared as described in J Prakt Chem 331, 243, 1989 and J Prakt Chem 332, 55, 1990 using a similar method to that of reference example 1.

EXAMPLE 14

Ethyl 2-[4-(2-benzyloxy-5-bromobenzylamino)phenyl] butanoate (4.2 g) was diluted in a solution of methanol (20 ml) and THF (20 ml). A 2N aqueous solution of sodium hydroxide was added and the mixture stirred at ambient temperature for 18 hours. The volume of solvent was reduced to half the original volume and water (20 ml) added. The mixture was acidified with 2N HCl to pH 3 and extracted with ethyl acetate (3×50 ml). The combined extracts were dried (MgSO$_4$) and evaporated and the residue was subjected to chromatography, eluting with 10% EtOAc/ CH$_2$Cl$_2$, to give 2-[4-(2-benzyloxy-5-bromobenzylamino) phenyl]butanoic acid (yield 1.31 gum).

EXAMPLE 15

A mixture of 6-[N-(2-benzyloxy-5-bromobenzyl)-N-ethylamino]pyridazine-3-carboxamide (61.7 g), sodium hydroxide (28 g) and isopropanol (400 ml) was heated at reflux for 1 hour. The mixture was cooled to 70° C. and water (800 ml) was added over 30 minutes. The mixture was acidified to pH 3–4 with a solution of formic acid (41.5 ml) in water (200 ml) over 30 minutes, at 25°–30° C. The mixture was cooled to 10° C., the produce filtered off, washed with water and dried to give 6-[N-(2-benzyloxy-5-bromobenzyl)-N-ethylamino]pyridazine-3-carboxylic acid (60.2 g, 97.2% yield).

The starting material was prepared as follows:

A mixture of 6-oxo-1,6-dihydropyridazine-3-carboxylic acid (117.24 g) [Ref: British Patent 856, 409], n-butyl acetate (293 ml), n-butanol (410 ml) and conc. $H_2SO_4$ (5.9 ml) was heated at reflux for 1 hour. The solvent was evaporated and the residue washed with n-butyl acetate to give n-butyl 6-oxo-1,6-dihydropyridazine-3-carboxylate (130.6 g, 79.6% yield), mpt 79°–8° C.

$^1$H-NMR ($d_6$-DMSO): δ0.93 (t, 3H, J=7.5 Hz), 1.40 (sextet, 2H, J=7.5 Hz), 1.67 (m, 2H), 4.28 (t, 2H, J=6.5 Hz), 6.96 (d, 1H, J=10 Hz), 7.83 (d, 1H, J=10 Hz), 13.56 (broad s, 1H).

To a mixture of phosphorus oxychloride (20 ml) and acetonitrile (40 ml) heated at reflux was added a solution of n-butyl 6-oxo-1,6-dihydropyridazine-3-carboxylate (20 g) in acetonitrile (80 ml). The reaction was heated at reflux for 30 minutes, cooled and added to an ice cooled solution of $K_2CO_3$ (87.8 g) in water (600 ml) with vigorous stirring. The product was filtered off, washed with water and dried at 60° C. to give n-butyl 6-chloropyridazine-3-carboxylate (17.5 g, 80% yield), mpt 110°–111° C.

$^1$H-NMR ($CDCl_3$): δ0.99 (t, 3H, J=7.5 Hz), 1.48 (sextet, 2H, J=7.5 Hz), 1.84 (m, 2H), 4.49 (t, 2H, J=6.5 Hz), 7.71 (d, 1H, J=8.3 Hz), 8.18 (d, 1H, J=8.3 Hz).

Excess gaseous ammonia was added to an ice bath cooled solution of n-butyl 6-chloropyridazine-3-carboxylate (40 g) in methanol (280 ml). The mixture was stirred at ambient temperature for 4 hours and the resulting residue filtered off, washed with methanol (20 ml) and dried to give 6-chloropyridazine-3-carboxamide (28.05 g, 95.5% yield), mpt. 243°–5° C.

$^1$H-NMR ($d_6$-DMSO): δ7.96 (broad, 1H), 8.07 (d, 1H, J=8.3 Hz), 8.22 (d, 1H, J=8.3 Hz), 8.52 (broad s, 1H).

Benzyl bromide (71.4 ml) was added dropwise to a mixture of 5-bromo-2-hydroxybenzaldehyde (100.5 g) and $K_2CO_3$ (207.5 g) in 1-methyl-2-pyrrolidinone (500 ml) at 30° C. over 1 hour. The mixture was stirred for 3 hours at 35°–40° C. A solution of ethylamine hydrochloride (57.1 g) in methanol (250 ml) was added over 30 minutes at 35° C. and the mixture stirred for 3 hours at 35°–40° C. A solution of sodium borohydride (26.5 g) in 1-methyl-2-pyrrolidinone (300 ml) was added over 2 hours at 35°–40° C. and the mixture stirred at 40°–45° C. for 2 hours. The mixture was cooled (10° C.), diluted with ethyl acetate (200 ml) and acidified with 2N HCl (3,500 ml). The resulting precipitate was filtered off, washed with toluene and 40–60 petroleum ether and dried under vacuum at 60° C. The residue was purified by stirring in a mixture of acetonitrile (140 ml) and toluene (700 ml) at 80° C. for 30 minutes, cooling to 10° C. and filtering off the product to give N-ethyl N-(2-benzyloxy-5-bromobenzyl)amine hydrochloride salt (13.6 g, 76.7% yield).

$^1$H-NMR ($d_6$-DMSO): δ1.20 (t, 3H, J=7.3 Hz), 2.97 (q, 2H, J=7.3 Hz), 4.13 (s, 2H), 5.20 (s, 2H), 7.15 (d, 1H, J=8.3 Hz), 7.22–7.60 (m, 6H), 7.70 (d, 1H, J=2.5 Hz), 8.68 (broad s, 1H).

A mixture of N-ethyl-N-(2-benzyloxy-5-bromobenzyl) amine hydrochloride salt (87 g), 6-chloropyridazine-3-carboxamide (35 g) and $NaHCO_3$ (41 g) in 1-methyl-2-pyrrolidinone was heated at 115° C. for 24 hours, cooled to 20° C. and added to water (1100 ml) with vigorous stirring, maintaining the temperature below 30° C. with external cooling. Ethyl acetate (725 ml) was added and the mixture stirred at 20° C. for 2 hours. The precipitate was filtered, dried, washed with 40–60 petroleum ether and dried under vacuum at 65° C. to give 6-[N-(2-benzyloxy-5-bromobenzyl)-N-ethylamino]pyridazine-3-carboxamide (83 g, 84.7% yield), mpt. 171°–172° C.

$^1$H-NMR ($d_6$-DMSO): δ1.12 (t, 3H, J=7.0 Hz), 3.66 (q, 2H, J=7.0 Hz), 3.66 (q, 2H, J=7.0 Hz), 4.85 (s, 2H), 5.19 (s, 2H), 7.07–7.16 (m, 3H), 7.30–7.51 (m, 7H), 7.79 (d, 1H, J=9 Hz), 8.10 (broad s, 1H).

EXAMPLE 16

To a solution of 2-(N-(2-benzyloxy-5-bromobenzyl)-N-ethylamino]pyridine-5-carboxylic acid (0.89 g) in dichloromethane (50 ml) was added propanesulphonamide (0.3 g), dimethylaminopyrimidine (0.493 g) and 1-(3-dimethylaminopropyl)ethylcarbodiimide hydrochloride (0.58 g). The mixture was stirred at ambient temperature for 18 hours, and poured into 2N HCl. The organic layer was separated and washed with water and brine, then dried ($MgSO_4$), filtered and evaporated. The resulting oil was purified by chromatography on silica gel (eluting with 5% ethylacetate/dichloromethane to give N-(2-[N-(2-benzyloxy-5-bromobenzyl)-N-ethylamino]pyridine-5-carbonyl)propanesulphonamide (271 mg) as a white foam.

EXAMPLE 17

The compounds listed in Table 5b were prepared using a similar method to that described in Example 16 using the appropriate sulphonamide as starting material.

EXAMPLE 18

N-Methyl-N-propyl 2-[N-(2-benzyloxy-5-bromobenzyl)-N-ethylamino]pyridine-5-carboxamide was prepared from N-propyl 2-[N-(2-benzyloxy-5-bromobenzyl)-N-ethylamino]pyridine-5-carboxamide using a similar method to that of Reference Example 5 and obtained as a gum.

MS (FAB)+: 496(MH)$^+$ $^1$H NMR (DMSO-$d_6$): δ0.80 (t, 3H, J=6.7 Hz); 1.10 (t, 3H, J=6.7 Hz); 1.56 (sextet, 2H, J=6.7 Hz); 2.93 (s, 3H); 3.31 (m, 2H), 3.58 (q, 2H, J=6.7 Hz); 4.72 (s, 2H); 5.19 (s, 2H); 6.57 (d, 1H, J=9.3 Hz); 7.07 (d, 1H, J=3.0 Hz); 7.10 (d, 1H, J=9.3 Hz); 7.29–7.56 (m, 7H); 8.15 (d, 1H, J=1.7 Hz).

EXAMPLE 19

N-(1-(Methoxycarbonyl)-2-hydroxyethyl)-2-[N-(2-benzyloxy-5-bromobenzyl)-N-ethylamino]pyridine-5-carboxamide was prepared from 2-[N-(2-benzyloxy-5-bromobenzyl)-N-ethylamino]pyridine-5-carboxylic acid using a similar method to that described in the first paragraph of Reference example 27 (except methyl 2-iodo-3-hydroxypropanoate was used instead of ethyl iodide) and was obtained as a gum.

MS (FAB$^+$): 542 (MH)$^+$ $^1$H NMR (DMSO-$d_6$) δ1.10 (t, 3H, J=6.7 Hz); 3.59 (m, 2H); 3.63 (s, 3H); 3.76 (t, 2H, J=6.0 Hz); 4.50 (qd, 1H, J=8.0 Hz); 4.77 (s, 2H), 4.99 (t, 1H, J=6.0 Hz), 5.19 (s, 2H); 6.62 (d, 1H, J=9.3 Hz); 7.04 (d, 1H, J=2.7 Hz); 7.09 (d, 1H, J=8.3 Hz); 7.29–7.51 (m, 6H); 7.93 (dd, 1H, J=9.3, 3.0 Hz); 8.28 (d, 1H, J=6.3 Hz); 8.60 (d, 1H, J=3.0 Hz).

EXAMPLE 20

N-(1-Methoxycarbonylbutyl)-2-[N-(2-benzyloxy-5-bromobenzyl)-N-ethylamino]pyridine-5-carboxamide was prepared using a similar method to that of Example 19, except methyl 2-iodopentanoate was used instead of methyl 2-iodo-3-hydroxypropanoate (mp 54°–55° C.).

EXAMPLE 21

N-(1-Carboxy-2-hydroxyethyl)-2-[N-(2-benzyloxy-5-bromo-benzyl)-N-ethylamino]pyridine-5-carboxamide was prepared from N-(1-(methoxycarbonyl)-2-hydroxyethyl)-2-[N-(2-benzyloxy-5-bromobenzyl)-N-ethylamino]pyridine-5-carboxamide using a similar method to that described in Example 1, except the product was extracted with ethyl acetate and purified by trituration in hexane (mp 162.0°–168.5° C.).

MS (FAB$^+$) : 528 (MH)$^+$ $^1$H NMR (DMSO-d$_6$): δ1.09 (t, 3H, J=6.7 Hz); 3.62 (q, 2H, J=6.7 Hz); 3.80 (d, 2H, J=5.0 Hz); 4.45 (q, 1H, J=5.0 Hz); 4.81 (s, 2H); 5.13 (s, 2H); 6.94 (d, 1H, J=9.7 Hz); 7.12 (d, 1H, J=9.3 Hz); 7.25–7.50 (m, 7H); 8.11 (dd, 1H, J=9.7, 2.7 Hz); 8.48 (d, 1H, J=2.7 Hz); 8.56 (d, 1H, J=6.7 Hz).

EXAMPLE 22

N-(1-carboxybutyl)-2-[N-(2-benzyloxy-5-bromobenzyl)-N-ethylamino]pyridine-5-carboxamide was prepared using a similar method to that of Example 20 (mp 98°–115° C.).

MS (FAB$^+$): 540 (MH)$^+$ $^1$H NMR (DMSO-d$_6$): δ0.89 (t, 3H, J=7.9 Hz); 1.10 (t, 3H, J=7.9 Hz); 1.38 (Septet, 2H, J=7.9 Hz); 1.75 (q, 2H, J=7.9 Hz); 3.60 (q, 2H, J=7.9 Hz); 4.34 (q, 1H, J=7.9 Hz); 4.75 (s, 2H), 5.18 (s, 2H); 6.66 (d, 1H, J=8.3 Hz); 7.08 (d, 1H, J=2.1 Hz); 7.09 (d, 1H, J=8.3 Hz); 7.30–7.49 (m, 6H); 7.94 (dd, 1H, J=8.3, 2.1 Hz); 8.29 (d, 1H, J=7.9 Hz); 8.58 (d, 1H, J=2.1 Hz); 12.41 (bs, 1H)

EXAMPLE 23

2-[N-(2-Benzyloxy-5-bromobenzyl)-N-(cyclopropylmethyl)amino]pyridine-5-carboxylic acid was prepared from ethyl 2-[N-(2-benzyloxy-5-bromobenzyl)-N-(cyclopropylmethyl)amino]pyridine-5-carboxylate using a similar method to that of Example 1 except the product was extracted with ethyl acetate and purified by trituration in hexane (mp 212.5°–213.0° C.).

Ethyl 2-[N-(2-benzyloxy-5-bromobenzyl)-N-(cyclopropyl-methyl)amino]pyridine-5-carboxylate was prepared from ethyl 2-[N-(2-benzyloxy-5-bromobenzyl) amino]pyridine-5-carboxylate and cyclopropylmethyl bromide by a similar method to that described in Reference example 5, purifying the product by MPLC and eluting with 80% dichloromethane in hexane.

EXAMPLE 24

6-[N-Allyl-N-(2-benzyloxy-5-bromobenzyl)amino]pyridazine-3-carboxylic acid was prepared from butyl 6-[N-allyl-N-(2-benzyloxy-5-bromobenzyl)amino]pyridazine-3-carboxylate using a similar method to that described in Example 1, except that the product was extracted with dichloromethane and purified by crystallisation from dichloromethane/hexane. (mp 135°–136° C.).

The starting material was prepared as follows:

Butyl 6-[N-(2-benzyloxy-5-bromobenzyl)amino]pyridazine-3-carboxylate was prepared as its trifluoroacetic acid salt from butyl 6-chloropyridazine-3-carboxylate using a similar method to that described in Reference example 23 for the preparation of ethyl 6-[N-(2-benzyloxy-5-bromobenzyl)amine]pyridazine-3-carboxylate except the product was purified by formation of its trifluoroacetic acid salt and it was crystallised from diethyl ether. (mp 133°–135° C.).

To a mixture of butyl 6-[N-(2-benzyloxy-5-bromobenzyl)amino]pyridazine-3-carboxylate (CF3CO$_2$H salt) (1.2 g) in THF (100 ml) under argon, was added potassium di-(trimethylsilyl)amide [7.0 ml of 0.67M solution in toluene] to give a yellow solution. To the solution was added allyl bromide (0.5 ml). The mixture was stirred for 2 hours, poured into water and extracted with diethyl ether. The organic solution was dried (MgSO$_4$), evaporated and the residue purified by HPLC, eluting with dichloromethane, to give butyl 6-[N-allyl-N-(2-benzyloxy-5-bromobenzyl)amino]pyridazine-3-carboxylate (460 mg) as a gum.

EXAMPLE 25

A mixture of ethyl [6-[N-(2-benzyloxy-5-bromobenzyl)-N-ethylamino]pyridazin-3-ylcarbonyl]acetate (600 mg), and hydrazine hydrate (0.1 ml) in ethanol (50 ml) was heated at reflux for 2 hours, cooled and acidified to pH 3 with 1N HCl. The mixture was diluted dropwise with water until a precipitate formed which was filtered off to give 3-[6-(N-(2-benzyloxy-5-bromobenzyl)-N-ethylamino)pyridazin-3-yl]-5-hydroxypyrrazole (400 mg) (mp 132° C.).

The starting material was prepared as follows:

A mixture of 6-[N-(2-benzyloxy-5-bromobenzyl)-N-ethylamino]pyridazine-3-carboxylic acid (12.5 g) and carbonyl di-imidazole (6.0 g) was heated at 5° C. for 1 hour. Separately, a mixture of potassium ethyl malonate (7.0 g), triethylamine (8.0 ml) and anhydrous magnesium chloride (5.0 g) in acetonitrile (200 ml) was stirred at ambient temperature for 2 hours. The two mixtures were combined and stirred for 18 hours at ambient temperature, then at reflux for 1 hour. The solvents were evaporated, and the residue partitioned between dichloromethane and 2N HCl. The organic solution was dried (MgSO$_4$) and evaporated. The resulting residue was purified by flash chromatography, eluting with diethyl ether, to give ethyl [6-[N-(2-benzyloxy-5-bromobenzyl)-N-ethylamino]pyridazin-3-ylcarbonyl]acetate (12.5 g) as a yellow gum.

EXAMPLE 26

N-(Tetrazol-5-ylmethyl)-2-[N-(2-benzyloxy-5-bromobenzyl)-N-ethylamino]thiazole-5-carboxamide was prepared from N-cyanomethyl-2-[N-(2-benzyloxy-5-bromobenzyl)-N-ethylamino]thiazole-5-carboxamide using a method similar to that described in Example 11, except that triethylammonium chloride was used in place of ammonium chloride and the product was purified by HPLC eluting with mixtures of methanol and dichloromethane (5:95, 10:90): (mp 232°–236° C.).

For starting material see Table 2b Compound 10.

EXAMPLE 27

6-[N-(2-Benzyloxy-5-bromobenyl)-N-ethylamino]-2-oxo-1,2-dihydropyridine-3-carboxylic acid was prepared from tert-butyl 6-[N-(2-benzyloxy-5-bromobenzyl)-N-ethylamino]-2-oxo-1,2-dihydro pyridine-3-carboxylate by a similar method to that described in Example 3, except that the reaction was carried out at ambient temperature for 1 hour and the product was purified by recrystallisation from acetonitrile (mp 163°–165° C.).

The starting material was prepared as follows:

A mixture of 2-benzyloxy-5-bromobenzaldehyde (20 g) and hydroxylamine hydrochloride (9.55 g) in pyridine (50 ml) was heated at 75° C. for 45 minutes. The solvent was evaporated and the residue purified by chromatography, eluting with dichloromethane, to give 2-benzyloxy-5-bromobenzaldehyde oxime (30 g) (mp 132°–134° C.).

A mixture of 2-benzyloxy-5-bromobenzaldehyde oxime (10 g) in diethyl ether (150 ml) was added dropwise to a suspension of lithium aluminium hydride (2.73 g) in diethyl ether (200 ml) under argon at about 10° C. The resulting mixture was heated at reflux for 1.5 hours, quenched with a mixture of water (2.7 ml) and THF (10 ml) at 10° C., then with 15% aqueous sodium hydroxide (2.7 ml) and water (8.2 ml). The resulting mixture was dried ($Na_2SO_4$) and filtered. HCl gas was bubbled through the filtrate at 10° C. The resulting white precipitate was filtered off, washed with diethyl ether and dried to give 2-benzyloxy-5-bromobenzylamine hydrochloride (10.27 g) (mp 155°–158° C.).

To a mixture of 2-benzyloxy-5-bromobenzylamino hydrochloride (10 g) in toluene (75 ml) at 4° C. was added a solution of trimethylaluminium in toluene (2M, 15.2 ml). The mixture was stirred at ambient temperature for 2 hours, acetonitrile (6.5 ml) added and the mixture heated at 80° C. for 18 hours. The mixture was cooled and poured onto a slurry of silica gel (300 g), and dichloromethane. The solvent was filtered off and the product eluted from the silica gel with methanol to give $N^1$-[2-benzyloxy-5-bromobenzyl] acetamidine (5.51 g).

To a mixture of NaH (50% suspension in oil, 0.68 g) in ethanol (50 ml) at 4° C. was added $N^1$-[2-benzyloxy-5-bromobenzyl]acetamidine (5.0 g) and dimethyl methoxymethylene malonate (2.4 g). The mixture was stirred at ambient temperature for 18 hours and heated at reflux for 3 hours. The solvent was evaporated, the residue dissolved in dichloromethane and washed with saturated aqueous ammonium chloride. The organic solution was dried ($Na_2SO_4$) and purified by chromatography eluting with methanol/dichloromethane mixtures (0:100, 0.5:99.5, 1:99, 1.5:98.5, 2:98) to give ethyl 6-[2-benzyloxy-5-bromobenzylamino]-2-oxo-1,2-dihydropyridine-3-carboxylate (2.78 g).

A mixture of ethyl 6-[2-benzyloxy-5-bromobenzylamino]-2-oxo-1,2-dihydropyridine-3-carboxylate (2.78 g), sodium carbonate (0.97 g) and allyl bromide (0.77 ml) in DMF (10 ml) was stirred for 5 days, poured into saturated aqueous ammonium chloride solution and extracted with ethyl acetate. The organic solution was washed with HCl solution, saturated aqueous sodium hydrogen carbonate and brine, dried ($Na_2SO_4$), filtered and evaporated. The residue was purified by chromatography, eluting with 2.5% ethyl acetate/dichloromethane, to give ethyl 6-[2-benzyloxy-5-bromobenzylamino]-2-allyloxypyridine-3-carboxylate (1.99 g) as an oil.

A solution of ethyl 6-[2-benzyloxy-5-bromobenzylamino]-2-allyloxypyridine-3-carboxylate (1.99 g) in DMF (25 ml) was added to a mixture of sodium hydride (o.19 g, 50% suspension in oil) in DMF (10 ml) at −5° C. After 15 minutes, a solution of iodoethane (0.32 ml) in DMF (10 ml) was added dropwise at −5° C. The mixture was stirred at ambient temperature for 1 hour, poured into saturated aqueous $NH_4Cl$ and extracted with ethyl acetate. The organic solution was washed with HCl, saturated aqueous sodium hydrogen carbonate and brine, dried ($Na_2SO_4$), filtered and evaporated. The residue was purified by filtration through silica gel to give ethyl 6-[N-(2-benzyloxy-5-bromobenzylamino)-N-ethylamino]-2-allyloxypyridine (2.07 g).

A mixture of ethyl 6-[N-(2-benzyloxy-5-bromobenzylamino)-N-ethylamino]-2-allyloxypyridine-3-carboxylate (2.0 g), n-butanol (30 ml) and sodium hydroxide (0.8 g) was heated at reflux for 30 minutes. The solvent was evaporated, the residue dissolved in a mixture of water and methanol and filtered through Celite. The filtrate was acidified with acetic acid to pH5 to give a white emulsion. The mixture was extracted with ethyl acetate, the organic solution washed (brine), dried ($Na_2SO_4$), filtered and evaporated. The resulting gum was crystallised from acetonitrile to give 6-[N-(2-benzyloxy-5-bromobenzyl)-N-ethylamino]-2-allyloxypyridine-3-carboxylic acid (mp 129°–131° C.).

To a solution of 6-[N-(2-benzyloxy-5-bromobenzyl)-N-ethylamino]-2-allyloxypyridine-3-carboxylic acid (0.6 g) in toluene (9 ml) at 80° C. was added N,N-dimethylformamide di-t-butyl acetal (1.1 ml) in toluene (4 ml). The mixture was heated at 80° C. for 2 hours, mixed with ethyl acetate and washed with aqueous sodium hydrogen carbonate solution and brine. The organic solution was dried ($Na_2SO_4$), filtered and evaporated. The residue was purified by chromatography eluting with 1% ethyl acetate/dichloromethane to give tert-butyl 6-[N-(2-benzyloxy-5-bromobenzyl)-N-ethylamino]-2-allyloxypyridine-3-carboxylate as an oil.

Argon was bubbled through a mixture of tert-butyl 6-[N-(2-benzyloxy-5-bromobenzyl)-N-ethylamino]-2-allyloxypyridine-3-carboxylate (0.53 g), 2,2-dimethyl-1,3-dioxane-4,6-dione (0.28 g) and tetrakis(triphenylphosphine) palladium (0.11 g) in DMF (5 ml) for 1 hour in the dark. The mixture was poured into saturated aqueous ammonium chloride and extracted with ethyl acetate. The organic solution was washed (hydrochloric acid, ammonium chloride solutions), dried ($Na_2SO_4$), filtered and evaporated. The residue was purified by chromatography, eluting with 2% methanol/dichloromethane and a few drops of glacial acetic acid, to give tert-butyl 6-[N-(2-benzyloxy-5-bromobenzyl)-N-ethylamino]-2-oxo-1,2-dihydropyridine-3-carboxylate (0–47 g) as an oil.

EXAMPLE 28 n-Butyl 6-[N-(1-(2-benzyloxy-5-bromophenyl)-eth-1-yl)-N-ethylamino]pyridazine-3-carboxylate (180mg) was dissolved in THF (5 mL) and methanol (5 mL) and sodium hydroxide solution added (0.61 mL, 2M). The mixture was stirred for one hour at ambient temperature, and then the solvents evaporated off. The resulting foam was dissolved in water (20 mL) and pH adjusted to pH 4–5 with glacial acetic acid. A white precipitate formed which was filtered off, washed with water and dried for 17 hours at 5° C. to give 6-[N-(1-(2-benzyloxy-5-bromophenyl)eth-1-yl)-N-ethylamino]pyridazine-3-carboxylic acid (134 mg, mp 129.2° C.).

$^1$H NMR (DMSO-$d_6$): δ0.80 (t, 3H, J=4.8 Hz), 1.6 (d, 3H, J=2.5 Hz), 3.4 (q, 2H, J=4.8 Hz), 4.95 (d, 1H, J=8.4 Hz), 5.05 (d, 1H, J=8.4 Hz), 6.0 (m, 1H), 7.0 (d, 1H, J=7.2 Hz), 7.2 (m, 6H), 7.5 (m, 2H), 7.6 (d, 1H, J=6.7 Hz)

MS: 456 (M+H$^+$), 480 (M+Na$^+$).

Analysis $C_{22}H_{22}BrN_3O_3$: theory: C: 57.9; H: 4.86; N: 9.21. Found: C: 57.4; H: 4.8; N: 9.0.

The starting material was prepared as follows:

2-Benzyloxy-5-bromobenzaldehyde (5 g) was dissolved in anhydrous diethyl ether (20 mL) and THF (20 mL) and stirred at ambient temperature under argon while a solution of methyl magnesium bromide in ether (7.4 mL, 3M solution in ether) was added dropwise over 5 minutes. A white precipitate formed. After 30 minutes the mixture was poured onto a mixture of ice and water (300 mL). The aqueous mixture was extracted with ethyl acetate (3×250 mL), the organic extracts were washed with brine (100 mL) and dried (MgSO$_4$). After removal of the solvent the residual pale yellow oil was purified by MPLC (eluting with dichloromethane on silica) to give 1-(2-benzyloxy-5-bromophenyl)-ethanol, (5.19 g, mp 76.7° C.).

Elemental Analysis C$_{15}$H$_{15}$BrO$_2$: theory: C: 58.7; H: 4.92; N: 0. Found: C: 58.7; H: 4.8; N: 0.

1-(2-Benzyloxy-5-bromophenyl)-ethanol (3.74 g) was dissolved in pyridine (15 mL) and cooled to −10° C. under argon. Mesyl chloride (0.95 mL) was added dropwise over ten minutes and the mixture stirred allowing to come to ambient temperature over seventeen hours. The mixture was diluted with ethyl acetate (100 mL) and then washed with hydrochloric acid (1M, 3×70 mL) until the organic phase tested to pH 1. The ethyl acetate fraction was then washed with saturated sodium hydrogen carbonate solution (50 mL) and dried (MgSO$_4$). After removal of solvent the oily residue was purified by MPLC (eluting 75% dichloromethane, 25% hexane, silica) to give 1-(2-benzyloxy-5-bromophenyl) ethanol methanesulphonate which was used rapidly without further purification, yield 1.19 g.

n-Butyl 6-(2-aminoethyl)-3-pyridazine carboxylate (500 mg) was dissolved in dry DMF (15 mL) and added to a suspension of sodium hydride (90 mg of a 60% dispersion in mineral oil) under argon dropwise over ten minutes. After stirring for one hour at ambient temperature, a solution of 1-(2-benzyloxy-5-bromophenyl)-ethanol methanesulphonate (1.18 g) in DMF (5 mL) was added, and the mixture stirred for 16 hours. The solution was poured into water (200 mL) and the mixture made acidic with glacial acetic acid. The organic phase was then extracted with ethyl acetate (3×250 mL), washed with water (100 mL) and brine (100 mL) and dried (MgSO$_4$). After removal of the solvent, the residue was purified by MPLC (eluting 5 to 40% ethyl acetate in dichloromethane, silica) to give a gum, n-butyl 6-[N-1-(2-benzyloxy-5-bromophenyl)-ethyl]-N-(ethyl) amino-3-pyridazine carboxylate. (190 mg)

$^1$H NMR (DMSO-d$_6$): δ0.85 (t, 3H, J=3.6 Hz), 1.5 (q, 2H, J=4.2 Hz), 1.6 (d, 3H, J=3.6 Hz), 1.75 (m, 2H), 3.4(q, 2H, J=4 Hz), 4.3 (t, 2H, J=3.6 Hz), 6.05 (m, 1H), 7.0 (d, 1H, J=6 Hz), 7.2 (m, 6H,) 7.5 (m, 3H).

EXAMPLE 29

Methyl 4-[N-(1-(2-benzyloxy-5-bromophenyl)eth-1-yl)-N-ethylamino]benzoate (410 g) was dissolved in THF (7 mL) and methanol (7 mL) and sodium hydroxide solution added (1.4 mL, 2M). The mixture was stirred for two days at ambient temperature, heated to 60° C. for one hour, and then the solvents evaporated off. The resulting foam was dissolved in water (25 mL) and pH adjusted to pH 2–3 with glacial acetic acid. A white precipitate formed which was filtered off, washed with water and dried for 17 hours at 45° C. to give methyl 4-[N-(1-(2-benzyloxy-5-bromophenyl) eth-1-yl)-N-ethylamino]benzoate acid (320 mg, mp 173° C. (dec).

1H NMR (DMSO-d$_6$): δ0.9 (t, 3H, J=3.2 Hz), 1.5 (d, 3H, J=4.8 Hz), 5.1 (s, 2H), 5.4 (q, 1H, J=4.8 Hz), 6.7 (d, 1H, J=6 Hz), 7.1 (d, 1H, J=7 Hz), 7.3 (m, 5H), 7.4 (m, 2H,), 7.7 (d, 2H, J=6 Hz).

MS: 454 (M+H$^+$), 476 (M+Na$^+$).

Analysis C$_{22}$H$_{22}$ BrN$_3$O$_3$.0.25H$_2$O: theory: C: 62.8; H: 5.34; N: 3.05. Found: C: 62.5; H: 5.2; N: 2.9.

The starting material was prepared as follows:

1-(2-Benzyloxy-5-bromophenyl)-ethanol (3.69 g) was dissolved in dichloromethane (80 mL) and cooled to 0° C. under argon. Triphenyl phosphine 93.47 g) was added followed by carbon tetrabromide (7.36 g) and stirred for eighteen hours, allowing to warm to ambient temperature. After removal of solvent the residue was purified by MPLC (eluting 50% dichloromethane, 50% hexane, silica) to give 1-(2-benzyloxy-5-bromophenyl)ethyl bromide (2.9 g) which was used immediately without further purification.

Methyl 4-(ethylamino)benzoate (1.67 g) was dissolved in dry DMF (15 mL), cooled to 0° C. under argon, sodium hydride (373 mg of a 60% dispersion in mineral oil) was added and then the cooling bath removed. After stirring for one hour at ambient temperature, the solution was recooled to 0° C., and a solution of 1-(2-benzyloxy-5-bromophenyl) eth-1-yl bromide (2.9 g) in DMF (15 mL) was added, and the mixture stirred for 16 hours allowing to warm to ambient temperature. The solution was poured into water (200 mL) and the mixture made acidic with glacial acetic acid. The organic phase was then extracted with ethyl acetate (3×250 mL), washed with water (100 mL) and brine (100 mL) and dried (MgSO$_4$). After removal of the solvent, the residue was purified by MPLC (eluting 75% dichloromethane, hexane in dichloromethane, silica) to give a waxy solid, methyl 4-[N-(1-(2-benzyloxy-5-bromophenyl)eth-1-yl)-N-ethylamino]benzoate (420 mg).

$^1$H NMR (DMSO-d$_6$): d 0.8 (t, 3H, J=4.8 Hz), 1.55 (d, 3H, J=4.8 Hz), 3.4(q, 2H, J=4.9 Hz), 3.8 (s, 3H, ), 5.1 (s, 2H), 5.4 (q, 1H, J=5.2 Hz), 6.7 (d, 1H, J=6.7 Hz), 7.3(m, 5H), 7.4(m, 2H,), 7.7(m, 2H,).

MS: 468, (M+H$^+$)

EXAMPLE 30

Ethyl 4-(1-(2-benzyloxypyrazin-3-yl)prop-1-ylamino) benzoate (229 mg) was dissolved in THF (7 mL) and methanol (7 mL) and sodium hydroxide solution added (1.5 mL, 2M). The mixture was stirred for seventeen hours at ambient temperature, then heated at reflux for 2 hours, allowed to cool to ambient temperature and then the solvents evaporated off. The resulting foam was dissolved in water (25 mL) and extracted with ethyl acetate (2×20 mL) the aqueous phase was then adjusted to pH 4–5 with glacial acetic acid and re-extracted with ethyl acetate (2×20 mL). The combined organic phases were dried over magnesium sulphate. After removal of solvents, the residue was purified by MPLC (1% acetic acid, 24% ethyl acetate in hexane, silica)to give a yellow gum which was further purified by crystallisation from the above eluent system to give 4-(1-(2-benzyloxypyrazin-3-yl)prop-1-ylamino benzoic acid (138 mg, mp 141.5° C.).

$^1$H NMR (DMSO-d$_6$): δ0.9 (t, 3H, J=Hz), 1.9 (m, 2H), 4.8 (t, 1H, J=Hz), 5.5 (d, 2H, J=Hz), 6.5 (d, 2H, J=Hz), 6.8 (bs, 1H, NH), 7.5 (m, 7H), 7.4 (m, 7H), 8.1 (m, 2H).

MS: 363 (M+H$^+$)

Analysis C$_{21}$H$_{21}$N$_3$O$_3$: theory: C: 69.4; H: 5.82; N: 11.6. Found: C: 65.0; H: 5.5; N: 10.8.

Alanine amide hydrobromide (55.69 g) was dissolved in methanol (670 mL) and water (67 mL), cooled to −40° C. and glyoxyl (50 mL, 40% aqueous solution) added rapidly. This mixture was maintained at −30° C. and stirred vigorously, while aqueous sodium hydroxide solution (76.6 mL, 10.8M) was added dropwise over twenty minutes. The mixture was maintained at −30° C. for thirty minutes after addition of the sodium hydroxide solution was complete, and then allowed to warm to ambient temperature over seventeen hours. The reaction mixture was cooled to 0° C. and concentrated hydrochloric acid (82 mL) added cautiously. Solid sodium bicarbonate (66.3 g) was then added portion wise (CAUTION: vigorous effervescence). The mixture was allowed to warm to ambient temperature, solids filtered off, water was added to the filtrate (67 mL) and the solution evaporated to dryness. The residue was redissolved in water (150 mL) and solid sodium hydrogen carbonate added until the solution was at pH 8. Dichloromethane (1 L) was added and the mixture stirred for seventeen hours. The organic phase was separated off and dried ($MgSO_4$). Removal of the solvents and recrystallisation (ethyl acetate) of the solid gave the 2-hydroxy-3-methylpyrazine, yield 14.96 g, mp 154.1° C.

Analysis $C_5H_6N_2O$: theory: C: 54.5; H: 5.49; N: 25.4. Found: C: 54.5; H: 5.5; N: 25.5.

2-Hydroxy-3-methylpyrazine (14.94 g) was added to phosphorus oxychloride (55 mL) containing three drops of concentrated sulphuric acid and heated under reflux for one hour. The solution was allowed to cool to ambient temperature and then poured onto ice (600 g) and ether (300 mL). The mixture was stirred to effect hydrolysis of excess phosphorus oxychloride. Concentrated ammonia was added to adjust the pH of the mixture to 8, keeping the temperature below 10° C., the pH was then adjusted to 11 with sodium hydroxide (2M) and extracted with ether (3×300 mL). The combined organic extracts were dried ($MgSO_4$). After removal of solvents, the residue was purified by MPLC (dichloromethane, silica) to give 2-chloro-3-methylpyrazine, (7.67 g).

1H NMR (DMSO-$d_6$): δ2.6 (s, 3H), 8.4 (d, 1H, J=2 Hz), 8.55 (d, 1H, J=2 Hz).

MS: 129 (M+H$^+$)

Sodium hydride (2.38 g of a 60% dispersion in mineral oil) was washed twice with dry THF and dried under a stream of dry argon, it was then suspended in dry THF (70 mL), and stirred under argon while benzyl alcohol (6.43 g) was added dropwise over ten minutes. After addition was complete the solution was stirred for a further thirty minutes and then a solution of 2-chloro-3-methylpyrazine, (7.65 g) in THF (90 mL) was added. The mixture was heated under reflux for three and a half hours, then allowed to cool over seventeen hours, poured into a mixture of ice and water (500 mL) and dried ($MgSO_4$). After removal of the solvents, the residue was purified by MPLC (15% ethyl acetate, hexane) to give 2-benzyloxy-3-methylpyrazine, yield, 10.43 g.

$^1$H NMR (DMSO-$d_6$): δ2.45 (s, 3H), 5.4 (s, 2H), 7.4 (m, 5H), 8.05 (m, 2H).

MS: 201 (M+H$^+$)

2-Benzyloxy-3-methylpyrazine (600 mg) was dissolved in 1,4-dioxane (12 mL), selenium dioxide (1 g) and water added (one drop) and the mixture heated at reflux for seventeen hours. The reaction mixture was allowed to cool to ambient temperature, filtered and the solvents removed. The residue was dissolved in water (30 mL), neutralised with aqueous sodium hydrogen carbonate solution (10%) and extracted with dichloromethane (3×40 mL), the organic phase was dried ($MgSO_4$). After removal of the solvents the oil was purified by MPLC (15%ethyl acetate, hexane, silica) to give 2-benzyloxypyrazine-3-aldehyde (460 mg, mp 69.4° C.).

$^1$H NMR (DMSO-$d_6$): δ5.6 (s, 2H), 7.4 (m, 3H), 7.55 (m, 2H), 8.5 (d, 1H, J=2 Hz), 8.6 (d, 1H, J=2 Hz), 10.15 (s, 1H).

2-Benzyloxypyrazine-3-aldehyde (455 mg) was mixed with ethyl-4-aminobenzoate (321 mg) and stirred at 120° C. for 1 hour. The solid was then azeotroped with toluene (20 mL) to remove the last traces of water. The residue was dissolved in ethanol (10 mL) under argon, and sodium borohydride (81 mg) added with stirring at ambient temperature. The mixture was then heated to reflux for one hour, and allowed to cool to ambient temperature over 16 hours. Water (70 mL) was added, and the mixture acidified to pH 3 with acetic acid and then extracted with ethyl acetate (4×10 mL), washed with water (50 mL), brine (50 mL) and dried over magnesium sulphate. The residue was purified by MPLC (3% ethyl acetate in dichloromethane, silica) to give ethyl 4-[2-benzyloxypyrazin-3-ylmethylamino]benzoate yield, 460 mg, mp 111.7° C.

$^1$H NMR (DMSO-$d_6$): δ1.25 (t, 3H, J=4 Hz), 4.2 (q, 2H, J=4 Hz), 4.5 (s, 2H), 5.5 (s, 2H), 6.7 (m, 2H), 7.0 (bs, 1H,), 7.4 (m, 3H), 7.5 (m, 2H), 7.7 (m, 2H), 8.2 (m, 2H).

Ethyl 4-(2-benzyloxypyrazin-3-ylmethylamino)benzoate (455 mg) was dissolved in dry DMF (4 mL) and added to a suspension of sodium hydride (51 mg of a 60% dispersion in mineral oil) in DMF (4 mL) precooled to 0° C. under argon dropwise over fifteen minutes. After stirring for thirty minutes at 0° C. ethyl iodide (0.12 mL) was added and the mixture stirred for 36 hours. The solution was poured into water (50 mL) and the mixture made acidic with glacial acetic acid. The organic phase was then extracted with ethyl acetate (3×50 mL), washed with water (50 mL) and brine (50 mL) and dried ($MgSO_4$). After removal of the solvent, the residue was purified by MPLC (eluting 20% ethyl acetate in hexane, silica) to give ethyl 4-(1-(2-benzyloxypyrazin-3-yl)prop-1-ylamino)benzoate as an oil which was used in the next step without further purification, (260 mg).

A small sample was further purified by trituration with hexane (×3) (mp 107° C.).

$^1$H NMR (DMSO-$d_6$): d 0.9 (t, 3H, J=3.2 Hz), 1.25 (t, 3H, J=3.3 Hz), 1.9 (m, 2H), 4.2 (q, 2H, J=4.9 Hz), 4.8 (q, 1H, J=5.2 Hz), 5.43 (d, 2H, J=7.2 Hz), 5.54 (d, 2H, J=6.2 Hz), 6.1 (m, 2H), 6.6 (bd, 1H, J=7.2 Hz, NH), 7.5 (m, 7H).

MS: 392 (M+H$^+$).

EXAMPLE 31

A solution of methyl 2-[N-(2-(2-thienylmethoxy)-5-bromobenzyl)-N-ethylamino]pyridine-5-carboxylate (0.53 g, 1.15 mmol) in methanol (25 mL) was treated with aqueous sodium hydroxide (2N, 5 mL). The reaction was heated to reflux for 9 hours. The reaction mixture was cooled and evaporated and residue was diluted with water and acidified with acetic acid. The off-white solid was filtered off to give 2-[N-(2-(2-thienylmethoxy)-5-bromobenzyl)-N-ethylamino]pyridine-5-carboxylic acid (0.41 g, 91%).

MS (FAB$^+$): (M+H)$^+$ 447.

Elemental Analysis for $C_{20}H_{16}BrN_2O_3S$: Calculated: % C, 53.7; H, 4.28; N, 6.26; Found: % C, 53.8; H, 4.6; N, 5.7.

$^1$H-NMR (200 MHz, DMSO-$d_6$) δ: 1.09 (t, J=7H , 3H); 3.56 (q, J=7 Hz, 2H); 4.7 (s, 2H); 5.38 (s, 2H); 6.59 (d, J=9 Hz, 1H); 7.04 (m, 2H); 7.2 (m, 2H), 7.43 (dd, J=2.5, 8 Hz, 1H); 7.56 (dd, J=1.4, 6 Hz; 1H); 7.88 (dd, 2.5, 11 Hz, 1H); 8.6 (d, J=2 Hz, 1H).

The starting material was prepared as follows:

Methyl 5-bromosalicylate [prepared by treating methyl 5-bromosalicyclic acid with methanol and sulphuric acid] (4.62 g, 20 mmol) was dissolved in THF (150 mL) and treated with thiophene methanol (2.28 g, 20 mmol) and triphenyl phosphine (10.4 g, 40 mmol). The reaction was cooled in an ice bath and treated with DEAD (6.96 g, 20 mmol). The resultant orange solution was allowed to stir at ambient temperature under argon for 18 hours. The reaction mixture was evaporated and the residue subjected to chromatography (eluant: diethyl ether/hexane) to give methyl 5-bromo-2-(2-thienylmethoxy)benzoate as a pink oil (3.6 g, 55%).

MS(EI$^+$): (M$^+$)326

$^1$H NMR (200 MHz, DMSO-d$_6$) δ: 3.79 (s, 3H); 5.38 (s, 2H); 7.02 (m, 1H); 7.22 (m, 2H); 7.55 (dd, J=1, 5 Hz, 1H); 7.69 (dd, J=2.5, 9 Hz, 1H); 7.76 (d, J=2.5, 1H).

A solution of methyl 5-bromo-2-(2-thienylmethoxy) benzoate (1.6 g, 4.9 mmol) in dichloromethane (20 ml) was cooled to −85° C. A solution of DIBAL (5.8 ml, 1N in CH$_2$Cl$_2$) was added dropwise. The temperature was maintained below −75° C. for 30 minutes and then warmed to −50° C. over 2½% hours. The reaction mixture was quenched with 1N HCl, washed with aqueous sodium hydrogen carbonate solution, dried (MgSO$_4$) and evaporated. The product was purified by chromatography (eluant: diethyl ether/hexane) to give 5-bromo-2-(2-thienylmethoxy) benzyl alcohol a colourless gum (0.53 g, 36.4%).

MS (EI$^+$): (M+) 298

$^1$H-NMR (200 MHz, DMSO-d$_6$) δ: 4.48 (d, J=3 Hz, 2H); 5.17 (bt, 1H); 5.32 (s, 2H); 7.05 (m, 2H); 7.2 (m, 1H); 7.38 (dd, J=3.8 Hz, 1H); 7.52 (m, 2H).

A solution of 5-bromo-2-(2-thienylmethoxy)benzyl alcohol (0.53 g, 1.77 mmoles) in dichloromethane (12 ml) was cooled in an ice bath and treated with carbon tetrabromide (0.73 g, 2.2 mmol) polymer bound triphenylphosphine (0.65 g, 1.95 mmol) and stirred at ambient temperature for 42 hours. The reaction was filtered and evaporated. Chromatography (eluant: ethyl acetate/hexane) gave 5-bromo-2-(2-thienylmethoxy)benzyl bromide as a white solid (0.29, 45%).

MS (EI$^+$): (M+) 360

$^1$H NMR (250 MHz, DMSO-d$_6$) δ: 4.6 (s, 2H); 5.4 (s, 2H); 7.05 (m, 1H); 7.15 (d, J=8 Hz, 1H); 7.24 (d, J=4 Hz, 1H); 7.49 (dd, J=2.5 Hz, 8 Hz, 1H); 7.56 (d, J=5 Hz, 1H); 7.62 (d, J=2.5).

A suspension of sodium hydride (50% dispersion 0.8 mmol, 38 mg) in DMF (2 ml) (sieve dried) was cooled to −5° C. and treated with methyl 2-(ethylamino)pyridine-5-carboxylate (0.145 g, 0.8 mmol). The reaction was stirred at −5° C. for 30 minutes and then treated with 5-bromo-2-(2-thienylmethoxy)benzyl bromide (0.29 g, 0.8 mmol) in DMF (0.5 ml). The reaction was allowed to warm to ambient temperature and stirred for 18 hours. The reaction was poured into saturated aqueous ammonium chloride. The combined organic extracts were washed once with brine, dried (MgSO$_4$) and evaporated. The residue was purified by chromatography (eluant: diethyl ether/hexane) to give methyl 2-[N-(2-(2-thienylmethoxy)-5-bromobenzyl)N-ethylamino]pyridine-5-carboxylate as a colourless oil (0.03 g, 8%).

MS (FAB+): (M+H)+461

$^1$H-NMR (200 MHz, DMSO-d$_6$) δ: 1.1 (t, J=7 Hz, 3H); 3.59 (q, J=7 Hz, 2H) 3.78 (s, 3H); 4.7 (s, 2H); 5.37 (s, 2H); 6.62 (d, J=10 Hz, 1H); 7.04 (m, 2H); 7.19 (m, 2H); 7.4 (dd, J=2.9 Hz, 1H); 7.55 (dd, J=1.7, 5 Hz, 1H); 7.9 (dd, J=2 Hz, 9 Hz, 1H); 8.61 (d, J=2 Hz, 1H).

EXAMPLE 32

4—Chloromethyl-2-methylthiazole (0.102 g, 0.69 mmol) was treated with a solution of methyl 2-[N-(5-bromo-2-hydroxybenzyl)-N-ethylamino)pyridine-5-carboxylate (0.2 g, 0.55-mmol) in DMF (4 ml). The resultant solution was treated with potassium carbonate (0.23 g, 1.7 mmol). The reaction was stirred at ambient temperature for 24 hours.

The DMF was evaporated. The residue was diluted with water and extracted with ethyl acetate (3×3 ml). The organic layers were combined and evaporated. The residue was dissolved in methanol (3 ml) and THF (2 ml) and treated with aqueous sodium hydroxide solution (1N, 2.5 ml). The reaction was warmed to 40° C. and stirred for 18 hours. The organic solvents were evaporated and the remaining aqueous solution was acidified with acetic acid (1N, 2.6 ml). The precipitate was stirred for 1 hour and then collected by filtration and washed with water (3 ml). The solid was dried under vacuum over P$_2$O$_5$, to give 2-[N-(5-bromo-2-(2-methylthiazol-4-ylmethoxy)benzyl-N-ethylamino]pyridine-5-carboxylic acid.

The starting material was prepared as follows:

6—Chloronicotinic acid (100 g, 0.63 mol) was treated with ethylamine (70% in water, 500 ml). The reaction was sealed in an autoclave and heated to 170° C. for 6 hours. The reaction mixture was evaporated, partially neutralised with concentrated HCl and the pH adjusted to pH5 with galcial acetic acid. The solid product was filtered off and dried in vacuo for 18 hours to give 6-(ethylamino)nicotinic acid (87.8 g, 84%).

MS (CI$^+$)=167 (M+H)$^+$

NMR (250 MHz, DMSO-d$_6$) δ: 1.15 (t, J=7 Hz, 3H); 3.3 (q, J=7 Hz, 2H); 6.45 (d, J=9 Hz, 1H); 7.25 (brt, 1H); 7.78 (dd, J=2, 9 Hz, 1H); 8.54 (d, J=2 Hz, 1H); 11.6 (brs, 1H).

A suspension of 6-(ethylamino)nicotinic acid (50 g, 0.3 mol) in methanol (500 ml) was treated with concentrated H$_2$SO$_4$ (30 ml). The reaction was heated at reflux for 18 hours. The reaction mixture was then evaporated, poured into ice water (1 L) and adjusted to pH8 with solid sodium hydrogen carbonate (foaming). The aqueous mixture was extracted with ethyl acetate (3×300 ml) and the organic layers combined, dried (MgSO$_4$) and evaporated to give methyl 6-(ethylamino)nicotinoate as an off-white solid (45.5 g, 84%).

MS (CI+): 181 (M+H)$^+$

NMR (200 MHz, DMSO-d$_6$) δ: 1.14 (t, J=7 Hz, 3H); 3.3 (q, J=7 Hz, 2H); 3.76 (s, 3H); 6.46 (d, J=9 Hz, 1H); 7.39 (brt, 1H); 7.80 (dd, J=3, 9 Hz, 1H); 8.56 (d, J=3 Hz, 1H).

A solution of 5-bromosalicyladehyde (12.0 g, 59.7 mmol) in DMF (50 ml) was treated with K$_2$CO$_3$ (16.5 g, 120 mmol) and benzyl bromide (11.2 g, 65.6 mmol). The reaction was stirred at ambient temperature for 18 hours, diluted with ethyl acetate and filtered. The filtrate was washed with HCl (0.05M), saturated aqueous sodium hydrogen carbonate and brine. The organic phase was dried (Na$_2$SO$_4$) and evaporated and the residue triturated with hexane/ethyl ether. The product was filtered off to give 2-benzyloxy-5-bromobenzaldehyde as a white solid (15.8 g, 90%) m.p. 70°–72° C.

MS (Cl+): 291 (M+H)$^+$

NMR (200 MHz, DMSO-d$_6$) δ: 5.38 (s, 2H); 7.5 (m, 6H); 7.9 (m, 2H); 10.41 (s, 1H).

A suspension of 2-benzyloxy-5-bromobenzaldehyde (14.5 g, 50.2 mmol) in absolute ethanol (250 ml) was treated with sodium borohydride (2.6 g, 68.8 mmol). The reaction was stirred and the temperature slowly rose to 33° C. After 1 hour the reaction mixture was evaporated and the residue dissolved in ethyl acetate and poured into a mixture of ice water (200 ml) and 1N HCl (25 ml). The organic layer was separated, washed with aqueous sodium hydrogen carbonate, brine, dried (Na$_2$SO$_4$) and evaporated to give 2-benzyloxy-5-bromobenzylalcohol as a pale yellow oil (14.85 g, quantitative).

MS (CI+) 292 (M+).

NMR (200 MHz, DMSO-d$_6$) δ: 4.52 (d, J=5 Hz, 2H); 5.12 (s, 2H); 5.17 (t, J=5 Hz, 1H); 6.98 (d, J=9 Hz, 1H); 7.4 (m, 6H); 7.5 (d, 2H, 1H).

A solution of 2-benzyloxy-5-bromobenzyl alcohol (14.75 g, 50.2 mmol) in anhydrous ethyl ether (150 ml) was cooled to 4° C. A solution of PBr3 (13.68 g, 50 mmol) in anhydrous ether (40 ml) was added dropwise keeping the temperature below 10° C. The reaction was allowed to warm to ambient temperature and stirred for 1 hour. The reaction was filtered through silica gel (200 g). The silica gel was washed with ethyl ether to remove all the product. The filtrate was washed with water (1×150 ml), aqueous saturated sodium hydrogen carbonate (1×150 ml) and brine (1×150 ml). The organic layer was dried (Na$_2$SO$_4$) and evaporated to give 2-benzyloxy-5-bromobenzylbromide as a pale yellow oil (15.2 g, 85%) which crystallised on standing.

MS (EI+): 354 (M+)

NMR (200 MHz, DMSO-d6): δ8:4.65 (s, 2H); 5.2 (s, 2H); 7.05 (d, J=9 Hz, 1H), 7.4 (m, 6H); 7.66 (d, J=3 Hz, 1H).

A solution of methyl 6-ethylaminonitcotinoate (15.2 g, 84.4 mmol) in DMF (50 ml) was cooled to 0° C. and treated with sodium hydride (60%, 75 mmol). The reaction was stirred for 1 hour and a solution of 2-benzyloxy-5-bromobenzylbromide (25 g, 70.2 mmol) in DMF (50 ml) added. The reaction was allowed to warm to ambient temperature and stirred for 18 hours. The reaction was quenched with water and extracted with ethyl acetate (three times). The organic layers were combined, washed with water and brine twice, dried (MgSO$_4$) and evaporated to give a white solid. Recrystallisation from ethyl/acetate/hexane gave methyl 2-[N-(2-benzyloxy-5-bromobenzyl)-N-ethylamino]pyridine-5-carboxylate (22.7 g, 71%).

MS (CI+): 455/457 (M+H)$^+$

NMR (200 MHz, DMSO-d$_6$): δ: 1.1 (t, J=7 Hz, 3H); 3.5 (q, J=7 Hz, 2H); 3.78 (s, 3H); 4.77 (s, 2H); 5.18 (s, 2H); 6.65 (d, J=9 Hz, 1H); 7.08 (m, 2H); 7.4 (m, 6H); 7.9 (dd, J=2, 9 Hz, 1H); 8.62 (d, 1H).

A solution of methyl 2-(N-(2-benzyloxy-5-bromobenzyl)-N-ethylamino]-5-pyridylcarboxylate (10.0 g, 22 mM) in dichloromethane (150 ml) was treated with boron trichloride dimethyl sulfide complex (40 ml, 2M, 80 mM). The reaction was stirred at ambient temperature for 48 hours. Saturated sodium bicarbonate solution was added and the layers were separated. The aqueous layer was washed with dichloromethane. The organic layers were combined, dried (MgSO$_4$) and evaporated to give an off-white solid. The off-white solid was subjected to chromatography (diluted with ethyl acetate/hexane) to give the title product methyl 2-[N-(5-bromo-2-hydroxybenzyl)-N-ethylamino]-pyridine-5-carboxylate (6.02 g, 75%).

MS (CI+) 365 (M+H)+

NMR (250 MHz, DMSO-d$_6$): δ1.14 (t, J=7 Hz, 3H); 3.61 (q, J=7 Hz, 2H); 3.78 (s, 3H); 4.66 (s, 2H); 6.65 (d, J=9 Hz, 1H); 6.8 (d, J=9 Hz, 1H); 7.02 (d, J=2 Hz, 1H); 7.2 (dd, J=2, 9 Hz, 1H); 7.93 (dd, J=2, 9 Hz, 1H); 8.64 (d, J=2 Hz, 1H); 10.13 (s, 1H).

EXAMPLE 33

A solution of methyl 2-[N-(5-bromo-2-(3-methyl fur-2-ylmethoxy)benzyl)-N-ethylamino]pyridine-5-carboxylate (0.24 g, 0.52 mmol) in THF (3 ml) and methanol (3 ml) was treated with aqueous sodium hydroxide solution (1N, 2.6 ml). The reaction was heated to 40° C. for 7 hours. The reaction was partially evaporated, the residue was diluted with water and acidified with acetic acid. 2-[N-(5-Bromo-2-(3-methylfur-2-ylmethoxy)benzyl-N-ethylamino]pyridine-5-carboxylate was collected by filtration as a white solid (0.186 g, 80%), mpt 198.7°–202.0° C.

$^1$H-NMR: (200 MHz, DMSO-d$_6$) δ: 1.1 (t, J=7 Hz, 3H); 2.3 (s, 3H); 3.58 (q, J=7 Hz, 2H); 4.69 (s, 2H); 4.98 (s, 2H); 6.50 (d, J=2 Hz, 1H); 6.59 (d, J=9 Hz, 1H); 7.04 (d, J=2.7 Hz, 1H); 7.12 (d, J=9 Hz, 1H); 7.41 (dd, J=2.7, 9 Hz, 1H); 7.5 (d, J=2 Hz, 1H); 7.89 (dd, J=2.7, 9 Hz, 1H); 8.59 (d, J=2.7 Hz, 1H); 12.36 (bs, 1H).

The starting material was prepared as follows:

To a cooled (0° C.) suspension of LiAlH$_4$ (0.45 g, 12.4 mmol) in THF (15 ml), was added dropwise, methyl 2-methylfuran-3-carboxylate (1.395 g, 9.96 mmol). The reaction was allowed to warm to ambient temperature and stirred for 24 hours. Water was added to quench the reaction. Ethyl acetate was then added and the mixture was filtered through Celite. The layers were separated and the aqueous phase was extracted with (2×). The organic phases were combined, dried (MgSO$_4$) and evaporated to give 2-methyl-3-hydroxymethylfuran was as a colourless oil (0.95 g, 85%) which was used without purification.

MS (EI+): (M+) 112

$^1$H-NMR (250 MHz, DMSO-d$_6$) δ: 2.22 (s, 3H); 4.26 (s, 2H); 4.7 (bs, 1H); 6.34 (d, J=2 Hz, 1H); 7.39 (d, J=2 Hz, 1H).

A solution of methyl 2-[N-(5-bromo-2-hydroxybenzyl)-N-ethylamino]pyridine-5-carboxylate (0.44 g, 1.21 mmol) in THF (15 ml) was treated with triphenylphosphine (0.35 g, 1.34 mmol) and diethylazodicarboxylate (0.42 g, 2.4 mmol). A solution of 2-methyl-3-hydroxymethylfuran (0.202 g, 1.8 mmol) in THF (12 ml) was added. The reaction was stirred at ambient temperature for 72 hours. The reaction was evaporated and partitioned between ethyl acetate and water. The aqueous phase was extracted with ethyl acetate (2x) and the organic phases were combined, dried (MgSO4) and evaporated. The residue was purified by chromatography (eluant: ethyl acetate/hexane) to give 2-[N-(5-bromo-2-(3-methylfur-2-ylmethoxy)benzyl)-N-ethylamino]pyridine-5-carboxylate as an off-white solid (0.24 g, 29%).

$^1$H-NMR (200 MHz, DMSO-d$_6$) δ: 1.1 (t, J=7 Hz, 3H); 2.29 (s, 3H); 3.48 (q, J=7 Hz, 2H); 3.79 (s, 3H); 4.68 (s, 2H); 4.96 (s, 2H); 6.47 (d, J=2 Hz, 1H); 6.6 (d, J=9 Hz, 1H); 7.03 (d, J=2.6 Hz, 1H); 7.12 (d, J=8 Hz, 1H); 7.4 (dd, J=2.6, 9 Hz, 1H); 7.48 (d, J=2 Hz, 1H); 7.89 (dd, J=2.6, 9 Hz, 1H); 8.60 (d, J=2.6 Hz, 1H).

EXAMPLE 34

A solution of methyl 2-[N-(bromo-2-(4-pyridylmethoxy)benzyl)-N-ethylamino]pyridine-5-carboxylate (0.138 g, 0.3 mmol) in THF (10 ml) and methanol (5 ml) was treated with an aqueous solution of sodium hydroxide (1.5 ml, 1N). The reaction was stirred at ambient temperature for 18 hours. A further portion of sodium hydroxide solution (1.5 ml, 1N) was added and the reaction stirred for a further 24 hours. Solvents were removed under reduced pressure and the residue dissolved in water and acidified with acetic acid. 2-[N-(5-Bromo-2-(4-pyridylmethoxy)benzyl)-N-ethylamino]pyridine-5-carboxylic acid was filtered off as a white solid.

$^1$H-NMR (200 MHz, DMSO-d$_6$) δ: 1.13 (t, J=7 Hz, 3H); 3.62 (q, J=7 Hz, 2H); 4.84 (s, 2H); 5.25 (s, 2H); 6.64 (d, J=9 Hz, 1H); 7.04 (m, 2H); 7.42 (m, 3H); 7.91 (dd, J=2.4 Hz, 9 Hz, 1H); 8.60 (m, 3H).

MS (FAB+): 442 (M+H)

The starting material was prepared as follows:

A solution of 4-chloromethylpyridine hydrochloride (0.12 g, 0.73 mmol) in DMF (3 ml) was treated with potassium carbonate (0.29 g, 2.10 mmol). A solution of methyl 2-[N-(5-bromo-2-hydroxybenzyl)-N-ethylamino]pyridine-5-carboxylate (0.26 g, 0.71 mmol) in DMF (4 ml) was added. The reaction was stirred for 24 hours and then the reaction was diluted with water and extracted with ethyl acetate (×3). The organic phases were combined and washed with water and brine once, dried (MgSO$_4$) and evaporated. Chromatography eluant: ethyl acetate/hexane gave methyl 2-[N-(5-bromo-2-(4-pyridylmethoxy)benzyl)-N-ethylamino]pyridine-5-carboxylate as a white solid (0.209 g, 65%).

$^1$H-NMR (200 MHz, DMSO-d$_6$) δ: 1.11 (t, J=7 Hz, 3H); 3.61 (q, J=7 Hz, 2H); 3.77 (s, 3H); 4.84 (s, 2H); 5.24 (s, 2H); 6.8 (d, J=9 Hz, 1H); 7.04 (m, 2H); 7.43 (m, 3H); 7.92 (dd, J=2, 9 Hz, 1H); 8.6 (m, 3H).

REFERENCE EXAMPLE 1

A mixture of 2-benzyloxybenzaldehyde (50 g) and methyl-4-aminobenzoate (35.6 g) was heated on a steam bath for 3 hours. The cooled reaction mixture was dissolved in a mixture of tetrahydrofuran (300 mL) and ethanol (100 mL) and sodium borohydride (8.51 g) was added in portions. The mixture was stirred at ambient temperature for 14 hours then cooled to 0° C. in an ice bath. Acetic acid was added dropwise until effervescence ceased and the mixture was poured into water (1000 mL). The aqueous portion was extracted four times with ethyl ether (200 mL each time). The combined ether extracts were washed with saturated aqueous sodium bicarbonate solution (200 mL) and dried over anhydrous magnesium sulphate. The residue obtained on removal of the solvent was dissolved in methanol (200 mL) and methyl-[N-(2-benzyloxybenzylamino]benzoate crystallized from the solution, yield 42.66 g, mp 95° C.

Analysis: C$_{22}$H$_{21}$NO$_3$ Theory, C: 76.1; H: 6.1; N: 4.0; Found: C: 76.0; H: 6.0; N: 4.1.

$^1$H NMR (DMSO-d$_6$): δ3.73 (s, 3H), 4.36 (s, 2H), 5.19 (s, 2H), 6.56–7.70 (m, 13H).

REFERENCE EXAMPLE 2

The compounds listed in appended Tables 6 to 6f were prepared from the appropriate starting materials using a similar. method to that of reference example 1.

REFERENCE EXAMPLE 3

A suspension of 2-benzyloxy-5-methanesulphonylbenzaldehyde (10 g) and methyl 4-aminobenzoate (5.2 g) in toluene (100 mL) was heated on a steam bath for 18 hours and evaporated to dryness. The residue was dissolved in a mixture of methanol (100 mL) and tetrahydrofuran (100 mL) and the first portion of sodium borohydride (1.3 g) was added. The mixture was stirred for 1 hour and the second portion of sodium borohydride (1.3 g) was added. The mixture was stirred for 30 minutes and evaporated to dryness. The residue was dissolved in dichloromethane (250 mL) and was washed with water and dried (MgSO$_4$). The solvent was evaporated and the residue subjected to chromatography on silica eluting initially with dichloromethane and then with a mixture of ethyl acetate and dichloromethane (3/7 v/v) to give methyl 4-[N-(2-benzyloxy-5-methanesulphonylbenzyl)amino]benzoate, yield 10.2 g, mp 124° C.

$^1$H-NMR (DMSO-d$_6$): δ3.06 (s, 3H), 3.75 (s, 3H), 4.41 (s, 2H), 5.33 (s, 2H), 6.61 (d, 2H, J=8.5 Hz), 7.3–7.55 (m, 6H), 7.68 (d, 2H, J=8.5 Hz), 7.76 (d, 1H, J=2.5 Hz), 7.81 (dd, 1H, J=8.5 Hz, J=2.5 Hz).

Using this method with the appropriate starting materials the following were prepared:

methyl 4-[N-(2-benzyloxy-5-cyanobenzyl)amino]benzoate mp 118° C.

ethyl 2-[N-(2-benzyloxy-5-bromobenzyl)amino]-1-methylimidazole-5-carboxylate mp 68° C. methyl 2-[N-(2-benzyloxy-1-naphthylmethyl)amino]pyridine-5-carboxylate mp 129° C.

REFERENCE EXAMPLE 4

The compounds listed in the appended Tables 7 to 7c were prepared from the appropriate starting materials using a similar method to reference example 3.

REFERENCE EXAMPLE 5

Sodium hydride (5.9 g of a 60% dispersion in mineral oil) was suspended in N,N-dimethylformamide (200 mL) and the mixture was cooled to 0° C. (ice bath). Methyl-[N-(2-benzyloxybenzyl)amino]benzoate (42.6 g) was added as a solid over 30 minutes and the mixture was stirred at 0° C. for 1 hour. Ethyl iodide was added dropwise and the mixture was stirred at ambient temperature for 15 hours then poured into water (700 mL). The aqueous mixture was extracted three times with ethyl acetate (150 mL each time), the combined extracts were washed three times with water (200 mL each time) and dried over the anhydrous magnesium sulphate. On evaporation of the solvent the residue was triturated with hexane to give methyl-[N-(2-benzyloxybenzyl)-N-ethyl-amino]benzoate, yield 44 g, mp $^1$H NMR (DMSO-d$_6$): δ1.14 (t, 3H J=6.9 Hz), 3.51 (q, 2H J=6.9 Hz), 3.73 (s, 3H), 4.58 (s, 2H), 5.19 (s, 2H), 6.60–7.72 (m, 13H).

Occasionally, during the procedure described above there was adventitious hydrolysis of the ester product to give the carboxylic acid. The following acids were obtained thus, 4-[N-(2-benzyloxy-5-bromobenzyl)-N-(3-pyridylmethyl) amino]benzoic acid mp 215° C.

4-[N-(2-benzyloxy-5-bromobenzyl)-N-ethylamino]-3-ethoxybenzoic acid mp 155° C.

REFERENCE EXAMPLE 6

The compounds listed in appended Tables 8 to 8d were prepared from the appropriate ester and halide using a similar method to that of reference example 5.

REFERENCE EXAMPLE 7

Ethyl 4-(N-ethylamino)benzoate (1.85 g) was added to a suspension of sodium hydride (0.46 g of a 60% dispersion in mineral oil) in N,N-dimethylformamide (25 mL) at 0° C. and the mixture was stirred at this temperature for 1 hour. Solid 2-benzyloxy-5-chlorobenzyl bromide was added and the mixture was stirred at ambient temperature for 18 hours. The solvent was evaporated under reduced pressure and the residue dissolved in ethyl acetate (30 mL) and washed once with water and dried (MgSO$_4$). The residue obtained on removal of the solvent was subjected to chromatography on silica eluting with dichloromethane. Evaporation of the appropriate fraction gave ethyl 4-[N-(2-benzyloxy-s-chlorobenzyl)-N-ethylamino]-benzoate as a gum, yield 1.6 g.

$^1$H NMR (DMSO-d6): δ1.13 (t, 3H J=6.3 Hz), 1.25 (t, 3H J=6.3 Hz), 3.52 (q, 2H=6.3 Hz), 4.21 (q, 2H J=6.3 Hz), 4.21 (q, 2H J=6.3 Hz), 4.57 (s, 2H), 5.21 (s, 2H), 6.62–7.74 (m, 12H).

Following the procedure outlined above and using the appropriate starting materials there was prepared:

ethyl 4-[N-(2-benzyloxy-5-bromobenzyl)amino]-3-nitrobenzoate mp 101° C.; [ethyl 4-amino-3-nitrobenzoate (CA 98 143133e) can be prepared from 4-amino-3-nitrobenzoic acid and ethanol in the presence of $H_2SO_4$ (Ind. J. Chem. Sect. B 27B, 1106, 1988)].

ethyl 4-[N-(2-benzyloxy-5-nitrobenzyl)amino]benzoate; methyl 5-[N-(2-benzyloxybenzyl)amino]-2-pyridinecarboxylate.

REFERENCE EXAMPLE 8

Methyl iodide (2.7 g) was added to a stirred suspension of ethyl 4-[N-(2-benzyloxy-5-bromobenzyl)amino]-3-hydroxybenzoate (6 g) and potassium carbonate (2.6 g) in N,N-dimethylformamide (50 mL) and stirring was continued for 3 hours. The reaction mixture was poured into water (200 mL) and this was extracted three times with diethyl ether (50 mL each time). The combined diethyl ether extracts were washed three times with water (50 mL each time) and dried ($MgSO_4$). The residue obtained on evaporation of the solvent was triturated with petroleum-ether (bp 60–80° C.) to give ethyl 4-[N-(2-benzyloxy-5-bromobenzyl) amino]-3-methoxybenzoate, yield 5.3 g, mp 78° C.

$^1$H NMR (DMSO-d6): δ1.27 (t, 3H J=7 Hz), 3.87 (s, 3H), 4.22 (q, 2H J=7 Hz), 4.39 (s, 2H), 6.33 (bs, 1H), 6.39 (d, 1H), 7.07–7.51 (m, 10H).

Using the same method with the appropriate starting material there was prepared ethyl 4-[N-(2-benzyloxy-5-bromobenzyl)amino]-3- ethoxybenzoate, mp 96° C.

REFERENCE EXAMPLE 9

Ethyl 4-[N-(2-benzyloxy-5-bromobenzyl)amino]3-nitrobenzoate (10 g) was dissolved in acetic acid (50 mL) (warming was required) and iron dust (6.92 g) was added followed by the addition of water (20 mL). There was an exothermic reaction (to 70° C.). The reaction mixture was stirred at ambient temperature for 16 hours, water (300 mL) was added and the mixture was extracted three times with ethyl acetate (100 mL each time). The combined extracts were washed consecutively with water (3×100 mL) and saturated aqueous sodium bicarbonate (2×100 mL) and dried ($MgSO_4$). The residue obtained on removal of the solvent was filtered through silica, eluting initially with a mixture of dichloromethane and hexane (1/1 v/v) and then with dichloromethane, to give ethyl 4-[N-(2-benzyloxy-5-bromobenzyl)amino]-3-aminobenzoate, yield 8.78 g, mp 135° C.

Using a similar procedure to that outlined above methyl 4-[N-(2-benzyloxy-5-aminobenzyl)]-N-ethylamino] benzoate was prepared from the corresponding nitro compound.

REFERENCE EXAMPLE 10

Borane-tetrahydrofuran complex (2.7 mL of a 1.0M solution in THF) was added over 5 minutes to a solution of ethyl 4-[N-(3-benzyloxy-2-thienoyl)-N-(ethyl)amino]benzoate (1.0 g) in THF (10 mL). The reaction mixture was stirred at ambient temperature for 15 minutes and then heated under reflux for 1 hour. An excess of aqueous 2N HCl was added to the cooled reaction mixture which was evaporated to dryness. The residue was made basic by the addition of aqueous potassium carbonate solution and this was extracted with diethyl ether (50 mL). The ether extract was washed with brine and dried over $MgSO_4$. The oil obtained on removal of the solvent was subjected to chromatography on silica eluting with dichloromethane to give ethyl 4-[N-(3-benzyloxy-2-thienylmethyl)-N-(ethyl)amino]benzoate as an oil in 32% yield.

$^1$H NMR (CDCl$_3$) δ1.18 (t, 3H), 1.35 (t, 3H), 3.46 (q, 2H), 4.30 (q, 2H), 4.56 (s, 2H), 5.09 (s, 2H), 6.69 (d, 2H), 6.83 (d, 1H), 7.03 (d, 1H), 7.36–7.39 (m, 5H), 7.84 (d, 2H).

REFERENCE EXAMPLE 11

A mixture of methyl-4-[N-(2-benzoyloxy-4-bromobenzyl)-N-ethylamino]benzoate (5.64 g) and cuprous cyanide (1.28 g) in N,N-dimethylformamide (100 ml) was stirred and heated at 140° C. for 10 hours in an oil bath. The mixture was allowed to cool and was poured into a solution of ethylenediamine (10 ml) in water (240 ml). The resulting mixture was stirred for 30 minutes and then extracted three times with EtoAc (50 ml each time). The oil obtained on removal of the solvent was subjected to chromatography on silica eluting with dichloromethane to give methyl-4-[N-(2-benzyloxy-4-cyanobenzyl)-N-ethylamino]benzoate, yield 3.9 g.

REFERENCE EXAMPLE 12

Benzyl bromide (1.35 ml) was added to a mixture of 4-bromo-2-hydroxybenzaldehyde (2.07 g) and potassium carbonate (1.38 g) in DMF (20 ml) and the mixture was stirred at ambient temperature for 10 hours. The reaction mixture was poured into water (50 ml) to give 2-benzyloxy-4-bromobenzaldehyde as a solid which was filtered and dried, yield 2.88 g. The material was used in subsequent reactions without purification.

Using a similar method to that outlined above there was prepared:

2-benzyloxy-6-bromobenzaldehyde 2-benzyloxy-4-methoxybenzaldehyde 2-benzyloxy-5-bromobenzaldehyde-[1H-NMR (DMSO-d$_6$): δ5.29 (s, 2H), 7.3–7.5 (m, 6H), 7.80 (m, 2H), 10.33 (s, 1H).

methyl 3-benzyloxy-2-thienylcarboxylate 2-benzyloxy-5-chlorobenzaldehyde 2-benzyloxy-5-methylbenzaldehyde 2-benzyloxy-5-methoxybenzaldehyde 2-benzyloxy-5-trifluoromethylbenzaldehyde 2-benzyloxy-5-iodobenzaldehyde

REFERENCE EXAMPLE 13

Toluene (70 ml) was added to a stirred solution of magnesium methoxide in methanol (224 ml, 10.3 wt % solution), 3-bromophenol (30 ml) was added to this mixture over 15 minutes. The mixture was heated under reflux for 1 hour and then toluene (110 ml) was added. Solvent was distilled off until the reaction mixture temperature reached 87°–94° C. (vapour temperature 64° C.). Paraformaldehyde (24 g) in toluene (160 ml) was added in portions over 1 hour and the mixture was heated under reflux for a further 3 hours, then allowed to cool. Toluene was added and the mixture was washed three times with aqueous 2N sulphuric acid then once with water. The organic layer was dried ($MgSO_4$) and concentrated to give an oil. This oil was subjected to chromatography on silica, eluting with diethylether:hexane (5:95). Three fractions were isolated (listed in the order in which they eluted from the column), 6-bromo-2-hydroxybenzaldehyde; 4-bromo-2-hydroxybenzaldehyde and finally, recovered 3-bromophenol.

REFERENCE EXAMPLE 14

Oxalyl chloride (3.6 ml) was added to a solution of 2-benzyloxy-4-methylbenzoic acid (9.02 g) in dichloromethane (20 ml), one drop of DMF was added and the mixture was stirred for 2 hours then evaporated to dryness. The residue was dissolved in diglyme (70 ml) and cooled to −78° C. under argon. Lithium-tri-t-butoxyaluminohydride (78 ml of 0.5M solution in diglyme) was added at such a rate that the temperature did not exceed −60° C. The mixture was stirred below this temperature for 2 hours and was then poured carefully onto ice and acidified with concentrated HCl. The mixture was extracted with diethylether (3×150 ml) and the gum obtained on work up was subjected to chromatography on silica eluted with dichloromethane to give 2-benzyloxy-4-methylbenzaldehyde (3.73 g).

REFERENCE EXAMPLE 15

A solution of benzyl 2-benzyloxy-4-methylbenzoate acid (25 g) in a mixture of THF and methanol was treated with aqueous 2N NaOH (188 ml) and heated under reflux for 12 hours. The reaction mixture was concentrated to half its volume and was diluted with water, extracted once with EtOAc and the aqueous layer was acidified with HCl to pH4. The solid which precipitated was filtered and dried to give 2-benzyloxy-4-methylbenzoic acid (yield 9.73 g).

REFERENCE EXAMPLE 16

A mixture of 4-methylsalicyclic acid (20 g), benzylbromide (33 ml) and potassium carbonate (36.3 g) in DMF (100 ml) was stirred for 12 hours. The mixture was poured into water (300 ml) and extracted three times with diethylether (100 ml each time). The combined organic extracts were washed with water and dried. Removal of the solvent gave benzyl 2-benzyloxy-4-methylbenzoate acid as a yellow liquid, yield 45 g.

REFERENCE EXAMPLE 17

A mixture of 2-benzyloxy-5-bromobenzaldehyde (102 g) ethanediol (21 g) and p-toluenesulphonic acid (1 g) in toluene (250 ml) was heated under reflux for 4 hours then evaporated to dryness. The residue was dissolved in dichloromethane (500 ml) and washed three times with saturated aqueous sodium bicarbonate solution, dried and evaporated to dryness to give 2-benzyloyl-5-bromobenzaldehyde ethylene acetal 126 g m.p. 85° C.

The acetal described above (50 g) was dissolved in THF (550 ml) and the solution was cooled to −78° C. and n-BuLi (93.6 ml of 1.6M in hexane) was added over 30 minutes. The reaction mixture was stirred at this temperature for 30 minutes and a solution of dimethylsulphide (10 g) in THF (50 ml) was added. The reaction mixture was allowed to warm to ambient temperature and diethylether (1 L) was added. The mixture was washed with brine (2×200 ml) dried and evaporated to give 2-benzyloxy-5-methylthiobenzaldehyde ethylene acetal (36 g) m.p. 46° C.

The acetal was converted to the 2-benzyloxy-5-methylthiobenzaldehyde using a similar method to that of Reference Example 19.

REFERENCE EXAMPLE 18

Commercial m-chloroperbenzoic acid (20.6 g) was dissolved in dichloromethane, dried with $MgSO_4$ and filtered. The solution was added dropwise to a solution of 2-benzyloxy-5-methylthiobenzaldehyde ethylene acetal (18 g) in dichloromethane (100 ml) at 0° C. until all the starting material had been consumed (monitored by TLC). The reaction mixture was washed with 10% aqueous sodium thiosulphate (2×20 ml), saturated sodium bicarbonate (5×100 ml) and dried. The residue obtained on work up was subjected to chromatography on silica, eluting with EtOAc: dichloromethane (10:90) to give 2-benzyloxy-5-methylsulphonylbenzaldehyde ethylene acetal 6.4 g. Further elution of the column with EtOAc: dichloromethane (40:60) gave 2-benzyloxy-5-methylsulphinylbenzaldehyde ethylene acetal (yield 5.3 g).

REFERENCE EXAMPLE 19

A solution of 2-benzyloxy-5-methylsulphonylbenzaldehyde ethylene acetal (28.6 g) in THF (100 ml) and MeOH (100 ml) containing 2N HCl (50 ml) was stirred for 4 hours. The reaction mixture was concentrated to half its volume and water (100 ml) was added. The solid product was filtered and dried to give 2-benzyloxy-5-methylsulphonylbenzaldehyde yield 24 g m.p. 129° C.

$^1$H-NMR (DMSO-$d_6$): δ3.21 (s, 3H), 5.41 (s, 2H), 7.3–7.6 (m, 6H), 8.1–8.2 (m, 2H), 10.41 (s, 1H). Using this same method with the appropriate starting material there was obtained 2-benzyloxy-5-methylsulphinylbenzaldehyde m.p. 103°–104° C.

REFERENCE EXAMPLE 20

A mixture of methyl-2-[N-(2-benzyloxy-5-nitrobenzyl)-N-t-butoxycarbonylamino]pyridine-5-carboxylate (5.2 g) and formic acid (20 ml) was heated on a steam bath to give a clear solution. The mixture was evaporated to dryness and the residue obtained was dissolved in diethylether (100 ml) and washed with saturated sodium bicarbonate. The organic layer was dried and evaporated to give methyl-2-[N-(2-benzyloxy-5-nitrobenzyl)-amino]pyridine-5-carboxylate, yield 3.3 g. This same procedure was used to prepare ethyl-2-[N-(2-benzyloxy-5-bromobenzyl)-amino]thiophene-5-carboxylate.

The methyl-2-[N-(2-benzyloxy-5-nitrobenzyl)-N-butoxycarbonylamino]pyridine-5-carboxylate used as starting material was prepared as follows:

A slurry of methyl 2-t-butoxycarbonylpyridine-5-carboxylate (3.2 g) in THF (25 ml) was added all at once to a suspension of sodium hydride (0.61 g of a 60% dispersion in oil) in DMF (25 ml) at 0° C. The mixture was stirred at this temperature for 30 minutes and a solution of 2-benzyloxy-5-nitrobenzylbromide (4.1 g) in THF (20 ml) was added over 10 minutes. The mixture was stirred at ambient temperature for 12 hours and poured onto ice (200 g), and the solid was filtered and dried. The solid was dissolved in dichloromethane and filtered through silica eluting with dichloromethane to give methyl-2-[N-(2-benzyloxy-5-nitrobenzyl)-N-t-butoxycarbonylamino] pyridine-5-carboxylate yield 5.2 g. This same procedure was used to prepare ethyl-2-[N-(2-benzyloxy-5-bromobenzyl)-N-t-butoxycarbonylamino]thiophene-5-carboxylate.

REFERENCE EXAMPLE 21

5-Bromo-2-benzyloxybenzaldehyde (7.2 g) and ethyl 2-[4-aminophenyl]acetate (4.45 g) were heated on a steam bath for 2 hours. The mixture was cooled and dissolved in ethanol (100 ml) and $NaBH_4$ (0.94 g) was added. The mixture was stirred at ambient temperature for 30 minutes, $NaBH_4$ (0.5 g) added and stirred at ambient temperature for 2 hours. Acetic acid (2 ml) was added dropwise and the solvent evaporated to half volume. The mixture was partitioned between water (100 ml) and diethyl ether (3×75 ml) and the combined organic extracts washed with $NaHCO_3$ (2×50 ml), dried ($MgSO_4$) and evaporated. The residue was subjected to chromatography eluting with $CH_2Cl_2$ to give ethyl 2-[4-(2-benzyloxy-5-bromobenzylamino)phenyl]acetate: (yield 6.4 g, m.p. 73° C.).

REFERENCE EXAMPLE 22

Sodium hydride (422 mg) was suspended in DMF (25 ml) and cooled to 0° C. ethyl 2-[4-(2-benzyloxy-5- bromobenzylamino)phenyl]acetate (4 g) in DMF (25 ml) was added dropwise and the reaction mixture stirred at 0° C. for 30 minutes. Ethyl iodide (1.37 g) was added and the mixture stirred overnight at ambient temperature. The solvent was evaporated to dryness and the residue dissolved in ethyl acetate (50 ml), washed with brine, dried (MgSO$_4$) and evaporated. The residue was subjected to chromatography eluting with methylene chloride, to give ethyl 2-[4-(2-benzyloxy-5-bromobenzylamino)phenyl]-2-butanoate: (yield 4.2 g, gum).

REFERENCE EXAMPLE 23

A mixture of ethyl 6-chloro-3-pyridazine carboxylate (6.5 g) [British patent number 856, 409], potassium isocyanate (3.5 g), tert-butanol (6.0 ml), tetrakis(triphenylphosphine) palladium (400 mg) and diglyme (6 ml) in DMF (50 ml) was heated at reflux for 2 hours, cooled and partitioned between diethyl ether and water. The organic layer was dried (MgSO$_4$), filtered through silica gel and evaporated. The resulting solid was purified by crystallisation from isohexane to give ethyl 6-(tert-butoxycarbonylamino)-3-pyridazine carboxylate (2.4 g), mp 87°–88° C.

$^1$H-NMR (CDCl$_3$): δ1.46 (t, 3H, J=6.7 Hz), 1.55 (s, 9H), 4.52 (q, 2H, J=6.7 Hz), 8.15 (d, 1H, J=9.0 Hz), 8.30 (broad, 1H), 8.35 (d, 1H, J=9.0 Hz).

A mixture of ethyl 6-(tert-butoxycarbonylamino)-3-pyridazine carboxylate (2.4 g), 1-(benzyloxy)-2-bromomethyl-4-bromobenzene (3.2 g) and sodium hydride (0.5 g of a 50% W/W dispersion in oil) in DMF was stirred for 2 hours. The mixture was diluted with diethyl ether and washed with water. The organic solution was dried (MgSO$_4$), filtered and evaporated. Ethyl 6-[N-(2-benzyloxy-5-bromobenzyl)-N-(tert-butoxycarbonyl)amino]-3-pyridazinecarboxylate was isolated by flash chromatography, eluting with 2% ethyl acetate in CH$_2$Cl$_2$. Yield: 1.7 g.

$^1$H-NMR (CDCl$_3$): δ1.45 (9H, s), 1.47 (3H, t, 3=6.7 Hz), 4.50 (2H, q, J=6.7 Hz), 4.98 (2H, s), 5.45 (2H, s), 6.77 (1H, d, J=8.4 Hz) 7.20–7.40 (7H, m), 7.96 (1H, d, J=9.0 Hz), 8.19 (1H, d, J=9.0Hz).

A mixture of ethyl 6-[N-(2-benzyloxy-5-bromobenzyl)-N-(tert-butoxycarbonyl)amino]-3-pyridazinecarboxylate (2.0 g) and trifluoroacetic acid (25 ml) in CH$_2$Cl$_2$ (25 ml) was allowed to stand for 18 hours. The solvents were evaporated, the residue dissolved in CH$_2$Cl$_2$ and washed with dilute aqueous Na$_2$CO$_3$ solution, dried (MgSO$_4$) and evaporated to give ethyl 6-[2-benzyloxy-5-bromobenzylamino]-3-pyridazinecarboxylate as a solid (1.5 g).

$^1$H-NMR (CDCl$_3$): δ1.44 (3H, t, J=6.7 Hz), 4.46 (2H, q, J=6.7 Hz), 4.70 (2H, J=6.0, Hz), 5.08 (2H, s), 5.78 (1H, t broad), 6.58 (1H, d, J=9.0 Hz), 6.83 (1H, d, J=8.4 Hz), 7.3–7.5 (7H, m), 7.79 (1H, d, J=9.0 Hz).

To a mixture of ethyl 6-[2-benzyloxy-5-bromobenzylamino]-3-pyridazinecarboxylate (1.2 g) and iodoethane (0.25 ml) in DMF (10 ml) was added NaH (0.15 g of a 50% w/w dispersion in oil). The reaction was stirred for 18 hours and poured into a mixture of dilute aqueous HCl and ethyl acetate. The organic solution was washed with water, dried (MgSO$_4$), filtered and evaporated. The residue was purified by chromatography on silica gel, eluting with 5% ethyl acetate in CH$_2$Cl$_2$ to give ethyl 6-[N-2-benzyloxy-5-bromobenzyl)-N-ethylamino]-3-pyridazinecarboxylate (0.6 g).

$^1$H-NMR (CDCl$_3$): δ1.24 (3H, t, J=6.7 Hz), 1.44 (3H, t, J=6.7 Hz), 3.75 (2H, q, J=6.7 Hz), 4.46 (2H, q, J=6.7 Hz), 4.81 (2H, s), 5.07 (2H, s), 6.62 (1H, d, J=9.0 Hz), 6.85 (1H, d, J=8.4 Hz), 7.20–7.40 (7H, m), 7.76 (1H, d, J=9.0 Hz).

REFERENCE EXAMPLE 24

To a stirred solution of ethyl, 5-(N-(2-benzyloxy-5-bromobenzyl)amino)pyrazine-2-carboxylate (7.0 g, 15.8 mM) in DMF (100 ml) at 20° C., under argon atmosphere, was added sodium hydride dispersion (50% in oil, 0.8 g, 16 mM). When effervescence ceased, after 1 hour, iodoethane (1.3 ml, 16 mM) was added and stirring continued, under argon, for 1 hour. The solvent was evaporated at reduced pressure and the residue partitioned between ethyl acetate (250 ml) and water (100 ml), the organic layer was dried (MgSO$_4$) and evaporated at reduced pressure. The residue was purified by chromatography on silica eluting with 5% ethyl acetate in dichloromethane to give ethyl 5-(N-2 (benzyloxy-5-bromobenzyl)-N-(ethyl)amino)pyrazine-2-carboxylate: as a yellow gum, 48 g.

$^1$H-NMR (CDCl$_3$): δ1.20 (t, 3H, J=7 Hz), 1.41 (t, 3H, J=7 Hz), 3.65 (q, 2H, J=Hz), 4.42 (q, 2H, J=7H), 4.80 (s, 2H), 5.07 (s, 2H), 6.84 (d, 1H, J=9 Hz), 7.17 (d, 1H, J=2.5 Hz), 7.3–7.4 (m, 6H), 7.97 (d, 1H, J=1.25 Hz), 8.79 (d, 1H, J=1.5 Hz). The starting material was prepared as follows:

To a solution of diethyl 2,5-pyrazinedicarboxylate (J. Med Chem 28, 1232) (50.0 g, 0.223 mol) in ethanol (1l) at 20° C. was added dropwise, during 4 hours, a solution of hydrazine monohydrate (9.5 ml, 0.196 mole) in ethanol (100 ml). The mixture was stirred for 12 hours at 20° C., then the crystalline product filtered off and washed successively with ethanol and diethyl ether, yielding ethyl 2,5-pyrazinedicarboxylate monohydrazide (34.0 g, mp 142°–143° C.).

To a suspension of ethyl 2,5-pyrazinedicarboxylate monohydrazide (34.0 g, 0.162 mol) in water (600 ml) containing sodium nitrite (60.0 g, 0.87 mol) was added dichloromethane (600 ml) and cooled to 0°–5° C. The mixture was stirred vigorously while adding dropwise, during 30 minutes, 6N HCl (250 ml, 1.5 mol) so that the temperature did not exceed 10° C. The organic layer was separated, dried over magnesium sulphate and evaporated at reduced pressure, at ambient temperature, to give the crude acid azide (35 g) which was suspended in toluene (500 ml) containing tert-butanol (50 ml). The mixture was cautiously heated to reflux while stirring for 1 hour (nitrogen evolved). On cooling crystals of ethyl 5-(tert-butoxycarbonylamino) pyrazine-2-carboxylate were deposited. (25.0 g, mp 162°–163° C.).

To a solution of ethyl 5-(tert-butoxycarbonylamino) pyrazine-2-carboxylate (10.7 g 0.04 mol) in DMF (160 ml) at 20° C., under argon atmosphere, was added sodium hydride dispersion (50% in oil, 1.85 g, 0.04 mol) and stirred for 1 hour until effervescence ceased. Next was added 2-benzyloxy-5-bromobenzylbromide (14.3 g, 0.04 mol) and stirring continued at 20° C. under argon for 2 hours. The solvent was evaporated at reduced pressure and the residue partitioned between dichloromethane (500 ml) and water (250 ml), the organic layer was dried over magnesium sulphate and evaporated at reduced pressure to give a crude solid (21 g). Purification was by chromatography on silica, eluting with 5% ethyl acetate in dichloromethane to give ethyl 5-(N-(2-benzyloxy-5-bromobenzyl)-N-tert-butoxycarbonylamino)pyrazine-2-carboxylate as a white solid (16 g, mp 116°–7° C.).

To a solution of ethyl N-(2-benzyloxy-5-bromobenzyl)-5-(tert-butoxycarbonylamino)pyrazine-2-carboxylate (10.0 g) in dichloromethane (50 ml) at 20° C. was added trifluroracetic acid (50 ml). The solution was stirred for 2 hours until gas evolution ceased, then the solvents were evaporated at reduced pressure. The residue was dissolved in ethyl acetate (200 ml) and washed with dilute sodium carbonate solution, then dried over magnesium sulphate and evaporated at reduced pressure. The residue was crystallised from hexane/dichloromethane (9:1) yielding ethyl 5-(N-(2-benzyloxy-5-bromobenzyl)amino)pyrazine-2-carboxylate as white needles (7.5 g, 123°–3° C.).

REFERENCE EXAMPLE 25

Ethyl/methyl 2-[N-(2-benzyloxybenzyl)amino]pyridine-5-carboxylate was prepared from 2-benzyloxybenzaldehyde and methyl 2-amino-5-pyridylcarboxylate using a similar method to that of Example 13, except the ester and aldehyde were heated together in toluene in a Dean-Stark apparatus with separation of water.

$^1$H-NMR (DMSO-d$_6$): δ1.29 (t,2H, 6.5 Hz), 3.76 (s, 1H), 4.22 (q, 4/3H, 6.5 Hz), 4.57 (d, 2H, J=6 Hz), 5.18 (s, 3H), 6.56 (d, 1H, J=8.5 Hz), 6.88–7.5 (m, 9H), 7.70 (brt, 1H), 7.81 (dd, 1H, J=8.5 Hz, J=2.5 Hz), 8.54 (d, 1H, J=2.5 Hz).

REFERENCE EXAMPLE 26

Methyl 3-benzyloxy-2-thienylcarboxylate was converted to 3-benzyloxy-2-thienyl carboxylic acid using a similar method to that of Example 1.

3-Benzyloxy-2-thienylcarboxylic acid was converted to the corresponding acid chloride which was reacted with ethyl 4-ethylaminobenzoate using a similar method to that of Example 4 to give ethyl 4-[N-(3-benzyloxy-2-thienoyl)-N-ethylamino]benzoate.

REFERENCE EXAMPLE 27

A mixture of 2-[N-(5-bromo-2-benzyloxybenzyl)-N-ethylamino]pyridine-5-carboxylic acid (1.4 g) [table 1a, compound 2] and 1,1-carbonyldiimidazole (0.62 g) were heated in DMF at 55° C. for 3 hours. The mixture was cooled to ambient temperature, aqueous ammonia (20 ml) was added and the mixture was stirred for 18 hours. The solvent was evaporated and the residue purified by MPLC eluting with methanol: dichloromethane (5:95) to give 2-[N-(5-bromo-2-benzyloxybenzyl)-N-ethylamino]pyridine-5-carboxamide (671 mg).

$^1$H-NMR of amide (DMSO-d$_6$): δ1.10 (t, 3H, J=6.7 Hz), 3.59 (q, 2H, J=6.7 Hz), 4.74 (s, 2H), 5.18 (s, 2H), 6.58 (d, 1H, J=9.7 Hz), 7.02 (d, 1H, J-2.7 Hz), 7.09 (d, 1H, J=9.7 Hz), 7.10–7.50 (m, 6H), 7.69 (bs, 1H), 7.91 (dd, J=9.7, 1.7 Hz), 8.57 (d, J=1.7 Hz).

MS (CI$^+$): 440 [M+H]$^+$.

m.p. (°C.): 169.5–170.0.

Trifluoroacetic anhydride (0.51 ml) was added dropwise to a mixture of 2-[N-(5-bromo-2-benzyloxybenzyl)-N-ethylamino]pyridine-5-carboxamide (1.05 g) in pyridine (0.58 ml) and THF (20 ml) at 20° C. The mixture was stirred at ambient temperature for 18 hours, diluted with ethyl acetate, washed with water, saturated aqueous NaHCO$_3$ and brine, and dried (MgSO$_4$). The solvent was evaporated and the residue purified by MPLC, eluting with dichloromethane/methanol mixtures (100:0 to 95:5) to give 2-[N-(5-bromo-2-benzyloxybenzyl)-N-ethylamino]-5-cyanopyridine (0.81 g) as a gum.

REFERENCE EXAMPLE 28

Butyl 6-[N-(2-benzyloxy-5-bromobenzyl)-N-(prop-2-yn-1-yl)amino]pyridazine-3-carboxylate was prepared from butyl 6-[N-(2-benzyloxy-5-bromobenzyl)amino]pyridazine-3-carboxylate (trifluoroacetic acid salt) by a similar method to that described in Reference example 5 except using an extra equivalent of sodium hydride to neutralize the salt.

REFERENCE EXAMPLE 29

To a solution of 1,1-thiocarbonyldiimidazole (2.5 g) in dichloromethane (20 ml) was added a mixture of N-ethyl-N-(2-benzyloxy-5-bromobenzyl)amine hydrobromide (5.0 g) and triethylamine (1.8 ml) in dichloromethane (50 ml) at 4° C. The mixture was stirred at ambient temperature for 18 hours, washed with brine, dried (Na$_2$SO$_4$), filtered and evaporated. The resulting residue was purified by trituration with a diethyl ether/ethanol mixture to give an orange solid (5.02 g). A mixture of the solid (2.5 g), and hydrazine hydrate (0.31 ml) in ethanol (25 ml) was heated at reflux for 2 hours. Hydrazine hydrate (0.31 ml) was added and the mixture heated at reflux for a further 4 hours. The solvent was evaporated, the residue dissolved in dichloromethane, washed with brine, dried (Na$_2$SO$_4$), filtered and evaporated. The residue was purified by chromatography eluting with ethyl acetate/CH$_2$Cl$_2$ mixtures (0:100, 2.5:97.5, 5:95) to give 4-[2-benzyloxy-4-bromobenzyl]-4-ethylthiosemicarbazide (0.69 g). To a mixture of 4-[2-benzyloxy-5-bromobenzyl]-4-ethylthiosemicarbazide (0.67 g), pyridine (0.15 ml) and dichloromethane (10 ml) was added ethyloxalyl chloride (0.21 ml) at 0° C. The mixture was stirred at ambient temperature for 10 minutes, and subjected to chromatography, eluting with 2.5% methanol/dichloromethane, to give a brown foam (0.82 g). To a mixture of the foam (0.79 g) in toluene (16 ml) heated at reflux, was added a mixture of methanesulphonic acid (0.15 ml) in toluene (2 ml) dropwise. The mixture was heated at reflux for 30 minutes, cooled, diluted with ethyl acetate and washed with sodium hydrogen carbonate. The organic solution was dried (Na$_2$SO$_4$), filtered and evaporated. The residue was purified by chromatography, eluting with mixtures of dichloromethane and ethyl acetate (100:0, 97.5: 2.5, 95:5), to give ethyl 5-[N-(2-benzyloxy-s-bromobenzyl)-N-ethylamine]-1,3,4-thiadiazole-2-carboxylate (0.61 g).

REFERENCE EXAMPLE 30

A solution of methyl 2-[N-(2-hydroxy-5-bromobenzyloxy)-N-ethylamino]pyridine-5-carboxylate in DMF (4 mL) was treated with 4-methoxybenzyl chloride (0.086 g, 0.55 mmol) and potassium carbonate (0.23 g, 1.65 mmol). The reaction was stirred at ambient temperature for 18 hours, diluted with water (4 mL) and extracted with ethyl acetate (3×3 mL). The organic layers were combined, washed with water (2×4 mL) and brine (1×4 mL) and evaporated to give methyl 2-[N-(2-(4-methoxybenzyloxy)-5-bromobenzyl)-N-ethylamino]pyridine-5-carboxylate as a white solid.

MS (FAB$^+$): 485 (M+H)$^+$ $^1$H NMR (250 MHz, DMSO-d$_6$): δ1.1 (t, J=7 Hz, 3H); 3.58 (q, J=7 Hz, 2H); 3.76 (s, 3H); 3.78 (s, 3H), 4.72 (s, 2H); 5.1 (s, 2H); 6.61 (d, J=9 Hz, 1H); 6.93 (d, J=9 Hz, 2H); 7.06 (d, J=2 Hz, 1H); 7.10 (d, J=9 Hz, 1H); 7.40 (m, 3H); 7.88 (dd, J=2.9 Hz, 1H); 8.62 (d, J=2 Hz, 1H).

REFERENCE EXAMPLE 31

The compounds listed in Table 9 were prepared using a similar method to that described in Reference example 30 using the appropriate alkylating agent. X in Table 9 indicates whether the alkylating agent used was the chloride or the bromide.

For starting material see Reference example 32.

REFERENCE EXAMPLE 32

A solution of methyl 2-[N-(2-benzyloxy-5-bromobenzyl)-N-ethylamino]pyridine-5-carboxylate (10.0 g, 22 mmol) in dichloromethane (150 mL) was treated with trichloride dimethyl sulphide complex (40 ml, 2M, 80 mmol). The reaction was stirred at ambient temperature for 28 hours. Saturated aqueous sodium hydrogen carbonate solution was added and the layers separated. The aqueous layer was washed with dichloromethane, the organic layers combined, dried (MgSO$_4$) and evaporated to give an off-white solid. This was subjected to chromatography to give methyl 2-[N-(2-hydroxy-5-bromobenzyl)-N-ethylamino]pyridine-5-carboxylate (6.0 g, 75%).

MS (CI+): 365 (M+H)$^+$ $^1$H-NMR (250 MHz, DMSO-d$_6$) 1.14 (t, J=7 Hz, 3H); 3.61 (q, J=7 Hz, 2H); 3.78 (s, 3H); 4.66 (s, 2H); 6.65 (d, J=9 Hz, 1H); 6.80 (d, J=9 Hz, 1H); 7.02 (d, J=2 Hz, 1H); 7.20 (dd, J=2,9 Hz, 1H); 7.93 (dd, J=2,9 Hz, 1H); 8.64 (d, J=2 Hz, 1H); 10.13 (s, 1H).

In the following tables when a structure is given in a table for 'Het' or 'Ar' the right hand bond is linked to the nitrogen and the left hand bond to the tetrazole, carboxy, ester, cyano, amide, carboxyalkyl or acylsulphonamide group.

TABLE 1

| Compound No. | R | R$^1$ | mp °C. | Footnote |
|---|---|---|---|---|
| 1 | 5-Br | Me | 248 | |
| 2 | 5-Br | Et | 225 | |
| 4 | 5-MeS | Et | 177 | |
| 5 | H | Et | 165 | |
| 6 | 5-MeSO | H | 177 | |
| 7 | 5-NO$_2$ | H | 177–80 | |
| 8 | 5-MeSO | Et | 208 | |
| 9 | 5-MeSO$_2$ | H | 205 | a |
| 10 | 5-CN | H | 42–4 | |
| 11 | 5-MeSO$_2$ | Et | 154 | |

TABLE 1-continued

| Compound No. | R | R$^1$ | mp °C. | Footnote |
|---|---|---|---|---|
| 12 | 5-NO$_2$ | Et | 254–8 | |
| 13 | 5-NH$_2$ | Et | 148–51 | |
| 14 | 5PhSO$_2$NH— | Et | 68–70 | |
| 15 | 5-Br | Pr$^n$ | 252 | |
| 16 | 5-Cl | Et | 218 | |
| 17 | 5-Me | H | 166–7 | |
| 18 | 5-Me | Et | 174–6 | |
| 19 | 5-Br | CH$_3$CO— | 182 | |
| 20 | 5-PhSO$_2$CH$_2$— | H | 130–42 | |
| 21 | 5-MeO | H | 173–4 | |
| 22 | 5-MeO | Et | 209–11 | |
| 23 | 5-Br | H | 155 | |
| 24 | 4-Br | Et | 183–5 | |
| 25 | 4-Br | H | 184–6 | |
| 26 | 6-Br | Et | 197–9 | |
| 27 | 5-CF$_3$ | H | 190–1 | |
| 28 | 5-CF$_3$ | Et | 194–5 | |
| 29 | 4-MeO | Et | 167–9 | |
| 30 | 4-Me | Et | 161–4 | |
| 31 | 4-CN | Et | 204–8 | |
| 32 | 5-Br | —CH$_2$C≡CH | 195 | |

Footnote
a) $^1$H-NMR (DMSO-d$_6$): δ1.18(t, 3H, J=6.5Hz), 3.03(s, 3H), 3.56(q, 2H, J=6.5Hz), 4.61(s, 2H), 5.33(s, 2H), 6.65(d, 2H, J=9Hz), 7.3–7.56(m, 7H), 7.7(d, 2H, J=9Hz), 7.61(dd, 1H, J=8.5Hz, J=2.5Hz).
See Table 8, compound 12.

TABLE 1a

| Compound No. | R | R$^1$ | Het | mp (°C.) | Footnote |
|---|---|---|---|---|---|
| 1 | 5-Br | Et | pyridine | 108–10 | |
| 2 | 5-Br | Et | pyridine | 220–3 | a |
| 3 | H | Et | " | 106–10 | |
| 4 | 5-Br | H | thiazole | 182 | |

TABLE 1a-continued

[Structure: benzene ring with substituents - position 6: CH₂N(R¹)-Het-COOH; position 2: OCH₂Ph; position 3/4: R]

| Compound No. | R | R¹ | Het | mp (°C.) | Footnote |
|---|---|---|---|---|---|
| 5 | 5-Br | Et | [thiophene-2,5-diyl] | 150 | |
| 6 | 5-Br | Et | [thiazole-2,4-diyl] | 163 | |
| 7 | 5-Br | Me | [pyridine-2,6-diyl] | 248–50 | b |
| 8 | H | Et | " | 139–40 | c |
| 9 | 5-Br | —CH₂C≡CH | " | 148–50 | |
| 10 | 5-Br | H | " | 162–5 | |
| 11 | 5-NO₂ | Et | " | 206–10 | |
| 12 | 5-I | Et | [pyridine-2,6-diyl] | 208–10 | |
| 13 | 5-Br | Et | [methylthiazole] | 93 | |
| 14 | 5-Cl | Et | [pyridine-2,6-diyl] | 204–6 | |
| 15 | 5-MeS | Et | " | 143–6 | |
| 16 | 5-MeSO₂ | Et | " | 164–5 | |
| 17 | 5-Br | H | [methylthiazole] | 127 | |
| 18 | 5-Br | Et | [pyridazine-3,6-diyl] | 145–146 | d |
| 19 | 5-Br | Et | [methyloxazole] | 164.5–165.5 | e |
| 20 | 5-Br | Et | [pyrazine-2,5-diyl] | — | f |

TABLE 1a-continued

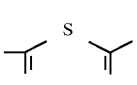

| Compound No. | R | R¹ | Het | mp (°C.) | Footnote |
|---|---|---|---|---|---|
| 21 | 5-Br | Me | N—N (pyridazine) | | g |
| 22 | 5-Br | $CH_2C\equiv CH$ | " | | h |
| 23 | 5-Br | $CH_2CF_3$ | " | | i |
| 24 | 5-Br | Et | S, N—N (thiadiazole) | 76–78 | j |

Footnote
a) 1H-NMR (DMSO-$d_6$) δ: 1.10(m, 3H), 3.57(q, 2H, J=5.5Hz), 4.75(s, 2H), 5.17(s, 2H), 6.61(d, 1H, J=8Hz), 7.05–7.11(m, 2H), 7.3–7.51(m, 6H), 7.89(dd, 1H, J=8Hz J=3Hz), 8.58(d, 1H, J=3Hz).
See Table 8c, compound 1.
b) Final acid: $^1$H-NMR (DMSO-$d_6$): δ3.11(s, 3H), 4.83(s, 2H), 5.17(s, 2H), 6.67(d, 1H, J=8.5Hz), 7.04(d, 1H, J=2Hz), 7.09(d, 1H, J=7Hz), 7.3–7.5(m, 6H), 7.90(dd, 1H, J=9Hz, J=2.5Hz), 8.61(d, 1H, J=2.5Hz).
See Table 8c, compound 2.
c) Final acid: $^1$H-NMR (DMSO-$d_6$): δ1.11(t, 3H, 6.5Hz), 3.63(q, 2H, J=6.5Hz), 4.77(s, 2H), 5.19(s, 2H), 6.58(d, 1H, J=8.5Hz), 6.83–7.00(m, 2H), 7.1–7.5(m, 6H), 7.85(dd, 1H, J=8.5Hz, J=2.5Hz), 8.59(d, 1H, 2 5Hz), 12 38(brs, 1H).
See Table 8c, compund 3.
d) ethanol was used as the solvent in the hydrolysis and the product was crystallised from $CH_2Cl_2$/diethyl ether/hexane (1:1:1).
MS: 442/444 $[M+H]^+$ (bromine pattern microanalysis:
calc: C: 57.0%; H: 4.6%; N: 9.5%
found: C: 57.0%; H: 4.6%; N: 9.4%.

Compound 18
$^1$H-NMR (DMSO-$d_6$): δ1.12 (t, 3H, J=6.7 Hz), 3.67 (q, 2H, J=6.7 Hz), 4.85 (s, 2H), 5.12 (s, 2H), 7.05–7.18 (m, 3H), 7.3–7.5 (6H, m), 7.76 (d, 1H, J=9.0 Hz).
See reference example 23.

e) $^1$H-NMR (DMSO-$d_6$): δ1.06 (t, 3H, J=6.5 Hz), 3.39 (q, 2H, J=6.5 Hz), 4.57 (s, 2H), 5.13 (s, 2H), 7.08 (d, 1H, J=8.5 Hz), 7.26–7–46 (m, 7H), 8.07 (s, 1H).

f) $^1$H-NMR (DMSO-$d_6$): δ1.12 (t, 3H, J=7 Hz), 3.65 (q, 2H, J=7 Hz), 4.82 (s, 2H, 5 17 (s, 2H), 7.10 (d, 1H, J=9 Hz), 7.18 (d, 1H, J=2.5 Hz), 7.3–7.45 (m, 6H), 8.18 (d, 1H, J=1.25 Hz), 8.62 (d, 1H, J=1.5 Hz), 12.78 (brs, 1H).

g) 1H-NMR ($CDCl_3$) δ: 3.25 (s, 3H), 4.87 (s, 2H), 5.04 (s, 2H), 6.82 (d, 1H, J=9 Hz), 6.88 (d, 1H, J=8 Hz), 7.2–7.4 (m, 7H), 7.80 (d, 1H, J=9 Hz).

The final product was purified by crystallisation from $CH_2Cl_2$/hexane. The starting ester was prepared using a similar method to that of Reference Example 23 except iodomethane was used in place of iodoethane in the alkylation step.

h) The product was extracted with dichloromethane and purified by crystallising from dichloromethane/hexane followed by flash chromatography eluting with 10% methanol in dichloromethane.

i) Ethanol was used as the solvent in the hydrolysis and the product was purified by flash chromatography eluting with methanol:dichloromethane mixtures (0:100, 1:99, 5:95, 10:90).

$^1$H NMR (DMSO-$d_6$+AcOH-$d_4$ heated to 323K): δ4.61 (q, 2H, J=8.2 Hz), 4.93 (s, 2H), 5.15 (s, 2H), 7.08 (d, 1H, J=8.5 Hz), 7.15–7.23 (m, 3H), 7.32–7.48 (m, 6H), 7.89 (d, 1H, J=8.5 Hz).

The starting material was prepared as follows:

A mixture of 2,2,2-trifluoroethylamine hydrochloride (68 g), diethyl ether (500 ml) and 40% aqueous sodium hydroxide solution (55 ml) was shaken together. The organic layer was dried ($MgSO_4$), added to 2-benzyloxy-5-bromobenzylbromide (17.0 g) in dichloromethane (100 ml) and left to stand in a closed flask for 72 hours. The solvent was evaporated, the residue partitioned between diethyl ether and 2N aqueous sodium hydroxide. The organic layer was removed, dried ($MgSO_4$) and evaporated to give N-(2, 2,2-trifluoroethyl)-2-benzyloxy-5-bromobenzylamine (17.5 g) as a yellow oil.

N-(2,2,2-Trifluroethyl) 2-benzyloxy-5-bromobenzylamine (9.2 g), butyl 6-chloropyridazine-3-carboxylate (5.4 g) and tosic acid (100 mg) were heated together at 120° C. for 18 hours. The resulting residue was purified by chromatography, eluting with dichloromethane, then 10% diethyl ether/dichloromethane, to give four products. The third product was further purified by re-chromatography, eluting with 5% diethyl ether/dichloromethane to give butyl 6-[N-(2-benzyloxy-5-bromobenzyl)-N-(2,2,2-trifluoroethyl)amine]pyridazine-3-carboxylate.

j) See reference example 29 for starting material.

TABLE 1b

| Compound No | R | Ar | mp °C. |
|---|---|---|---|
| 1 | H | (phenyl) | 214 |
| 2 | Et | " | 252 |
| 3 | H | (pyridyl) | 210 |
| 4 | Et | " | 225 |

TABLE 1c

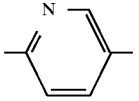

| Compound No. | R | X | $R_1$ | mp (°C.) | Footnote |
|---|---|---|---|---|---|
| 1 | 5-MeSO$_2$ | —N(Et)— | CO$_2$H | 192 | a |
| 2 | 5-Br | —NH— | CH$_2$CO$_2$H | 114 | |
| 3 | 5-Br | —NH— | CH(Et)CO$_2$H | gum | |

Footnote
a) ethyl 4-(N-(2-benzyloxy-5-methanesulphonylbenzyl)-N-ethyl-N-oxide amino)benzoate was a side product isolated in the oxidation of ethyl 4-(N-(benzyloxy-5-methanethiobenzyl)-N-ethylamino)benzoate to the corresponding methanesulphonyl substituted compound.

TABLE 1d

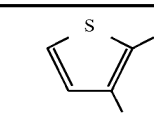

| Compound No. | R | $R^1$ | $R^2$ | mp (°C.) |
|---|---|---|---|---|
| 1 | H | H | CO$_2$H | 125 |
| 2 | H | Et | CO$_2$H | 125 |
| 3 | 5-Br | H | CO$_2$H | 160 |
| 4 | 5-Br | Et | CO$_2$H | 148 |
| 5 | 5-Br | H | CO$_2$H | 160 |

TABLE 1e

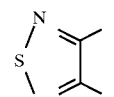

| Compound No. | R | $R^1$ | $R^2$ | mp (°C.) |
|---|---|---|---|---|
| 1 | H | H | 2-MeO | 108 |
| 2 | H | Et | 2-MeO | 118 |
| 3 | 5-Br | H | 3-OH | 188 |
| 4 | 5-Br | H | 3-MeO | 178 |
| 5 | 5-Br | H | 3-EtO | 195 |
| 6 | 5-Br | H | 3-NO$_2$ | 223 |
| 7 | 5-Br | Et | 3-MeO | 148 |
| 8 | 5-Br | Et | 3-NO$_2$ | 178 |
| 9 | 5-Br | H | 3-NH$_2$ | 95 |

TABLE 1f

| Compound No | Het | mp °C. | Footnote |
|---|---|---|---|
| 1 | (thiophene) | 165–168 | a |
| 2 | (thiadiazole) | 198–199 | b |

Footnote
a) Compound No. 1 $^1$H-NMR (DMSO-d$_6$): δ1.09(t, 3H, J=7Hz), 3.45(q, 2H, J=7Hz), 4.56(s, 2H), 5.16(s, 2H), 6.72(d, 2H, J=9Hz), 7.06(d, 1H, J=6Hz), 7.29(d, 1H, J=6Hz), 7.33–7.51(m, 5H), 7.67(d, 2H, J=9Hz).
For preparation of starting material see Reference example 26.
b) Preparation of starting material:
4-Cyano-3-hydroxy-1,2,5-thiadiazole [CA 111 134167, East German Patent No. DD 263,767] was converted to 4-benzyloxy-1,2,5-thiadiazole-3-nitrile using a similar method to that of Reference example 12. The nitrile was converted to 4-benzyloxy-1,2,5-thiadiazole-3-carboxylic acid using a similar method to that of example 1, except it was heated for 24 hours and the product was isolated by extraction with ethyl acetate.

The carboxylic acid was converted to the corresponding acid chloride and reacted with methyl 4-aminobenzoate using a similar method to that described in example 4 to give methyl 4-[4-benzyloxy-1,2,5-thiadiazol-3-ylcarbamoyl]benzoate.

The above methyl ester was reduced to give methyl 4-[4-benzyloxy-1,2,5-thiadiazol-3-ylmethylamino]benzoate using a similar process to that of reference example 10. This methyl ester was alkylated using a similar method to that of reference example 5 to give methyl 4-[N-(4-benzyloxy-1,2,5-thiadiazol-3-ylmethyl)-N-ethylamino]benzoate.

TABLE 1g

[Structure: Br-substituted phenyl-OCH2-phenyl(R) with CH2N(Et) linked to pyridine-CO2H]

| Compound No. | R | mp (°C.) | Footnote |
|---|---|---|---|
| 1 | 4-OCH3 | 150–158 | a |
| 2 | 4-Cl | 238–242 | b |
| 3 | 3-CN | 180–185 | c |
| 4 | 4-F | 238–239 | d |
| 5 | 4-tbutyl | 172–173 | e |
| 6 | 4-OCF3 | 182–184 | f |
| 7 | 4-CF3 | 160–162 | g |

TABLE 1g-continued

Footnotes
a) MS(FAB+): 471/473 (M+H)+. See Reference example 31 for starting material.
b) $^1$H NMR (200 MHz, DMSO-$d_6$): δ1.1(t, J=7Hz, 3H); 3.6(q, J=7Hz, 2H); 4.78(s, 2H); 5.18(s, 2H); 6.6(d, J=9Hz, 1H); 7.07(m, 2H); 7.45(m, 5H); 7.9(dd, J=3.9Hz, 1H); 8.6(d, J=3Hz, 1H).
See Table 9, compound 1 for starting material.
c) See Table 9, compound 3 for starting material.
d) MS(CI+): 459/461 (M+H)+. See Table 9, Compound 4 for starting material.
e) MS(CI+): 497/499 (M+H)+. See Table 9, Compound 5 for starting material.
f) MS(FAB+): 525/527 (M+H)+. See Table 9, Compound 6 for starting material.
g) See Table 9, Compound 2 for starting material.

TABLE 2

[Structure: R-substituted phenyl with OCH2Ph, CH2N(R1) linked to phenyl-CONHR2]

| Compound No. | R | R1 | R2 | mp (°C.) | Footnote |
|---|---|---|---|---|---|
| 1 | H | Et | Pr$^n$ | 106–8 | |
| 2 | H | Et | —CH2-(3-pyridyl) | 83 | |
| 3 | H | Et | —CH2-(3-pyridyl) | 89–91 | |
| 4 | 5-Br | Me | —CH2-(3-pyridyl) | 136 | |
| 5 | 5-Br | Me | —CH2-(3-pyridyl) | 136 | |
| 6 | 5-Br | Me | —CH2CH2OH | 131 | |
| 7 | 5-Br | Me | Pr$^n$ | 152 | |
| 8 | 5-Br | Et | —CH2-(2-pyridyl) | gum | |

TABLE 2-continued

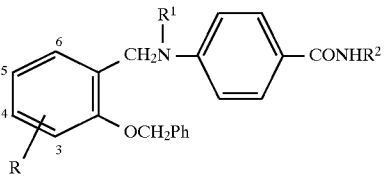

| Compound No. | R | R¹ | R² | mp (°C.) | Footnote |
|---|---|---|---|---|---|
| 9 | 5-Br | Et | —CH$_2$CH$_2$OH | gum | |
| 10 | 5-Br | Et | Pr$^n$ | 158–9 | |
| 11 | 5-Br | —CH$_2$-(3-pyridyl) | —CH$_2$-(3-pyridyl) | 164 | |
| 12 | 5-Br | —CH$_2$-(3-pyridyl) | —CH$_2$CH$_2$CH$_3$ | 154 | |
| 13 | 5-MeS | Et | Pr$^n$ | 122 | |
| 14 | 5-MeS | Et | —CH$_2$-(2-pyridyl) | gum | |
| 15 | 5-MeS | Et | —CH$_2$-(3-pyridyl) | 108 | |
| 16 | 5-MeSO$_2$ | Et | —CH$_2$-(3-pyridyl) | 96–100 | |
| 17 | 5-MeSO$_2$ | Et | —CH$_2$-(3-pyridyl) | 96–100 | |
| 18 | 5-MeSO$_2$ | Et | Pr$^n$ | 70–90 | |
| 19 | 5-MeSO$_2$ | Et | —CH$_2$CH$_2$OH | 90 | |
| 20 | 4-Br | Et | Pr$^n$ | gum | |
| 21 | 4-Br | Et | —CH$_2$-(3-pyridyl) | gum | |
| 22 | 4-Br | Et | —CH$_2$-(3-pyridyl) | gum | |
| 23 | 6-Br | Et | Pr$^n$ | 125–7 | |
| 24 | 6-Br | Et | —CH$_2$CH$_2$OH | 175–7 | |
| 25 | 4-Br | Et | —CH$_2$CH$_2$OH | 120–2 | |
| 26 | 4-Br | Et | —CH$_2$—CH(Me)OH (S) | gum | |
| 27 | 4-Br | Et | —CH$_2$—CH(Me)OH (R) | gum | |

TABLE 2-continued
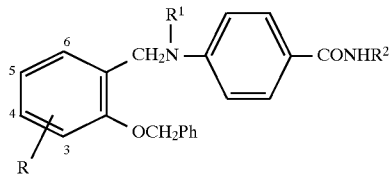
| Compound No. | R | R¹ | R² | mp (°C.) | Footnote |
|---|---|---|---|---|---|
| 28 | 4-Me | Et | 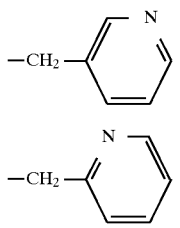 | gum | |
| 29 | 4-Me | Et | 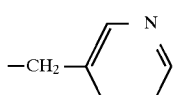 | gum | |
| 30 | 4-Me | Et | Pr$^n$ | gum | |
| 31 | 4-Me | Et | —CH$_2$CH$_2$OH | gum | |
| 32 | 4-MeO | Et | 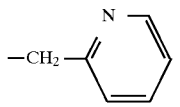 | gum | |
| 33 | 4-MeO | Et | 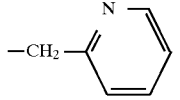 | gum | |
| 34 | 5-Cl | Et | 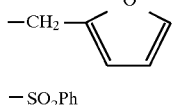 | 98 | |
| 35 | 5-Cl | Et | 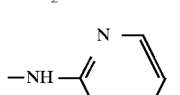 | 112 | |
| 36 | 5-Br | PhCH$_2$— | —SO$_2$Ph | 92 | |
| 37 | 5-MeSO$_2$— | Et | —SO$_2$Ph | >260 | a |
| 38 | 5-MeSO$_2$— | Et | 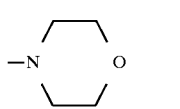 | | |
| 39 | H | Et |  | | |
| 40 | H | Et | —N⟨piperidine⟩ | | |
| 41 | H | Et |  | | |
Footnote
a) Compound 37: $^1$H-NMR (DMSO-d$_6$): δ1.14(t, 3H, J=6.5Hz), 3.04(s, 3H), 3.56(q, 3H, J=6.5Hz), 4.61(s, 2H), 5.32(s, 2H), 6.65(d, 2H), J=9Hz), 7.1–7.74(m, 12H), 7.63(dd, 1H, J=8.5Hz, J=2.5Hz), 7.97(dd, 2H, J=7.5, J=1.5Hz).
See Table 1, compound 9.

TABLE 2a

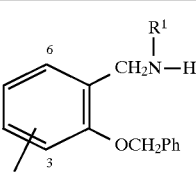

| Compound No. | R | R¹ | R² | mp (°C.) | Footnote |
|---|---|---|---|---|---|
| 1 | 5-Br | Et | 3-pyridylmethyl | 138–40 | a |
| 2 | 5-Br | Et | Pr$^n$ | 151–4 | |
| 3 | 5-Br | Et | 2-pyridylmethyl | 49–50 | |
| 4 | 5-Br | Me | Pr$^n$ | 137–9 | |
| 5 | 5-Br | Me | 2-pyridylmethyl | 60 | |
| 6 | 5-Br | Me | 3-pyridylmethyl | 106–8 | |
| 7 | 5-Br | H | Pr$^n$ | 171–3 | |
| 8 | 5-Br | H | 2-pyridylmethyl | 143–6 | |
| 9 | 5-Br | H | 3-pyridylmethyl | 168–70 | |
| 10 | H | Et | Pr$^n$ | gum | |
| 11 | H | Et | 2-pyridylmethyl | gum | |
| 12 | H | Et | 3-pyridylmethyl | 97–101 | |
| 13 | H | Et | $CH_2CH_2OH$ | gum | |
| 14 | 5-MeS | Et | Pr$^n$ | gum | |
| 15 | 5-MeS | Et | 3-pyridylmethyl | gum | |
| 16 | 5-Br | Et | $CH_2CH_2OH$ | gum | |

Footnote a) $^1$H-NMR (DMSO-$d_6$) δ: 1.11 (t, 3H, J=6.7Hz), 3.58 (q, 2H, J=6.7Hz), 4.47 (d, 2H, J=5Hz), 4.77 (s, 2H), 5.19 (s, 2H), 6.63 (d, 1H, J=9Hz), 7.03–7.12 (m, 2H), 7.31–7.51 (m, 5H), 7.7–7.76 (m, 1H), 7.94 (dd, 1H, J=9Hz, J=3Hz), 8.41–8.63 (m, 3H), 8.8 (t, 1H, J=6Hz).

TABLE 2b

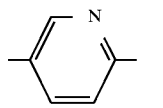

| Compound No. | R | R¹ | Het | R² | mp (°C.) |
|---|---|---|---|---|---|
| 1 | 5-Br | Et | 2,5-pyridyl | 3-pyridylmethyl | 108–110 |

TABLE 2b-continued

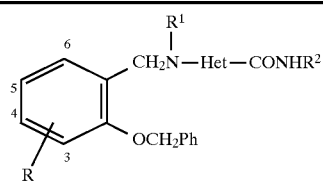

| Compound No. | R | R¹ | Het | R² | mp (°C.) |
|---|---|---|---|---|---|
| 2 | H | Et | " | -CH₂-(2-pyridyl) | gum |
| 3 | 5-Br | Et | thiazolyl | -CH₂CH=CH₂ | 137 |
| 4 | 5-Br | Et | thiazolyl | Pr$^n$ | gum |
| 5 | 5-Br | Et | " | CH₂CH₂OH | 135 |
| 6 | 5-Br | Et | " | -CH₂-(2-pyridyl) | gum |
| 7 | 5-Br | Et | " | -CH₂-(2-pyridyl) | gum |
| 8 | 5-Br | Et | methyloxazolyl | -CH₂-(2-pyridyl) | 90–92 |
| 9 | 5-Br | Et | " | -CH₂CH₂OH | gum |
| 10 | 5-Br | Et | thiazolyl | -CH₂CN | 185.5–188.0 |

TABLE 2c

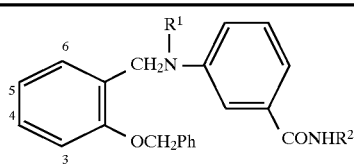

| Compound No. | R | R¹ | R² | mp (°C.) |
|---|---|---|---|---|
| 1 | H | Et | Pr$^n$ | 83 |
| 2 | H | Et | -CH₂CH₂OH | 95 |
| 3 | H | Et |  -CH₂-(2-pyridyl) | 88 |

TABLE 2c-continued

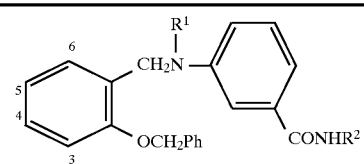

| Compound No. | R | R¹ | R² | mp (°C.) |
|---|---|---|---|---|
| 4 | H | Et | -CH₂-(2-pyridyl) | 88 |
| 5 | 5-Br | Et | Pr$^n$ | 103 |

TABLE 2c-continued

Structure: benzyl with OCH2Ph at position 3, CH2N(R¹) linked to phenyl-CONHR², with positions 3,4,5,6 on benzyl ring; R on ring.

| Compound No. | R | R¹ | R² | mp (°C.) |
|---|---|---|---|---|
| 6 | 5-Br | Et | —CH₂-(2-pyridyl) | 118 |
| 7 | 5-Br | Et | —CH₂-(pyridyl) | 146 |
| 8 | 5-Br | Et | CH₂CH₂OH | 121 |
| 9 | H | Et | —CH₂-(pyridyl) | 136 |
| 10 | H | Et | —NH-(2-pyridyl) | 123 |
| 11 | H | Et | —N(piperidinyl) | 147 |
| 12 | H | Et | —N(morpholinyl) | 135 |
| 13 | H | Et | —N(pyrrolidinyl) | 152 |

TABLE 2d

Structure: benzyl ring with OCH₂Ph at position 2, R at position 3; CH₂N(Et) linked to phenyl-CONHR¹ with OMe at position 2 or 3.

| Compound No. | R | R¹ | Position of MeO | mp (°C.) |
|---|---|---|---|---|
| 1 | H | Prⁿ | 2 | gum |
| 2 | H | —CH₂-(pyridyl) | 2 | gum |

TABLE 2e

Structure: benzyl with OCH₂Ph at ortho, R at 5-position; CH₂N(Et)(O⁻) linked to phenyl-CONHCH₂-(2-pyridyl).

| Compound No. | R | mp (°C.) |
|---|---|---|
| 1 | 5-MeSO₂ | 134 |

TABLE 2f

Structure: naphthyl with OCH₂Ph, CH₂N(R) linked to pyridyl-CONHR¹.

| Compound No. | R | R¹ | mp (°C.) |
|---|---|---|---|
| 1 | Et | —CH₂-(2-pyridyl) | 198 |

TABLE 2g

Structure: thiadiazole bearing OCH₂Ph and CH₂N(Et) linked to phenyl-CONHR.

| Compound No | R | mp (0°C.) | Footnote |
|---|---|---|---|
| 1 | CH₂CH₂CH₃ | gum | a |
| 2 | —CH₂-(2-pyridyl) | 118–120 | a |
| 3 | —CH₂-(pyridyl) | gum | a |

Footnote
a) For starting material see Table 1f compound 2.

TABLE 3
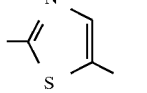
| Compound No. | R | R¹ | Ar | R² | mp (°C.) |
|---|---|---|---|---|---|
| 1 | 5-Br | Et |  | 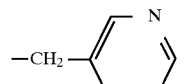 | gum |
| 2 | 5-Br | Et | " |  | gum |
| 3 | 5-Br | Et | " | —CH₂CH₂OH | 145 |
| 4 | 5-Br | Et | " | 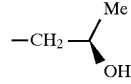 | 141 |
| 5 | 5-Br | Et | " | 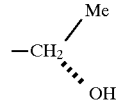 | 135 |
TABLE 3a
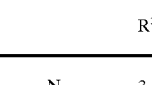
| Compound No. | R | R¹ | R² | R³ | mp (°C.) |
|---|---|---|---|---|---|
| 1 | 5-Br | Et |  | 3-MeO | 98 |
| 2 | 5-Br | Et | 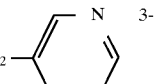 | 3-MeO | 110 |

TABLE 4
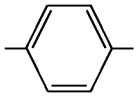
| Compound No. | R | R¹ | Ar | R² | mp (°C.) |
|---|---|---|---|---|---|
| 1 | H | Et | 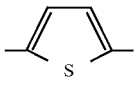 | SO$_2$Ph | 73 |
| 2 | 5-Br | Et |  | SO$_2$Ph | 65 |
| 3 | 4-Br | Et | 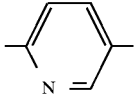 | SO$_2$Ph | 105–7 |
| 4 | 5-Br | Et | 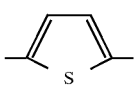 | SO$_2$Ph | gum |
| 5 | 5-Br | Et | 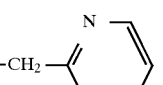 | 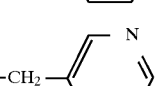 | gum |
| 6 | 5-Br | Et | " | 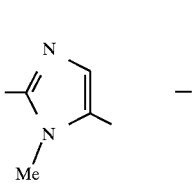 | gum |
| 7 | 5-Br | Et | 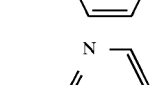 | 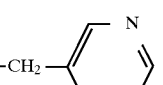 | gum |
| 8 | 5-Br | Et | " | 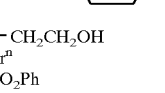 | gum |
| 9 | 5-Br | Et | " | —CH$_2$CH$_2$OH | 104 |
| 10 | 5-Br | Et | " | Pr$^n$ | gum |
| 11 | 5-Br | Et | " | SO$_2$Ph | gum |
| 12 | 5-Br | Et | 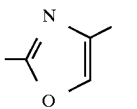 | CH$_2$CH$_2$CH$_3$ | 113–114 |
| 13 | 5-Br | Et | " | CH$_2$CH$_2$OMe | 113–114 |

TABLE 5

| Compound No. | R | R¹ | mp (°C.) |
|---|---|---|---|
| 1 | H | H | 115 |
| 2 | H | Et | 163 |
| 3 | 5-Br | H | foam |
| 4 | 5-Br | Et | 168 |

TABLE 5a

| Compound No | R | m.p. (°C.) | Footnote |
|---|---|---|---|
| 1 | Et | 148–150 | a |

Footnote
a) The product was purified by MPLC eluting with methanol/dichloromethane (5:95).
$^1$H-NMR (DMSO-d6): δ 1.13 (t, 3H, J=7.9Hz), 3.52 (q, 2H, J=7.9Hz) 4.78 (s, 2H), 5.19 (s, 2H), 6.78 (d, 1H, J=8.3Hz), 7.08 (d, 1H, J=1.7Hz), 7.11 (d, 1H, J=8.3), 7.28–7.51 (m, 6H), 8.02 (dd, J=8.3Hz, 2.1Hz), 8.70 (d, J=2.1Hz).
MS (FAB$^+$) = 465 [M + H]$^+$.

Preparation of starting materials is in Reference Example 27.

TABLE 5b

| Compound No. | R¹ | Het | R² | mp (°C.) | Footnote |
|---|---|---|---|---|---|
| 1 | Br | pyridyl | CH₂CH₂CH₃ | — | a |
| 2 | Br | " | thiadiazole-NHCOMe | 196–197° C. | b |
| 3 | Br | " | thienyl-pyridyl | 195–196° C. | c |
| 4 | Br | " | isoxazole (3,5-diMe) | 181.5–183° C. | d |
| 5 | Br | " | CH₂CH₂OH | 124–124.5° C. | e |
| 6 | SO₂Me | " | CH₂Ph | 176–179° C. | f |
| 7 | Br | " | pyrazole (1,3,5-triMe) | 167–169° C. | |

TABLE 5b-continued

R¹—[benzene with OCH₂Ph]—CH₂N(Et)—(Het)—CONHSO₂R²

| Compound No. | R¹ | Het | R² | mp (°C.) | Footnote |
|---|---|---|---|---|---|
| 8 | Br | " | [5-chloro-2-thienyl] | — | |
| 9 | Br | " | [4-fluorophenyl] | 209–211° C. | |
| 10 | Br | " | [tetrahydrothiophene-3-yl sulfone] | 114.5–116.5° C. | g |
| 11 | Br | [pyridazine] | [5-(2-pyridyl)-2-thienyl] | 226–227° C. | |
| 12 | Br | " | [5-acetamido-1,3,4-thiadiazol-2-yl] | — | h |
| 13 | H | [pyridine] | CH₂CH₂OH | 67.5–68° C. | |
| 14 | Br | [pyridazine] | CH₂CH₂OEt | — | |
| 15 | Br | " | [5-chloro-2-thienyl] | 127–130° C. | |
| 16 | Br | " | CH₃ | — | i |
| 17 | SO₂Me | " | CH₂Ph | — | |
| 18 | Br | " | Et | — | |
| 19 | Br | " | [3,5-dimethylisoxazol-4-yl] | 78.6–80.7° C. | j |

Footnotes a) ¹H NMR (CDCl₃): δ 10–1.12 (t, 3H, J=6.7Hz); 1.15–1.25 (t, 3H); 1.8–2.0 (m, 2H); 3.5–3.7 (m, 4H); 4.75 (s, 2H); 5.1 (s, 2H); 6.4 (d, 1H); 6.82 (d, 1H); 7.1 (s, 1H); 7.3–7.45 (m, 6H); 7.8–7.9 (d of d, 1H); 8.6 (s, 1H); 8.7–8.8 (broad s, 1H).
MS: 546 (MH)⁺
b) ¹H NMR (CDCl₃): δ 1.0–1.2 (t, 3H); 2.2–2.3 (s, 3H); 3.3–3.7 (q, 2H); 4.8 (s, 2H); 5.1–5.2 (s, 2H); 6.6–6.75 (d, 1H); 7.1–7.2 (d, 1H); 7.2–7.3 (d, 1H); 7.3–7.5 (m, 6H); 7.9–8.05 (m, 1H); 8.4–8.5 (s, 1H).
c) ¹H NMR (CDCl₃ + DMSO-d₆); δ 1.1–1.45 (t, 3H); 3.55–3.7 (q, 2H); 4.45–4.6 (s, 2H); 5.05–5.15 (s, 2H); 6.35–6.45 (d, 1H); 6.8–6.9 (d, 1H); 7.05–7.15 (d, 1H); 7.2–7.4 (m, 8H); 7.5–7.55 (d, 1H); 7.65–7.75 (m, 2H); 7.85–8.00 (m, 2H); 8.5–8.6 (d, 1H); 8.7–8.8 (d, 1H); 11.84 (s, 1H).
MS: 663 (MH)⁺
d) ¹H NMR (CDCl₃): δ 1.1–1.2 (t, 3H); 2.4–2.5 (s, 3H); 2.75–2.85 (s, 3H); 3.55–3.7 (q, 2H); 4.7–4.8 (s, 2H); 5.05–5.1 (s, 2H); 6.35–6.45 (d, 1H); 6.80–6.90 (d, 1H); 7.1 (d, 1H); 7.25–7.45 (m, 6H); 7.7–7.8 (m, 1H); 8.5 (d, 1H).
MS: 599 (MH)⁺
e) ¹H NMR (CDCl₃): δ 1.1–1.3 (t, 3H); 3.5–3.7 (m, 4H); 4.65–4.80 (m, 4H); 4.9 (s, 2H); 5.1 (s, 2H); 6.4 (d, 1H); 6.8 (d, 1H); 7.1 (s, 1H); 7.25–7.42 (m, 6H); 7.9 (d of d, 1H); 8.8 (s, 1H).

TABLE 5b-continued

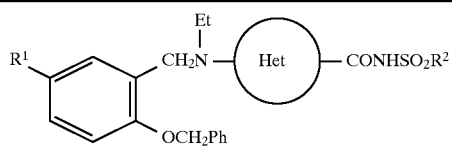

| Compound No. | R¹ | Het | R² | mp (°C.) | Footnote |
|---|---|---|---|---|---|

MS: 548 (MH)⁺
f) ¹H NMR (CDCl₃): δ 1.1–1.3 (t, 3H); 2.9 (s, 3H); 3.55–3.70 (q, 2H); 4.7–4.8 (s, 2H); 4.85–4.90 (s, 2H); 5.15–5.2 (s, 2H); 6.4–6.5 (d, 1H); 7.05–7.15 (d, 1H); 7.25–7.5 (m, 10H); 7.6 (d, 1H); 7.7–7.7 (m, 2H); 8.5 (d, 1H).
MS: 593 (MH)⁺
g) ¹H NMR (CDCl₃): δ 1.1–1.3 (m, 3H); 2.6–2.8 (m, 2H); 3.0–3.2 (m, 1H); 3.3–3.4 (m, 1H); 3.4–3.55 (m, 2H); 3.56–3.7 (q, 2H); 4.6–4.8 (m, 3H); 5.0–5.1 (s, 2H); 6.4–6.6 (d, 1H); 6.8–6.9 (d, 1H); 7.1–7.2 (d, 1H); 7.3–7.45 (m, 6H); 7.8–8.0 (m, 1H); 8.7 (d, 1H).
MS: 622 (MH)⁺
h) ¹H NMR (DMSO-d₆): δ 1.0–1.15 (t, 3H); 2.21 (s, 3H); 3.5–3.7 (q, 2H); 4.8 (s, 2H); 5.1 (s, 2H); 7.05–7.15 (d, 1H); 7.2–7.4 (m, 6H); 7.4–7.56 (m, 2H); 7.8–7.9 (d, 1H); 12.87 (s, 1H).
MS: 630 (MH)⁺
i) ¹H NMR (DMSO-d₆): δ 1.12 (t, 3H, J = 6.7Hz); 3.35 (s, 3H); 3.69 (q, 2H, J = 6.7Hz); 4.86 (s, 2H); 5.15 (s, 2H); 7.06–7.2 (m, 3H); 7.28–7.45 (m, 6H); 7.78 (d, 1H, J = 8.5Hz).
j) ¹H NMR (CDCl₃): δ 1.2–1.3 (t, 3H); 2.49 (s, 3H); 2.81 (s, 3H); 3.7–3.8 (q, 2H); 4.8 (s, 2H); 5.1 (s, 2H); 6.7–6.75 (d, 1H); 6.87–6.91 (d, 1H); 7.13 (d, 1H); 7.3–7.42 (m, 6H); 7.7–7.8 (d, 1H).
MS: 600 (MH)⁺

TABLE 6

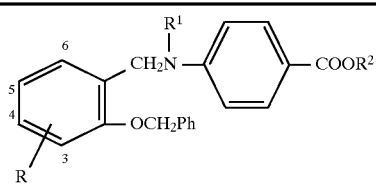

| Compound No. | R | R¹ | R² | mp (°C.) | Footnote |
|---|---|---|---|---|---|
| 1 | 5-Br | H | Me | 115–6 | |
| 2 | 5-MeS | H | Et | 62 | |
| 3 | 5-Br | H | Buᵗ | — | |
| 4 | H | H | Et | gum | |
| 5 | 5-MeSO₂— | H | Me | 124 | |
| 6 | 5-CN | H | Me | 118 | a |
| 7 | 5-Me | H | Me | gum | b |
| 8 | 5-MeO— | H | Me | gum | |
| 9 | 5-Br | H | Me | 108 | |
| 10 | 4-Br | H | Me | — | |
| 11 | 6-Br | H | Me | gum* | |
| 12 | 4-MeO— | H | Me | — | |
| 13 | 4-Me | H | Me | gum | |
| 14 | 5-MeSO | H | Me | — | |

Footnote
a. 5-cyano-5-hydroxybenzaldehyde was prepared as described in Chem. Pharma. Bull. 31, 1751 (1983).
b. 5-methyl-2-hydroxybenzaldehyde was prepared as described in J. Chem. Soc. 1933. 496.

TABLE 6a

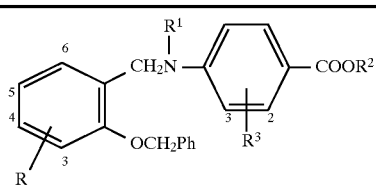

| Compound No. | R | R¹ | R² | R³ | mp (°C.) | Footnote |
|---|---|---|---|---|---|---|
| 1 | 5-Br | H | Et | 3-OH | 121 | a |
| 2 | H | H | tBu | 2-F | — | |

TABLE 6a-continued

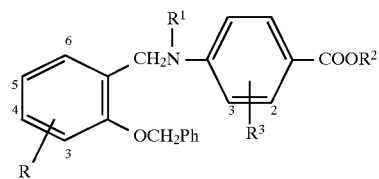

| Compound No. | R | R¹ | R² | R³ | mp (°C.) | Footnote |
|---|---|---|---|---|---|---|

Footnote
a. ethyl 4-amino-3-hydroxybenzoate (CA 107 39428y) was prepared by reducing ethyl 4-nitro-3-hydroxybenzoate with hydrogen over 10% palladium on carbon. The nitro compound was prepared by esterifying 4-nitro-3-hydroxybenzoic acid with ethanol in the presence of H₂SO₄.

TABLE 6b

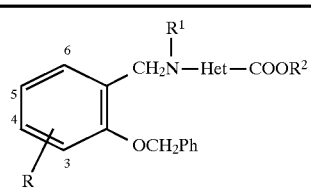

| Compound No. | R | R¹ | Het | R² | mp (°C.) | Footnote |
|---|---|---|---|---|---|---|
| 1 | H | H | (pyridine) | Et | 118 | a |
| 2 | 5-Br | H | (thiazole) | | 128 | b |

TABLE 6b-continued

![structure: benzene ring with CH₂N(R¹)–Het–COOR² at position 6, OCH₂Ph at position 2, R at position 3]

| Compound No. | R | R¹ | Het | R² | mp (°C.) | Footnote |
|---|---|---|---|---|---|---|
| 3 | 5-Br | H | (thiazole, N=C–S) | Et | 124 | c |
| 4 | 5-Br | H | (pyridine N) | Me/Et | — | d |
| 5 | 5-Br | H | (N-methylimidazole) | Me | — | e |

Footnote
a) methyl 3-aminopyrid-6-ylcarboxylate can be prepared using a similar method to that described in J. Med. Chem. 1991, 34, 1594.
b) ethyl 2-aminothiazol-5-ylcarboxylate was prepared from thiourea and ethyl chloroacetate.
c) ethyl 2-aminothiazol-4-ylcarboxylate can be prepared using the method described in J.O.C., 55, 728, 1990 or J. Het. Chem., 1003 (1991).
d) methyl 2-aminopyrid-5-ylcarboxylate can be prepared using a similar method to that described in Tet. Lett. 31, 5757, 1990 or USP 4141977.

$^1$H-NMR: (DMSO-d$_6$): δ3.76 (s, 3H), 4.57 (d, 2H, J=7 Hz), 5.17 (s, 2H), 6.59 (d, 1H, J=9 Hz), 7.04 (d, 1H, J=8 Hz), 7.30–7.49 (m, 7H), 7.77 (t, 1H, J=7 Hz), 7.83 (dd, 1H, J=9 Hz, J=2.5 Hz), 8.55 (d, 1H, J=2.5 Hz). See Reference Example 12.

e) Preparation of ethyl 2-amino-1-methyl-1H-imidazole-5-carboxylate:

Sarcosine ethyl ester hydrochloride (76 g) was added to a solution of sodium formate (37 g) dissolved in formic acid (163 ml) and the mixture was stirred at ambient temperature for 4 hours and filtered. Acetic anhydride (222 ml) was added dropwise to the filtrate (exotherm to 60° C.) and the mixture was allowed to stand at ambient temperature for 10 hours. The solvent was evaporated and the residue was triturated with acetone and the NaCl was filtered. The solvent was evaporated and the residue was distilled under high vacuum to give ethyl N-formyl sarcosine ester 50.6 g, bp 80°–82° C. at 0.05 0.05 mmHg.

Potassium-t-butoxide (52.3 g) was suspended in diethylether (500 ml) and cooled to 0° C. A solution of N-formyl sarcosine ether ester (67.66 g) and methyl formate (27.9 g) in diethylether (200 ml) was added dropwise over 30 minutes and the mixture was stirred at 0° C. for 1 hour. The solid product was filtered (76.6 g) and used immediately for the next stage. The ethyl-2-(N-formyl-N-methyl)-3-oxopropionate prepared as described above was dissolved in water and concentrated HCl (138 ml) was added. The mixture was heated on a steam bath for 30 minutes, cooled and the pH was adjusted to 5 by addition of concentrated NaOH. Cyanamide (19.3 g) was added and the mixture was heated at 100° C. for 1 hour. The mixture was allowed to cool and was basified with concentrated aqueous ammonium hydroxide, the solid was filtered, washed with water and dried under reduced pressure and was crystallised from EtOAc (300 ml) to give ethyl 2-amino-1-methyl-1H-imidazole-5-carboxylate yield 14.6 g.

Methyl 2-amino-1-methyl-1H-imidazol-5-carboxylate and the corresponding ethyl ester may be prepared using the method described in J. Med. Chem 1972, 15, 1086.

TABLE 6c

![structure: benzene ring with CH₂NH–Ar–R¹ at position 6, OCH₂Ph at position 2, R at position 3]

| Compound No. | R | Ar | R¹ | mp (°C.) | Footnote |
|---|---|---|---|---|---|
| 1 | 5-Br | (pyridine N) | CO₂Et | 118 | a |
| 2 | 5-Br | (thiazole N–S) | CO₂Et | 128 | b |
| 3 | 5-Br | (pyridine N) | CO₂Me | — | c |
| 4 | 5-Br | (thiazole N–S) | CO₂Et | 124 | d |

TABLE 6c-continued

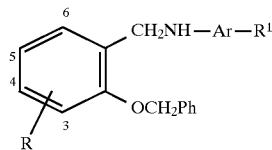

| Compound No. | R | Ar | R¹ | mp (°C.) | Footnote |
|---|---|---|---|---|---|
| 5 | 5-Cl | (pyridine) | $CO_2Me$ | gum | c, e |
| 6 | 5-MeS | " | $CO_2Me$ | — | c |
| 7 | 5-MeSO$_2$ | " | $CO_2Me$ | — | c |
| 8 | 5-Br | (N-methyl pyrazole) | $CO_2Et$ | 68 | e, f |
| 9 | H | (phenyl) | $CO_2Et$ | gum | |
| 10 | 5-Br | (phenyl) | $CO_2Et$ | 92 | |
| 11 | 5-Br | (phenyl) | $CH_2CO_2Et$ | 73 | |
| 12 | 5-Br | (phenyl) | $CONHCH_2CH_2CH_3$ | 164–5 | g |
| 13 | 5-Br | (thiadiazole N=N) | $CONHCH_2CH_2CH_3$ | | g, h |

Footnote
a. see Table 6b footnote a
b. see Table 6b footnote b
c. see Table 6b footnote d
c. see Table 6b footnote c
e. imine made by azeotropic removal of water with toluene
f. see Table 6b footnote e
g. 2-amino-5-(N-propylcarbamoyl)-1,3,4-thiadiazole was prepared according to. Prakt Chem. 331, 243, (1989), ibid 332, 55, (1990).

TABLE 6d

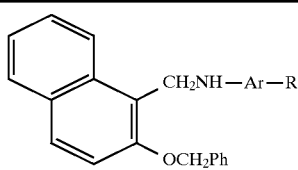

| Compound No. | R | Ar | mp (°C.) | Footnote |
|---|---|---|---|---|
| 1 | $CO_2Me$ |  | 119 | a |

Footnote
a imine made by azeotropic removal of water with toluene.

TABLE 6e

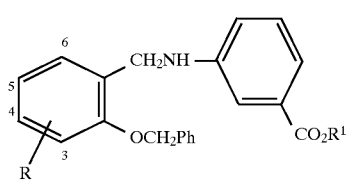

| Compound No. | R | R¹ | mp (°C.) |
|---|---|---|---|
| 1 | H | Et | — |
| 2 | 5-Br | Et | 92 |

TABLE 6f

[Structure: R-substituted benzyl with OCH2Ph, CH2N(R)-phenyl-CN]

| Compound No. | R | R¹ | mp (°C.) |
|---|---|---|---|
| 1 | H | H | |
| 2 | H | Et | |
| 3 | Br | H | 101 |
| 4 | Br | Et | |

TABLE 7

[Structure: R-substituted benzyl with OCH2Ph at position 3, CH2N(R¹)-phenyl-COOR²]

| Compound No. | R | R¹ | R² | mp (°C.) |
|---|---|---|---|---|
| 1 | 5-Br | H | Me | |
| 2 | 5-MeS | H | Me/Et | |
| 3 | H | H | Me | |

TABLE 7a

[Structure: R-substituted benzyl with OCH2Ph, CH2N(R¹)-phenyl substituted with R², R³]

| Compound No. | R | R¹ | R² | R³ | mp (°C.) | Footnote |
|---|---|---|---|---|---|---|
| 1 | 5-Br | H | 1-CO₂tBu | 2-F | | |

TABLE 7b

[Structure: naphthalene with OCH2Ph, CH2N(R)-Ar-COOMe]

| Compound No. | R | Ar | mp (°C.) | Footnote |
|---|---|---|---|---|
| 1 | H | pyridine | 129 | a |

Footnote
a see table 6b, footnote d.

TABLE 7c

[Structure: R-substituted benzyl with OCH2Ph at position 3, CH2N(R¹)-Het-R²]

| Compound No. | R | R¹ | Het | R² | mp (°C.) | Footnote |
|---|---|---|---|---|---|---|
| 1 | H | H | thiophene | CO₂Et | | a |
| 2 | 5-Br | H | thiazole | CO₂Et | 124 | b |
| 3 | 5-I | H | pyridine | CO₂Me | | c, d |
| 4 | 5-MeS | H | pyridine | CO₂Et | gum | d |
| 5 | 5-Cl | H | " | CO₂Me | gum | d |

TABLE 7c-continued

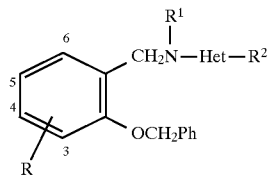

| Compound No. | R | R¹ | Het | R² | mp (°C.) | Footnote |
|---|---|---|---|---|---|---|
| 6 | 5-MeSO₂ | H | " | CO₂Me | gum | d |
| 7 | 5-Br | H | " | CO₂Et/Me | gum | d, e |
| 8 | 5-Br | H | 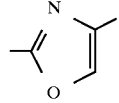 | CO₂Et | 153–154 | f |

Footnotes
a Preparation of ethyl 5-(t-butoxycarbonylamino)thiophene-carboxylate:
Ethyl thiophene-2-carboxylate (50 g) in THF (500 ml) was added dropwise to a solution of lithium diisipropylamide prepared at −78° C. from diisopropylamine (32 g) and n-BuLi (200 ml of a 1.6M solution in hexanes) at such a rate that the internal temperature did not exceed −60° C. The mixture was stirred at −78° C. for 30 minutes. Freshly crushed solid carbon dioxide (50 g) was added and the mixture was allowed to warm to ambient temperature. The solvent was evaporated and the residue was dissolved in water (500 ml) and acidified with 2N HCl, the solid product was filtered and dried under reduced pressure to give monoethyl ester of thiophene 2,5-dicarboxylic acid, yield 44 g.
Diphenylphosphoryl azide (62.3 g) was added to a mixture of the monoethyl ester of 2,5-thiophenedicarboxylic acid (45 g), triethylamine (21 g) and t-butanol (50 ml) in THF (200 ml) and the mixture was heated under reflux for 18 hours. The reaction mixture was allowed to cool and was evaporated to dryness. The residue was dissolved in EtOAc (500 ml) and was washed consecutively with aqueous 5% citric acid (3 × 10 ml) and aqueous sodium bicarbonate (3 × 100 ml) and was dried (MgSO₄). The residue obtained on removal of the solvent was subjected to chromatography on silica, eluting with dichloromethane to give ethyl 5-(t-butoxycarbonylamino) thiophenecarboxylate which was used in subsequent steps without further purification.
b see Table 6b footnote c
c 5-iodo-2-hydroxybenzaldehyde may be prepared as described in Beilstein, 8, 56.
d see Table 6b footnote d
e prepared from methyl 2-amino-5-pyridine carboxylate as a mixture of methyl and ethyl esters.
f ethyl 2-amino-4-oxazolecarboxylate may be prepared as described in J. Med Chem 1971, 14, 1076.

TABLE 8

| Compound No. | R | R¹ | R² | mp (°C.) | Footnote |
|---|---|---|---|---|---|
| 1 | 4-Br | Et | Me | — | |
| 2 | 6-Br | Et | Me | — | |
| 3 | 4-MeO | Et | Me/Et | — | a |
| 4 | 4-Me | Et | Me/Et | — | a |
| 5 | 5-Br | Me | Me | 220–5 | |
| 6 | 5-Br | Et | Me | 215–20 | |
| 7 | 5-Br | Ph-CH₂— | Me | 104–7 | |
| 8 | 5-Br | —CH₂-(3-pyridyl) | Me | 215 | |
| 9 | 5-MeS | Et | Me | — | |
| 10 | 5-MeSO | Et | Me | — | |
| 11 | 5-CN | Et | Me | — | |
| 12 | 5-MeSO₂ | Et | Me | 154 | b |
| 13 | 5-Br | Prⁿ | Me | 117 | |
| 14 | 5-Me | Et | Me | — | |

TABLE 8-continued

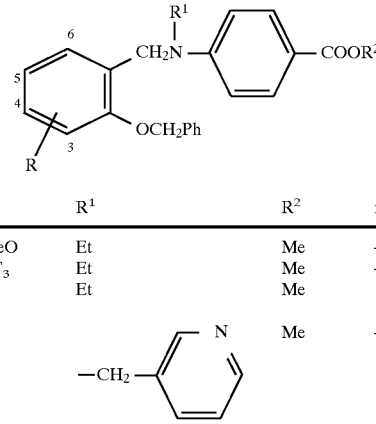

| Compound No. | R | R¹ | R² | mp (°C.) | Footnote |
|---|---|---|---|---|---|
| 15 | 5-MeO | Et | Me | — | |
| 16 | 5-CF₃ | Et | Me | — | |
| 17 | H | Et | Me | 83–5 | |
| 18 | 5-Br | —CH₂-(3-pyridyl) | Me | — | |

Footnote
a) Me/Et indicates a mixture of methyl and ethyl esters
b) ¹H-NMR (DMSO-d₆): δ 1.13 (t, 3H, J=8Hz) 3.03 (s, 3H), 3.53 (q, 2H, J=8Hz), 3.73 (s, 3H), 4.61 (s, 2H), 5.31 (s, 2H), 6.66 (d, 2H, J=9.0Hz), 7.34–7.53 (m, 7H), 7.71 (d, 2H, J=9Hz), 7.81 (dd, 1H, J=8.5Hz, J=2.5Hz).
See reference Examples 3 and 19.

TABLE 8a

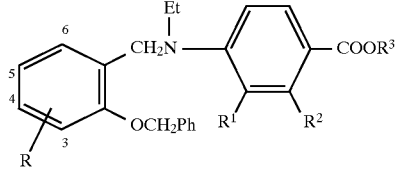

| Compound No. | R | R¹ | R² | R³ | mp (°C.) |
|---|---|---|---|---|---|
| 1 | H | H | MeO | Me | — |
| 2 | H | H | F | t-Bu | 154 |
| 3 | 5-Br | H | F | t-Bu | 104 |
| 4 | 5-Br | NO₂ | H | Et | 98 |
| 5 | 5-Br | MeO | H | Et | — |

TABLE 8b

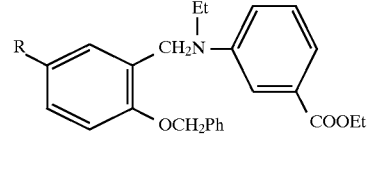

| Compound No. | R | mp (°C.) | Footnote |
|---|---|---|---|
| 1 | H | — | a |
| 2 | Br | gum | a |

TABLE 8c

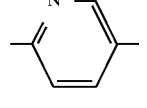

| Compound No. | R | R¹ | R² | Het | mp (°C.) | Footnote |
|---|---|---|---|---|---|---|
| 1 | 5-Br | Et | Me/Et | 2,5-pyridyl | — | a |
| 2 | 5-Br | Me | Me | " | gum | b |
| 3 | H | Et | Me/Et | " | — | c |

TABLE 8c-continued

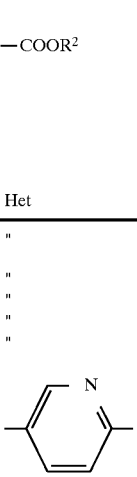

| Compound No. | R | R¹ | R² | Het | mp (°C.) | Footnote |
|---|---|---|---|---|---|---|
| 4 | 5-Br | HC≡CCH₂— | Me | " | — | |
| 5 | 5-I | Et | Me | " | — | |
| 6 | 5-Cl | Et | Me | " | — | |
| 7 | 5-MeS | Et | Me/Et | " | — | |
| 8 | 5-MeSO | Et | Me | " | — | |
| 9 | 5-Br | Et | Et |  | 115–8 | |
| 10 | 5-Br | Et | Et | 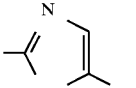 | — | |
| 11 | 5-Br | Et | Et | 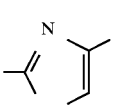 | — | |
| 12 | 5-Br | Et | Et | 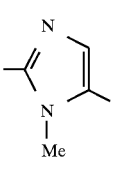 | 79 | |
| 13 | 5-Br | Et | Et | 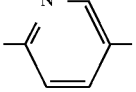 | — | |
| 14 | H | Et | Et | 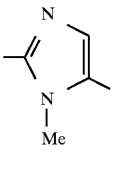 | — | |
| 15 | 5-NO₂ | Et | Et | " | — | |
| 16 | 5-Br | —CH₂ | Et | 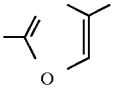 | — | |
| 17 | 5-Br | Et | Et | | 73-74 | d |

Footnote
a) ¹H-NMR (DMSO-d₆) δ: 1.1 (t, 3H, J=6.7Hz), 1.29 (t, 3H, J=6.7Hz), 3.59 (q, 2H, J=6.7Hz), 4.26 (q, 2H, J=6.7Hz), 4.77 (s, 2H), 5.19 (s, 2H), 6.64 (d, 1H, J=8.3Hz), 7.06–7.14 (m, 2H), 7.31–7.50 (m, 6H), 7.9 (dd, J=8.3Hz, J=2.6Hz), 8.62 (d, J=2.6Hz).
See Table 6b, compound 4.
b) ¹H-NMR (DMSO-d₆): δ3.11 (s, 3H), 3.78 (s, 3H), 4.83 (s, 2H), 5.17 (s, 2H), 6.67 (d, 1H, J=8.5Hz), 7.0–7.1 (m, 2H), 7.3–7.5 (m, 6H), 7.88–7.95 (m, 1H), 8.62 (d, 1H, J=2.5Hz).
See Table 6b, compound 4.
c) ¹H-NMR (DMSO-d₆): δ1.12 (t, 3H, 6.5Hz), 1.29 (t, 2H, 6.5Hz), 3.60 (q, 2H, J=6.5Hz), 3.78 (s, 1H), 4.25 (q, 4/3H, 6.5Hz), 4.78 (s, 2H), 5.18 (s, 2H), 6.60 (d, 1H, J=8.5Hz), 6.85–7.5 (m, 9H), 7.85 (dd, 1H, J=8.5Hz, 5 = 2.5Hz), 8.62 (d, 1H, J=2.5Hz).

TABLE 8c-continued

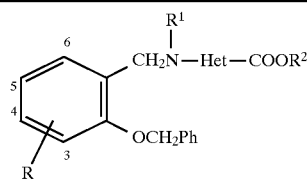

| Compound No. | R | R¹ | R² | Het | mp (°C.) | Footnote |
|---|---|---|---|---|---|---|

See Reference Example 25.
d) ¹H-NMR (CDCl₃): δ1.13 (t, 3H, J=6.5Hz), 1.35 (t, 3H, J=7Hz), 3.48 (q, 2H, J=6.5Hz), 4.35 (q, 2H, J=7Hz), 4.66 (s, 2H), 5.29 (s, 2H), 6.81 (d, 1H, J=8.5Hz), 7.25–7.42 (m, 7H), 7.68 (s, 1H).

TABLE 8d

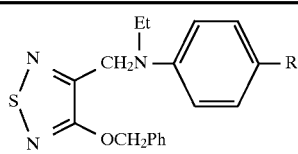

| Compound No. | R | mp (°C.) | Footnote |
|---|---|---|---|
| 1 | CO₂Me | gum | |

TABLE 9

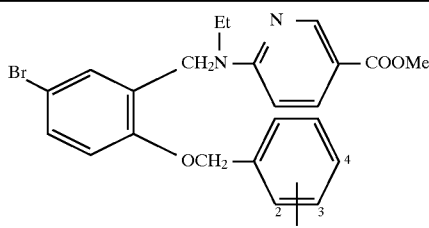

| Compound No. | R | X | MS |
|---|---|---|---|
| 1 | 4-Cl | Cl | |
| 2 | 4-CF₃ | Br | |
| 3 | 3-CN | Br | |
| 4 | 4-F | Br | CI⁺: 473/475 (MH)⁺ |
| 5 | 4-butyl | Cl | FAB⁺: 511/513 (MH)⁺ |
| 6 | 4-OCF₃ | Br | CI⁺: 539/541 (MH)⁺ |

We claim:

1. A compound of the formula (I)

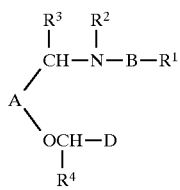

wherein:

A is optionally substituted phenyl; provided that the —CH(R³)N(R²)B—R¹ and —OCH(R⁴)—D linking groups are positioned in a 1,2 relationship to one another on ring carbon atoms and the ring atom positioned ortho to the —OCHR⁴— linking group (and therefore in the 3-position relative to the —CHR³NR²— linking group) is not substituted;

B is optionally substituted pyridazinyl or pyridazinone;

D is phenyl optionally substituted by 1 or 2 substituents selected from halo, trifluoromethyl, nitro, hydroxy, amino, $C_{1-4}$alkylamino, di($C_{1-4}$alkyl)amino, cyano, $C_{1-6}$alkoxy, —S(O)$_p$$C_{1-4}$alkyl (p is 0, 1 or 2), $C_{1-4}$alkanoyl, $C_{1-6}$alkyl, $C_{3-7}$cycloalkyl, $C_{3-7}$cycloalkyl$C_{1-3}$alkyl, $C_{3-7}$cycloalkyl$C_{2-3}$alkenyl, $C_{5-7}$cycloalkenyl, $C_{5-7}$cycloalkenyl$C_{1-3}$alkyl, $C_{5-7}$cycloalkenyl$C_{2-3}$alkenyl, wherein $C_{3-7}$cycloalkyl, $C_{5-7}$cycloalkenyl, $C_{1-6}$alkyl and $C_{1-6}$alkoxy are optionally substituted by trifluoromethyl, hydroxy, halo, nitro, cyano or amino;

R¹ is positioned on ring B in a 1,3 or 1,4 relationship with the —CH(R³)N(R²)— linking group and is carboxy, carboxy$C_{1-3}$alkyl, tetrazolyl, tetrazolyl$C_{1-3}$alkyl, tetronic acid, hydroxamic acid, sulphonic acid, or R¹ is of the formula (IIA), (IIB) or (IIC):

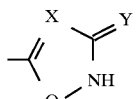 (IIA)

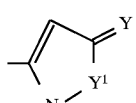 (IIB)

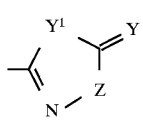 (IIC)

wherein X is CH or nitrogen, Y is oxygen or sulphur, Y¹ is oxygen or NH, and Z is CH₂, NH or oxygen provided that there is no more than one ring oxygen and there are at least two ring heteroatoms;

or R¹ is of the formula —CONR$^a$R$^{a1}$ or —$C_{1-3}$alkylCONR$^a$R$^{a1}$ wherein R$^a$ is hydrogen, $C_{1-6}$alkyl, $C_{3-7}$cycloalkyl, $C_{3-7}$cycloalkyl$C_{1-3}$alkyl, $C_{5-7}$cycloalkenyl or $C_{5-7}$cycloalkenyl$C_{1-3}$alkyl and R$^{a1}$ is hydrogen, hydroxy or optionally substituted: $C_{1-10}$alkyl, $C_{2-10}$alkenyl, $C_{2-10}$alkynyl, $C_{3-7}$cycloalkyl, $C_{3-7}$cycloalkyl$C_{1-6}$alkyl, $C_{3-7}$cycloalkyl$C_{2-6}$alkenyl, $C_{3-7}$cycloalkyl$C_{2-6}$alkynyl, $C_{5-7}$cycloalkenyl, $C_{3-7}$cycloalkenyl$C_{1-6}$alkyl, $C_{5-7}$cycloalkenyl$C_{2-6}$alkenyl, $C_{5-7}$cycloalkenyl$C_{2-6}$-alkynyl, 5- or 6-membered heteroaryl, 5- or 6-membered heteroaryl$C_{1-6}$alkyl, 5- or 6-membered saturated or partially saturated heterocyclyl or 5- or 6-membered saturated or partially saturated heterocyclyl$C_{1-6}$alkyl; or wherein R$^a$ and R$^{a1}$ together with the amide nitrogen to which they are attached (NR$^a$R$^{a1}$) form an amino acid residue or ester thereof;

or R$^1$ is of the formula —CONHSO$_2$R$^b$ or —C$_{1\text{-}3}$alkylCONHSO$_2$R$^b$ wherein R$^b$ is optionally substituted: C$^{1\text{-}10}$alkyl, C$_{2\text{-}10}$alkenyl, C$_{2\text{-}10}$alkynyl, C$_{3\text{-}7}$cycloalkyl, C$_{3\text{-}7}$cycloalkylC$_{1\text{-}6}$alkyl, C$_{3\text{-}7}$cycloalkylC$_{2\text{-}6}$alkenyl, C$_{3\text{-}7}$cycloalkylC$_{2\text{-}6}$alkynyl, C$_{5\text{-}7}$cycloalkenyl, C$_{3\text{-}7}$cycloalkenylC$_{1\text{-}6}$alkyl, C$_{5\text{-}7}$cycloalkenylC$_{2\text{-}6}$alkenyl, C$_{5\text{-}7}$cycloalkenylC$_{2\text{-}6}$alkynyl, 5- or 6-membered heteroaryl, 5- or 6-membered heteroarylC$_{1\text{-}6}$alkyl, phenyl, phenylC$_{1\text{-}6}$alkyl, 5- or 6-membered saturated or partially saturated heterocyclyl or 5- or 6-membered saturated or partially saturated heterocyclylC$_{1\text{-}6}$alkyl;

or R$^1$ is of the formula —CONR$^a$N(R$^c$)R$^d$ or —C$_{1\text{-}3}$alkylCONR$^a$N(R$^c$)R$^d$ wherein R$^a$ is as hereinabove defined, R$^c$ is hydrogen or C$_{1\text{-}6}$alkyl and R$^d$ is hydrogen, hydroxy or optionally substituted: C$_{1\text{-}10}$alkyl, C$_{2\text{-}10}$alkenyl, C$_{2\text{-}10}$alkynyl, C$_{3\text{-}7}$cycloalkyl, C$_{3\text{-}7}$cycloalkylC$_{1\text{-}6}$alkyl, C$_{3\text{-}7}$cycloalkylC$_{2\text{-}6}$alkenyl, C$_{3\text{-}7}$cycloalkylC$_{2\text{-}6}$alkynyl, C$_{5\text{-}7}$cycloalkenyl, C$_{5\text{-}7}$cycloalkenylC$_{1\text{-}6}$alkyl, C$_{5\text{-}7}$cycloalkenylC$_{2\text{-}6}$alkenyl, C$_{5\text{-}7}$cycloalkenylC$_{2\text{-}6}$alkynyl, 5- or 6-membered heteroaryl, 5- or 6-membered heteroarylC$_{1\text{-}6}$alkyl, 5- or 6-membered saturated or partially saturated heterocyclyl, 5- or 6-membered saturated or partially saturated heterocyclylC$_{1\text{-}6}$alkyl, or R$^c$ and R$^d$, together with the nitrogen atom to which they are attached, form a 4 to 8-membered saturated or partially saturated heterocyclic ring or form an amino acid residue or ester thereof;

R$^2$ is hydrogen, C$_{1\text{-}6}$alkyl (optionally substituted by hydroxy, cyano, nitro, amino, halo, C$_{1\text{-}4}$alkanoyl, C$_{1\text{-}4}$alkoxy or trifluoromethyl) C$_{2\text{-}6}$alkenyl, C$_{2\text{-}6}$alkynyl, C$_{3\text{-}6}$cycloalkyl, C$_{3\text{-}6}$cycloalkylC$_{1\text{-}3}$alkyl, C$_{3\text{-}6}$cycloalkylC$_{2\text{-}3}$alkenyl, C$_{5\text{-}6}$-cycloalkenyl, C$_{5\text{-}6}$cycloalkenylC$_{1\text{-}3}$alkyl, C$_{5\text{-}6}$cycloalkenylC$_{2\text{-}3}$alkenyl, phenylC$_{1\text{-}3}$alkyl or 5- or 6-membered heteroarylC$_{1\text{-}3}$alkyl;

R$^3$ is hydrogen or C$_{1\text{-}4}$alkyl;

R$^4$ is hydrogen or C$_{1\text{-}4}$alkyl;

or N-oxides of —NR$^2$ where chemically possible;

or S-oxides of sulphur containing rings where chemically possible;

or a pharmaceutically acceptable salt or an in vivo hydrolysable ester or amide thereof.

2. A compound according to claim 1 wherein B is optionally substituted pyridazinyl.

3. A compound according to claim 1 wherein R$^3$ is hydrogen or methyl and R$^4$ is hydrogen.

4. A compound according to claim 1 wherein R$^2$ is hydrogen, ethyl, allyl or 2-propynyl.

5. A compound according to claim 1 wherein A is either unsubstituted or substituted by halo, trifluoromethyl, nitro, hydroxy, amino, C$_{1\text{-}4}$alkylamino, diC$_{1\text{-}4}$alkylamino, cyano, C$_{1\text{-}6}$alkoxy, S(O)$_p$C$_{1\text{-}6}$alkyl (p is 0, 1 or 2), C$_{1\text{-}6}$alkyl (optionally substituted by hydroxy, amino, halo, nitro or cyano), S(O)$_p$CF$_3$ (p=0,1 or 2), carbamoyl, C$_{1\text{-}4}$alkylcarbamoyl, di(C$_{1\text{-}4}$alkyl)carbamoyl, C$_{2\text{-}6}$alkenyl, C$_{2\text{-}6}$alkynyl, C$_{2\text{-}4}$alkenylamino, N-C$_{2\text{-}4}$alkenyl-N-C$_{1\text{-}4}$alkylamino, di-C$_{2\text{-}4}$alkenylamino, S(O)pC$_{2\text{-}6}$alkenyl, N-C$_{2\text{-}4}$alkenyl-N-alkylamino, di-C$_{2\text{-}4}$alkenylcarbamoyl, C$_{3\text{-}7}$cycloalkyl, C$_{3\text{-}7}$cycloalkylC$_{1\text{-}3}$alkyl, C$_{3\text{-}7}$cycloalkylC$_{2\text{-}3}$alkenyl, C$_{5\text{-}7}$cycloalkenyl, C$_{5\text{-}7}$cycloalkenylC$_{1\text{-}3}$alkyl, C$_{5\text{-}7}$cycloalkenylC$_{2\text{-}3}$alkenyl, C$_{5\text{-}7}$cycloalkenylC$_{2\text{-}3}$alkynyl, C$_{1\text{-}4}$alkoxycarbonylamino, C$_{1\text{-}4}$alkanoylamino, C$_{1\text{-}4}$alkanoyl(N-C$_{1\text{-}4}$alkyl)amino, C$_{1\text{-}4}$alkanesulphonamido, benzenesulphonamido, aminosulphonyl, C$_{1\text{-}4}$alkylaminosulphonyl, di(C$_{1\text{-}4}$alkyl)aminosulphonyl, C$_{1\text{-}4}$alkoxycarbonyl, C$_{1\text{-}4}$alkanoyloxy, C$_{1\text{-}6}$alkanoyl, formylC$_{1\text{-}4}$alkyl, trifluoroC$_{1\text{-}3}$alkylsulphonyl, hydroxyiminoC$_{1\text{-}6}$alkyl, C$_{1\text{-}4}$alkoxyiminoC$_{1\text{-}6}$alkyl C$_{1\text{-}6}$alkylcarbamoylamino, oxazolyl, pyridyl, thiazolyl, pyrimidyl, pyrazinyl or pyridazinyl.

6. A compound according to claim 1 wherein B is either unsubstituted or substituted by amino, C$_{1\text{-}4}$alkylamino, di(C$_{1\text{-}4}$alkyl)amino, halo, trifluoromethyl, nitro, hydroxy, C$_{1\text{-}6}$alkoxy, C$_{1\text{-}6}$alkyl, cyano, —S(O)pC$_{1\text{-}6}$alkyl (p is 0, 1 or 2), carbamoyl, C$_{1\text{-}4}$alkylcarbamoyl or di(C$_{1\text{-}4}$alkyl)carbamoyl.

7. A compound according to claim 1 wherein D is either unsubstituted or substituted by halo, nitro, hydroxy, cyano, C$_{1\text{-}6}$alkyl, amino, C$_{1\text{-}6}$alkoxy or carbamoyl.

8. A compound according to claim 1 wherein R$^1$ is carboxy, carbamoyl, tetrazolyl or of the formula —CONR$^a$R$^{a1}$ or —CONHSO$_2$R$^b$ wherein R$^a$ is as defined in claim 1, R$^{a1}$ is hydrogen, hydroxy, optionally substituted: C$_{1\text{-}6}$alkyl, C$_{2\text{-}6}$alkenyl, C$_{2\text{-}6}$alkynyl, cyclopropylC$_{1\text{-}4}$alkyl, cyclobutylC$_{1\text{-}4}$alkyl, cyclopentylC$_{1\text{-}4}$alkyl, cyclohexylC$_{1\text{-}4}$alkyl, pyridylC$_{1\text{-}4}$alkyl, pyrimidylC$_{1\text{-}4}$alkyl, pyrazinylC$_{1\text{-}4}$alkyl, furylC$_{1\text{-}4}$alkyl, pyridazinylC$_{1\text{-}4}$alkyl, tetrazolylC$_{1\text{-}4}$alkyl, pyrrolidinylC$_{1\text{-}4}$alkyl, morpholinylC$_{1\text{-}4}$alkyl, imidazoliumC$_{1\text{-}4}$alkyl, N-methylimidazoliumC$_{1\text{-}4}$alkyl, pyridiniumC$_{1\text{-}4}$alkyl, pyridyl, pyrimidyl, pyrazinyl, pyridazinyl, N-methylpyrimidinium, N-methylimidazolyl, pyridinium, pyrimidinium, tetrazolyl, phenyl, cyclopropyl, cyclobutyl, cyclopentyl, cyclohexyl, cyclopentenyl, cyclohexenyl, cycloheptenyl, cyclopentenylC$_{1\text{-}4}$alkyl, cyclohexenylC$_{1\text{-}4}$alkyl or cycloheptenylC$_{1\text{-}4}$alkyl, and R$^b$ is C$_{1\text{-}4}$alkyl (optionally substituted by hydroxy, nitro, cyano, amino, C$_{1\text{-}4}$alkylamino, di-C$_{1\text{-}4}$alkylamino, C$_{1\text{-}4}$alkanoylamino, carbamoyl, C$_{1\text{-}4}$alkylcarbamoyl, di-(C$_{1\text{-}4}$alkyl)carbamoyl, halo, C$_{1\text{-}4}$alkoxy) or optionally substituted: phenylC$_{1\text{-}3}$alkyl, pyridylC$_{1\text{-}3}$ alkyl, phenyl, thienyl, thiadiazolyl, oxazolyl, isoxazolyl, pyrazolyl or 1,1-dioxidotetrahydrothienyl.

9. A compound of the formula (IV):

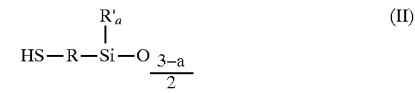

(II)

wherein

R$^1$ and R$^2$ are as defined in claim 1, R$^5$ is halo, nitro, hydroxy, amino, cyano, C$_{1\text{-}6}$alkyl, C$_{1\text{-}6}$alkoxy or carbamoyl, n is 0 or 1, R$^6$ is halo, nitro, trifluoromethyl, cyano, amino, C$_{1\text{-}6}$alkoxy, carbamoyl, C$_{1\text{-}4}$alkylcarbamoyl, di(C$_{1\text{-}4}$alkyl)carbamoyl, C$_{1\text{-}4}$alkanoylamino, S(O)$_p$C$_{1\text{-}6}$alkyl (where p is 0, 1 or 2), C$_{1\text{-}4}$alkanesulphonamido, benzenesulphonamido, C$_{1\text{-}6}$alkanoyl, C$_{1\text{-}4}$alkoxyaminoC$_{1\text{-}4}$alkyl or hydroxyiminoC$_{1\text{-}4}$alkyl and B is pyridazinyl.

10. A compound according to claim 1 which is:

6-[N-(2-benzyloxy-5-bromobenzyl)-N-ethylamino]pyridazine-3-carboxylic acid;

N-propyl-6-[N-(2-benzyloxy-5-bromobenzyl)-N-ethylamino]pyridazine-3-carboxamide;

N-(benzenesulphonyl)-6-[N-(2-benzyloxy-5-bromobenzyl)-N-ethylamino]pyridazine-3-carboxamide;

N-(3,5-dimethylisoxazole-4-sulphonyl)-6-[N-(2-benzyloxy-5-bromobenzyl)-N-ethylamino]pyridazine-3-carboxamide; or 5-[6-[N-(2-benzyloxy-5-bromobenzyl)-N-ethylamino)-3-pyridazine]tetrazole;

or pharmaceutically acceptable salts or in vivo hydrolysable esters or amides thereof.

11. A compound according to claim 1 which is

6-[N-(2-benzyloxy-5-bromobenzyl)-N-ethylamino] pyridazine-3-carboxylic acid;

or pharmaceutically acceptable salts or in vivo hydrolysable esters or amides thereof.

12. A pharmaceutical composition which comprises an effective amount of a compound according to claim 1 and a pharmaceutically acceptable carrier.

13. A method of relieving pain by administering an effective amount of a compound of the formula (I) according to claim 1 to a patient in need thereof.

* * * * *